US010894782B2

(12) United States Patent
Huryn et al.

(10) Patent No.: US 10,894,782 B2
(45) Date of Patent: Jan. 19, 2021

(54) MODULATORS OF P97 AAA ATPASE ACTIVITY

(71) Applicant: University of Pittsburgh—Of the Commonwealth System of Higher Education, Pittsburgh, PA (US)

(72) Inventors: Donna M. Huryn, Allentown, NJ (US); Peter Wipf, Pittsburgh, PA (US); Matthew G. LaPorte, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/301,080

(22) PCT Filed: May 11, 2017

(86) PCT No.: PCT/US2017/032099
§ 371 (c)(1),
(2) Date: Nov. 13, 2018

(87) PCT Pub. No.: WO2017/197080
PCT Pub. Date: Nov. 16, 2017

(65) Prior Publication Data
US 2019/0185448 A1    Jun. 20, 2019

Related U.S. Application Data

(60) Provisional application No. 62/334,969, filed on May 11, 2016.

(51) Int. Cl.
| | | |
|---|---|---|
| *C07D 401/04* | (2006.01) |
| *A61K 31/4196* | (2006.01) |
| *A61K 45/06* | (2006.01) |
| *A61K 31/44* | (2006.01) |
| *C07D 401/14* | (2006.01) |
| *C07D 405/14* | (2006.01) |
| *C07D 413/14* | (2006.01) |
| *C07D 417/14* | (2006.01) |

(52) U.S. Cl.
CPC ........ *C07D 401/04* (2013.01); *A61K 31/4196* (2013.01); *A61K 31/44* (2013.01); *A61K 45/06* (2013.01); *C07D 401/14* (2013.01); *C07D 405/14* (2013.01); *C07D 413/14* (2013.01); *C07D 417/14* (2013.01)

(58) Field of Classification Search
CPC .......................... C07D 249/12; A61K 31/4196
See application file for complete search history.

(56) References Cited

U.S. PATENT DOCUMENTS 7,767,881 B2    8/2010 Kotani et al.
2005/0288347 A1   12/2005 Hodge et al.

FOREIGN PATENT DOCUMENTS

| WO | WO 2005039569 | * | 5/2005 |
| WO | WO 2006/130160 A2 | | 12/2006 |
| WO | WO 2017/070320 A1 | | 4/2017 |
| WO | WO 2017/197080 A1 | | 11/2017 |

OTHER PUBLICATIONS

International Preliminary Report on Patentability issued in International Patent Application No. PCT/US2018/032062, dated Nov. 12, 2019.
International Search Report issued in International Patent Application No. PCT/US2018/032062, dated Sep. 13, 2018.
PubChem CID 70041846 Date Created Dec. 1, 2012, Dated Accessed: Aug. 27, 2018, 14 pages.
Magnaghi, et al., "Covalent and Allosteric Inhibitors of the ATPase VCP/p97 Induce Cancer Cell Death," *Nature Chemical Biology*, 12 pages (Jul. 2013).
International Search Report and Written Opinion issued in related International Patent Application No. PCT/US2017/032099, completed Jul. 13, 2017.
PUBCHEM, CHEMBL2315453, Jun. 11, 2013, pp. 1-7 [online], [retrieved on Jul. 12, 2017], Retrieved from the internet from https://pubchem.ncbi.nlm.nih.gov/compounds/71520307#section=2D-Structure; pp. 2-3,6.
PUBCHEM, CHEMBL2315448, Jun. 11, 2013, pp. 1-7 [online], [retrieved on Jul. 12, 2017], Retrieved from the internet from https://pubchem.ncbi.nlm.nih/gov/compounds/71521795#section=BioAssay-Results; pp. 2-3.
Alverez, et al., Allosteric Indole Amide Inhibitors of p97: Identification of a Novel Probe of the Ubiquitin Pathway, ACS Medicinal Chemistry Letters, vol. 7, pp. 182-187, p. 183, figure 1 (2016).
Arpicco et al., "Anticancer prodrugs: An overview of major strategies and recent developments," *Curr. Top. Med. Chem.*, 11: 2346-2381 (2011).
Banerjee, et al., "2.3 Å resolution cryo-EM structure of human p97 and mechanism of allosteric Inhibitition," *Sciencei*, vol. 331, No. 6275, pp. 871-875 (2016).
Blencowe et al., "Self-immolative linkers in polymeric delivery systems," *Polym. Chem.*, 2: 773-790 (2011); Arpicco et al., "Anticancer prodrugs: An overview of major strategies and recent developments," *Curr. Top. Med. Chem.* (Sharjah, United Arab Emirates), 11: 2346-2381 (2011).
Bodor, N., "Novel Approaches in Prodrug Design," *Drugs of the Future*, vol. 6, pp. 165-182 (1981).
Bundgaard, H., "Design of Prodrugs: Bioreversible-Derivatives for Various Functional Groups and Chemical Entities," in Design of Prodrugs, Elsevier (1985), 1 page Abstract.

(Continued)

*Primary Examiner* — Karen Cheng
(74) *Attorney, Agent, or Firm* — Foley & Lardner LLP

(57) ABSTRACT

The present invention is directed to methods of inhibiting or modulating p97 and compounds and compositions useful in such methods. Diseases and conditions that can be treated with the compounds and compositions of the invention include, but are not limited to, cancer and neurodegenerative disorders susceptible to treatment by modulation or inhibition of p97.

26 Claims, No Drawings

(56) References Cited

OTHER PUBLICATIONS

Deshaies et al., "Proteotoxic crisis, the ubiquitin-proteasome system, and cancer therapy," *BMC Biology*, 12(94), 14 pages (2014).
Huttunen et al., "Prodrugs—from serendipity to rational design," *Pharmacol. Rev.*, 63, 750-771 (2011).
Karaman, R., "Prodrugs design based on inter- and intramolecular chemical processes," *Chem. Biol. Drug Des.*, 82: 643-668 (2013).
Lee et al., "Pro-drug and Antedrug: Two Diametrical Approaches in Designing Safer Drugs," *Arch. Pharm. Res.*, 25: 111-136 (2002).
Meyer et al., "Emerging functions of the VCP/p97 AAA-ATPase in the ubiquitin system," *Nature Cell Biology*, 14: 117-123 (2012).
Meyer et al., "The VCP/p97 system at a glance: connecting cellular function to disease pathogenesis," *J. Cell Sci.*, 127: 1-7 (2014).
Notari, "Theory and Practice of Prodrug Kinetics," *Methods in Enzymology*, vol. 112, pp. 309-323 (1985).
Rautio et al., "Prodrugs: Design and clinical applications," *Nat. Rev. Drug Discovery*, 7: 255-270 (2008).
Simplicio et al., "Prodrugs for amines," *Molecules*, 13: 519-547 (2008).
Tietze et al., "Antibody-directed enzyme prodrug therapy: A promising approach for a selective treatment of cancer based on prodrugs and monoclonal antibodies" *Chem. Biol. Drug Des.*, 74: 205-211 (2009).
Valle et al., "Critical Role of VCP/p97 in the Pathogenesis and Progression of Non-Small Cell Lung Carcinoma," *PlosOne*, 6(12): e29073, 12 pages (2011).
Zhang et al., "Structure of the AAA ATPase p97," *Molecular Cell*, 6(6): 1473-1484 (2000).
Zhang, et al., "Altered cofactor regulation with disease-associated p97/VCP mutations," *Proc. Natl. Acad. Sci. USA*, 112(14), E1705-E1714 (2015).
Burnett, et al., "A Threonine Turnstile Defines a Dynamic Amphiphilic Binding Motif in the AAA AtPase p97 Allosteric Binding Site," *Organic & Biomolecular Chemisty*, vol. 15, No. 19, pp. 4096-4114 (May 2016).
Paolo Polucci et al., "Alkylsulfanyl-1,2,4-triazoles, a New Class of Allosteric Valosine Containing Protein Inhibitors, Synthesis and Structure-Activity Relationships," *Journ. Of Medicinal Chemistry*, vol. 56, No. 2, pp. 437-450 (Jan. 2013).
International Search Report issued in International Patent Application No. PCT/US2019/026888, dated Jun. 5, 2019.

\* cited by examiner

MODULATORS OF P97 AAA ATPASE ACTIVITY

CROSS-REFERENCE TO RELATED APPLICATIONS

This application is the U.S. National Stage of International Patent Application No. PCT/US2017/032099, filed May 11, 2017, which claims the benefit of priority from U.S. Provisional Patent Application No. 62/334,969, filed May 11, 2016, the contents of which are incorporated herein by reference in their entirety.

STATEMENT OF GOVERNMENT SUPPORT

This invention was made with government support under HHSN261200800001E awarded by the NIH. The government has certain rights in the invention.

BACKGROUND

The AAA ATPase p97 (also known as valosin-containing protein (VCP), Cdc48 in yeast and plants, CDC-48 in worms and Ter94 in flies), is a hexameric member of the AAA family (ATPases associated with diverse cellular activities). Zhang et al., "Structure of the AAA ATPase p97," *Mol. Cell*, 6(6): 1473-84 (2000).

Recent studies have uncovered cellular functions for p97 in autophagy, endosomal sorting and regulation of protein degradation at the outer mitochondrial membrane, and elucidated a role for p97 in key chromatin-associated processes. These findings extend the functional relevance of p97 to lysosomal degradation and reveal a dual role in protecting cells from protein stress and ensuring genome stability during proliferation. Meyer et al., "Emerging functions of the VCP/p97 AAA-ATPase in the ubiquitin system," *Nature Cell Biol.*, 14: 117-123 (2012).

p97 also functions as an interaction hub, and different sets of at least 30 cofactors have been shown to be responsible for modulating p97-mediated processes. Meyer et al., "The VCP/p97 system at a glance: connecting cellular function to disease pathogenesis," *J. Cell Sci.*, 127: 1-7 (2014).

A 2.3 Å resolution cryo-EM structure of human p97 and mechanism of allosteric inhibition was recently disclosed. Banerjee et al., *Science*, 351(6275): 871-875 (2016). Other structures have also been disclosed. Wipf et al., *Organic & Biomolecular Chemistry*, (2017), DOI: 10.1039/C7OB00526A.

p97-Associated Disease:

p97 is a potential therapeutic target for cancer and neurodegenerative diseases. Given the crucial role of p97 in maintaining cellular proteostasis, it is not surprising that autosomal dominant mutations in p97, the gene encoding p97, lead to a rare multisystem degenerative disorder previously termed IBMPFD/ALS. The acronym IBMPFD/ALS refers to the four main phenotypes that can affect patients carrying disease-associated mutations of p97 (i.e., inclusion body myopathy (IBM), Paget's disease of the bone (PDB), frontotemporal dementia (FTD) and amyotrophic lateral sclerosis (ALS)). However, a patient with a pathogenic p97 mutation can have any mixture of phenotypes, including all four phenotypes or just one phenotype in isolation. In addition, a member of the same family can have any combination of phenotypes. Id.

Some carriers of p97 mutation also manifest additional symptoms, including Parkinsonism, ataxia, cataracts, dilated cardiomyopathy, hepatic fibrosis, and hearing loss. The term 'multisystem proteinopathy' has been proposed as the nomenclature for an emerging family of genetic disorders that are unified by this characteristic variation in the penetrance of muscle, bone and CNS degenerative phenotypes along with the accumulation of ubiquitin and TDP-43-positive inclusions.

The protein p97 plays an important role in protein homeostasis. However, in numerous disease states, homeostasis is dysregulated, and inhibitors and/or modulators of p97 have the potential to address diseases such as cancer, and neurodegenerative disorders. The compounds described inhibit the ATPase activity of p9'7, have effects on p97-dependent mechanisms in cells and exhibit anti-proliferative activity. They have the potential to be anti-cancer agents, or drugs that are effective in neurodegenerative diseases, or any other disorder that relies on p97.

There remains a need in the art for inhibitors and/or modulators of p97 useful in treating cancer and neurodegenerative disorders caused by proteostatic malfunction. The present invention satisfies these needs. Further, there remains a need for compounds that are more efficacious with fewer side effects than other compounds that work through similar or unrelated p97 inhibition mechanisms.

SUMMARY OF THE DISCLOSED SUBJECT MATTER

The present invention is directed to methods of modulating p97 or inhibiting p97, and compounds and compositions useful in such methods. Diseases and conditions the can be treated with the compounds and compositions of the invention include, but are not limited to, cancer and neurodegenerative disorders susceptible to treatment by modulation or inhibition of p97. Exemplary neurodegenerative disorders include, but are not limited to, inclusion body myopathy (IBM), Paget's disease of the bone (PDB), frontotemporal dementia (FTD) and amyotrophic lateral sclerosis (ALS).

Subjects having p97 mutations may also be treated with the compounds and compositions according to the invention. Such p97 mutations may manifest symptoms including but not limited to Parkinsonism, ataxia, cataracts, dilated cardiomyopathy, hepatic fibrosis, and hearing loss. Treatment with a compound or composition according to the invention may ameliorate such symptoms.

In one aspect, provided is a compound having a structure of formula (I):

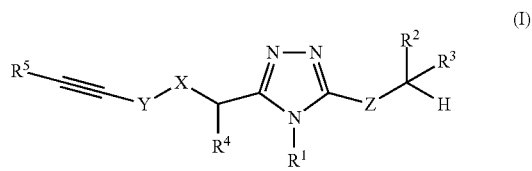

or a pharmaceutically acceptable salt, solvate or prodrug thereof, wherein:

Z is O, $SO_{0-2}$, NR, $C(R^7)_2$, alkenyl or alkynyl;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl or an optionally substituted 5- or 6-membered heteroaryl;

$R^4$ is H, $C(R^7)_2$, aryl, or heteroaryl;

X is O or $SO_{0-2}$;

Y is an optionally substituted alkyl, alkenyl, aryl, heteroaryl, cycloalkyl, or heterocycle;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

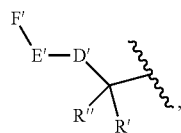

where
- R' and R" are each independently selected from H, optionally substituted alkyl, —OR, halogen, —N(R)$_2$, and optionally substituted cycloalkyl or heterocycle;
- or R' and R" may together form a 3- to 6-membered cycloalkyl or heterocycle that is optionally substituted;
- D' is selected from the group consisting of —O—, —NR—, —OCONR—, —NRSO$_2$—, —NRCO—, —NRSO$_2$NR—, —NRCOO—, —NRCONR—, and —NRC(NR)NR—;
- E' is selected from a bond or an optionally substituted $C_1$-$C_6$ alkyl or cycloalkyl;
- F' is selected from the group consisting of H, an optionally substituted cycloalkyl, an optionally substituted heterocycle, an optionally substituted aryl, and an optionally substituted heteroaryl;
- R is selected from the group consisting of H, optionally substituted alkyl, and optionally substituted cycloalkyl; and
- $R^7$ is selected from the group consisting of H, halogen, optionally substituted alkyl, optionally substituted cycloalkyl, —OR, and —N(R)$_2$.

In some embodiments, X is O or S. In some embodiments, Y is selected from:

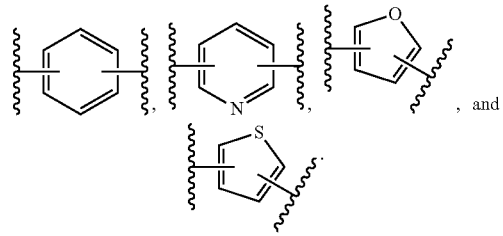

In some embodiments, Z is selected from O, S and CH$_2$. In some embodiments, $R^5$ is a phenyl, optionally substituted with one or more alkyl, —OR, —CN, —CO$_2$R, halogen, —SR, —SOR, —SO$_2$R, —SF$_5$ or —NR$_2$. In some embodiments, $R^5$ is a heterocycle optionally substituted with one or more alkyl, —OR, —CN, —CO$_2$R, halogen, —SR, —SOR, —SO$_2$R, —SF$_5$ or —NR$_2$. In some embodiments, $R^5$ is

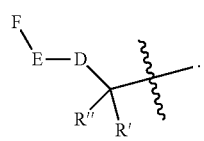

In some embodiments, R' and R" together form a 3- to 6-membered cycloalkyl or heterocycle. In some embodiments, R' and R" are each H, or at least one of R' and R" is methyl and any remaining R' or R" is H. In some embodiments, at least one of R' and R" is an optionally substituted alkyl. In some embodiments, E' is a $C_1$-$C_6$ alkyl and F' is H. In some embodiments, F' is an optionally substituted cycloalkyl selected from the group consisting of cyclopropyl, cyclobutyl, cyclopentyl, and cyclohexyl. In some embodiments, F' is an optionally substituted heterocycle selected from the group consisting of morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, F' is an optionally substituted aryl selected from: phenyl, optionally substituted with one or more of: alkyl, —CF$_3$, —OR, —CN, —CO$_2$R, halogen, —SR, —SOR, —SO$_2$R, —SF$_5$ or —NR$_2$. In some embodiments, F' is an optionally substituted heteroaryl selected from the group consisting of alkyl-triazole, tetrazole, imidazole, and isoxazole. In some embodiments, $R^1$ is pyridine. In some embodiments, $R^2$ and $R^3$ together are a cyclopropyl, cyclopentyl or cyclohexene. In some embodiments, Y is an optionally substituted

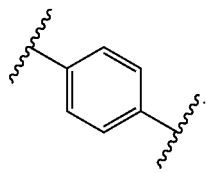 [SMILES: *c1ccc(*)cc1]

In another aspect, provided is a compound having a structure of formula (I'):

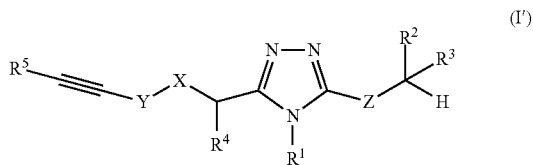

or a pharmaceutically acceptable salt, solvate or prodrug thereof, wherein:

Z is O, SO$_{0-2}$, NR, C(R$^7$)$_2$, alkenyl or alkynyl;

$R^2$ and $R^3$ are independently optionally substituted $C_{1-6}$ alkyl, optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring;

$R^1$ is optionally substituted phenyl, optionally substituted 5- or 6-membered heteroaryl, or optionally substituted non-aromatic heterocyclic;

$R^4$ is H, C(R$^7$)$_2$, aryl, or heteroaryl;

X is O, SO$_{0-2}$, or NR;

Y is an optionally substituted alkyl, optionally substituted alkenyl, optionally substituted aryl, optionally substituted heteroaryl, optionally substituted cycloalkyl, or optionally substituted non-aromatic heterocycle;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

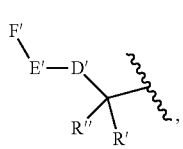

where
- R' and R" are each independently selected from the group consisting of H, optionally substituted alkyl, —OR, halogen, —N(R)$_2$, optionally substituted cycloalkyl, and optionally substituted heterocycle;
- or R' and R" may together form an optionally substituted 3- to 6-membered cycloalkyl or optionally substituted 3- to 6-membered heterocycle;
- D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
- E' is selected from the group consisting of a bond, an optionally substituted C$_1$-C$_6$ alkyl, optionally substituted C$_1$-C$_6$ alkenyl, and optionally substituted cycloalkyl; and
- F' is selected from the group consisting of H, an optionally substituted cycloalkyl, an optionally substituted non-aromatic heterocycle, an optionally substituted aryl, and an optionally substituted heteroaryl;
- R is independently selected from the group consisting of H, optionally substituted alkyl, and optionally substituted cycloalkyl; and
- R$^7$ is independently selected from the group consisting of H, halogen, optionally substituted alkyl, optionally substituted cycloalkyl, —OR, and —N(R)$_2$.

In another aspect, provided is a compound having a structure of formula (II):

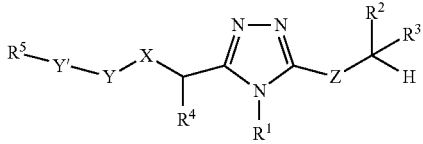

(II)

or a pharmaceutically acceptable salt, solvate or prodrug thereof, wherein:
- X is O, SO$_{0-2}$, or NR;
- Y is optionally substituted alkyl, optionally substituted alkenyl, alkynyl, optionally substituted aryl, optionally substituted heteroaryl, optionally substituted cycloalkyl, or optionally substituted non-aromatic heterocyclic;
- Y' is alkynyl, optionally substituted heteroaryl, optionally substituted cycloalkyl, or optionally substituted non-aromatic heterocyclic;
- R$^2$ and R$^3$ are independently optionally substituted C$_{1-6}$ alkyl, optionally substituted C$_{1-9}$ cyclic, optionally substituted C$_{3-9}$ heterocyclic, or halogen, or R$^2$ and R$^3$ together form an optionally substituted C$_{3-9}$ cyclic or optionally substituted 3- to 9-membered heterocyclic ring;
- Z is O, SO$_{0-2}$, NR, C(R$^7$)$_2$, alkenyl or alkynyl;
- R$^1$ is optionally substituted phenyl, optionally substituted 5- or 6-membered heteroaryl, or optionally substituted non-aromatic heterocyclic;
- R$^4$ is H, C(R$^7$)$_2$, aryl, or heteroaryl;
- R$^5$ is H, nitrile, an optionally substituted aryl, an optionally substituted heterocycle, optionally substituted C$_1$-C$_6$ alkyl, optionally substituted C$_3$-C$_9$ cycloalkyl, or

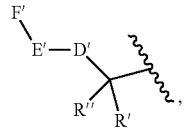

where
- R' and R" are each independently selected from the group consisting of H, optionally substituted alkyl, —OR, halogen, —N(R)$_2$, optionally substituted cycloalkyl, and optionally substituted heterocycle;
- or R' and R" may together form an optionally substituted 3- to 6-membered cycloalkyl or optionally substituted 3- to 6-membered heterocycle;
- D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
- E' is selected from the group consisting of a bond, an optionally substituted C$_1$-C$_6$ alkyl, optionally substituted C$_1$-C$_6$ alkenyl, and optionally substituted cycloalkyl; and
- F' is selected from the group consisting of H, an optionally substituted cycloalkyl, an optionally substituted non-aromatic heterocycle, an optionally substituted aryl, and an optionally substituted heteroaryl;
- R is independently selected from the group consisting of H, optionally substituted alkyl, and optionally substituted cycloalkyl; and
- R$^7$ is independently selected from the group consisting of H, halogen, optionally substituted alkyl, optionally substituted cycloalkyl, —OR, and —N(R)$_2$.

Some embodiments include a compound selected from those depicted in Tables I or III, or a pharmaceutically acceptable salt, solvate or prodrug thereof.

Some embodiments include a pharmaceutical composition comprising a compound of any one of the embodiments herein and at least one pharmaceutically acceptable excipient.

In another aspect, provided is a method of inhibiting p97 in a subject in need thereof, comprising administering to the subject a therapeutically effective amount of a compound of any one of the embodiments herein or a therapeutically effective amount of a pharmaceutical composition of any one of the embodiments herein.

In another aspect, provided is a method of modulating p97 in a subject in need thereof, comprising administering to the subject a therapeutically effective amount of a compound of any one of the embodiments herein or a therapeutically effective amount of a pharmaceutical composition of any one of the embodiments herein.

In another aspect, provided is a method of treating cancer or a neurodegenerative disease susceptible to treatment by p97 inhibition in a subject in need thereof comprising administering to the subject a therapeutically effective amount of a compound of any one of the embodiments herein or a therapeutically effective amount of a pharmaceutical composition of any one of the embodiments herein. In some embodiments, the method is a method of treating cancer susceptible to treatment by p97 inhibition, and wherein the cancer is selected from the group consisting of a solid tumor, non-small cell lung carcinoma, multiple myeloma, and mantle cell lymphoma. In some embodiments, the method is a method of treating a neurodegenerative disease susceptible to treatment by p97 inhibition, and wherein the neurodegenerative disease is selected from the group consisting of inclusion body myopathy (IBM), Paget's disease of the bone (PDB), frontotemporal dementia (FTD) and amyotrophic lateral sclerosis (ALS).

In another aspect, provided is a method of treating cancer or a neurodegenerative disease susceptible to treatment by p97 modulation in a subject in need thereof comprising administering to the subject a therapeutically effective amount of a compound of any one of the embodiments herein or a therapeutically effective amount of a pharmaceutical composition of any one of the embodiments herein. In some embodiments, the method is a method of treating cancer susceptible to treatment by p97 modulation, and wherein the cancer is selected from the group consisting of a solid tumor, non-small cell lung carcinoma, multiple myeloma, and mantle cell lymphoma. In some embodiments, the method is a method of treating a neurodegenerative disease susceptible to treatment by p97 modulation, and wherein the neurodegenerative disease is selected from the group consisting of inclusion body myopathy (IBM), Paget's disease of the bone (PDB), frontotemporal dementia (FTD) and amyotrophic lateral sclerosis (ALS).

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

DETAILED DESCRIPTION

I. Compounds of the Disclosure

The present disclosure includes compounds having the following core structure:

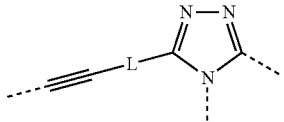

wherein L is a linking group, and the dashed lines are further functionalizations. The linking group and the further functionalizations are described in greater detail herein.

In some embodiments, compounds of the present disclosure include those represented by the following Formula (I):

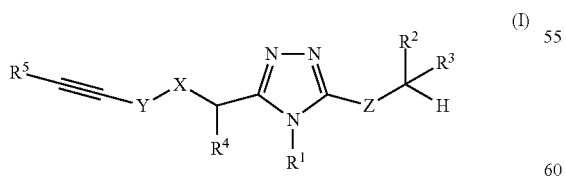

or a pharmaceutically acceptable salt, solvate or prodrug thereof, wherein:

Z is O, $SO_{0-2}$, NR, $C(R^7)_2$, alkenyl or alkynyl;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl or an optionally substituted 5- or 6-membered heteroaryl;

$R^4$ is H, $C(R^7)_2$, aryl, or heteroaryl;

X is O or $SO_{0-2}$;

Y is an optionally substituted alkyl, alkenyl, aryl, heteroaryl, cycloalkyl, or heterocycle;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

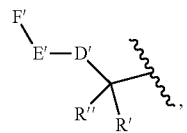

where

R' and R" are each independently selected from the group consisting of H, optionally substituted alkyl, —OR, halogen (e.g., F, Cl, Br, I), —N(R)$_2$, and optionally substituted cycloalkyl or heterocycle;

or R' and R" may together form a 3- to 6-membered cycloalkyl or heterocycle that is optionally substituted;

D' is selected from the group consisting of —O—, —NR—, —OCONR—, —NRSO$_2$—, —NRCO—, —NRSO$_2$NR—, —NRCOO—, —NRCONR—, and —NRC(NR)NR—;

E' is selected from a bond or an optionally substituted $C_1$-$C_6$ alkyl and cycloalkyl; and F' is selected from the group consisting of H, an optionally substituted cycloalkyl, an optionally substituted heterocycle, an optionally substituted aryl, and an optionally substituted heteroaryl;

R is selected from the group consisting of H, optionally substituted alkyl, and optionally substituted cycloalkyl; and $R^7$ is selected from the group consisting of H, halogen, optionally substituted alkyl, optionally substituted cycloalkyl, —OR, and —N(R)$_2$.

In Formula (I), X is one of the following moieties: O, S, SO, or SO$_2$.

In Formula (I), Y is an optionally substituted alkyl, alkenyl, aryl, heteroaryl, cycloalkyl, or heterocycle. In some embodiments, Y is selected from the group consisting of an optionally substituted alkyl, an optionally substituted aryl, an optionally substituted heteroaryl, an optionally substituted $C_3$-$C_{10}$ cycloalkyl, and an optionally substituted heterocycle (containing one or more O, S, SO, SO$_2$, B, N, or NR). In some embodiments, Y is selected from the group consisting of:

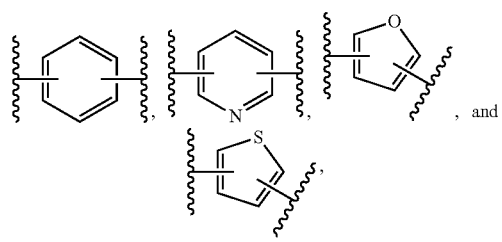

each of which may be optionally substituted. In a preferred embodiment, Y is

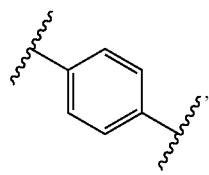 [SMILES: *c1ccc(*)cc1]

which may be optionally substituted, for example the phenylene may be substituted alkyl or cycloalkyl, halogen, —$NR_2$, —$SF_5$ and —OR. In some embodiments, the phenylene is substituted by methyl or perfluoromethyl. In some embodiments, the substitution is at a position ortho to the alkyne. Other examples within these embodiments, include phenylene moieties substituted by one or more fluoro moiety. For example:

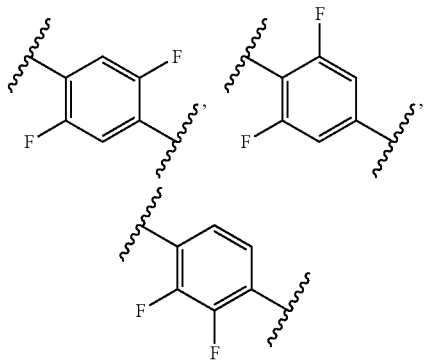

and further substituted variants thereof, e.g.,

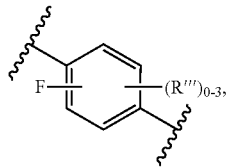

where R''' is a halogen (e.g., F, Cl, or Br), nitrile, a $C_1$-$C_6$ alkyl, or O—$C_1$-$C_6$ alkyl. In some embodiments, the phenylene is di-substituted, for example,

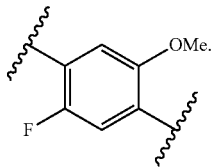 [SMILES: *c1cc(OC)c(*)cc1F]

In some embodiments, Y is phenylene optionally substituted with $C_1$-$C_6$ alkyl, $C_1$-$C_6$ haloalkyl, halogen, $C_1$-$C_6$ alkoxy, nitrile, or a combination of two or more thereof.
In some embodiments, Y is cyclobutene, propellane, cubane or

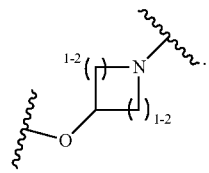

In some embodiments, Y is cyclobutane, cyclobutene, propellane (such as, but not limited to, [1.1.1.0$^{1,3}$] propellane), cubane, or

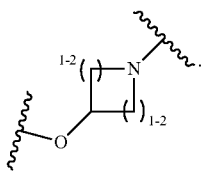

In Formula (I), Z is O, $SO_{0-2}$, NR, $C(R^7)_2$, alkenyl or alkynyl. In some preferred embodiments, Z is selected from O, S or $C(R^7)_2$, where $R^7$ is independently H, halogen, optionally substituted alkyl, optionally substituted cycloalkyl, or —$N(R)_2$. In some embodiments, R or $R^7$ is preferably H. In some embodiments, Z is S.

In Formula (I), $R^5$ is H, nitrile, an optionally substituted aryl, an optionally substituted heterocycle, optionally substituted $C_1$-$C_6$ alkyl, optionally substituted $C_3$-$C_9$ cycloalkyl, or

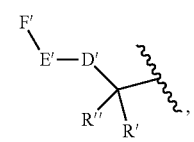

where R' and R'' are each independently selected from the group consisting of H, optionally substituted alkyl, —OR, halogen (e.g., F, Cl, Br, or I), —$N(R)_2$, and optionally substituted cycloalkyl or heterocycle;
or R' and R'' may together form a 3- to 6-membered cycloalkyl or heterocycle that is optionally substituted;
D' is selected from the group consisting of —O—, —NR—, —OCONR—, —$NRSO_2$—, —NRCO—, —$NRSO_2NR$—, —NRCOO—, —NRCONR—, and —NRC(NR)NR—;
E' is selected from the group consisting of a bond, an optionally substituted $C_1$-$C_6$ alkyl and cycloalkyl; and
F' is selected from the group consisting of H, an optionally substituted cycloalkyl, an optionally substituted heterocycle, an optionally substituted aryl, and an optionally substituted heteroaryl.

When $R^5$ is an optionally substituted aryl, the moiety may be, e.g., a phenyl that is unsubstituted or substituted. In some embodiments, the phenyl may be substituted with one or more of alkyl, —OR, —CN, —$CO_2R$, halogen, —SR, —SOR, —$SO_2R$, —$SF_5$ and —$NR_2$.

When $R^5$ is an optionally substituted heterocycle, the moiety may be, e.g., morpholine or pyridine, optionally substituted with one or more alkyl, —OR, —CN, —$CO_2R$, halogen, —SR, —SOR, —$SO_2R$, —$SF_5$ or —$NR_2$.

In some embodiments, $R^5$ is $C_1$-$C_6$ alkyl optional substituted with alkoxy, hydroxy, amino, heterocyclyl, cycloalkyl, aryl, heteroaryl, or a combination of two or more thereof. In some embodiments, $R^5$ is H.

In Formula (I), when $R^5$ is:

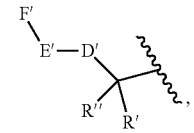

D', E' and F' may be defined as follows:
D' may be selected from the group consisting of —O—, —NR—, —OCONR—, —$NRSO_2$—, —NRCO—, —$NRSO_2NR$—, —NRCOO—, —NRCONR—, and —NRC(NR)NR—;

E' may be selected from a bond or an optionally substituted $C_1$-$C_6$ alkyl and cycloalkyl; and F' may be selected from the group consisting of H, halogen, an optionally substituted cycloalkyl, an optionally substituted heterocycle, an optionally substituted aryl, and an optionally substituted heteroaryl.

D' is —O—, —NR—, —OCONR—, —NRSO$_2$—, —NRCO—, —NRSO$_2$NR—, —NRCOO—, —NRCONR—, or —NRC(NR)NR—, where R is defined previously. In some embodiments, D' may be selected from the group consisting of O, NH, OCONH, NHSO$_2$, NHCO, NHSO$_2$NH, NHCOO, and NHCONH.

E' may be a bond or an optionally substituted $C_1$-$C_6$ alkyl or cycloalkyl. In some embodiments, E' is an optionally substituted $C_1$-$C_6$ alkyl. In some embodiments, E' is an optionally substituted $C_1$-$C_6$ alkyl and F' is H. In other embodiments, E' is an optionally substituted $C_1$-$C_6$ alkyl that is substituted by a $C_3$-$C_7$ spirocycle. In some embodiments, E' may be an optionally substituted $C_3$-$C_6$ cycloalkyl, (e.g., optionally substituted with alkyl, halogen, or —OR). In some embodiments the cycloalkyl is specifically selected from, e.g., one of the following: cyclopropyl, cyclobutyl, cyclopentyl, and cyclohexyl, each of which may be optionally substituted.

F' may be selected from the group consisting of H, an optionally substituted cycloalkyl, an optionally substituted heterocycle, an optionally substituted aryl, and an optionally substituted heteroaryl. In some embodiments, F' is an optionally substituted cycloalkyl, an optionally substituted heterocycle, an optionally substituted aryl, and an optionally substituted heteroaryl, each of which is described below in further detail. In some embodiments, F' is substituted with one or more alkyl, perfluoroalkyl (e.g., CF$_3$), —OR, —CN, —CO$_2$R, halogen, —SR, —SOR, —SO$_2$R, —SF$_5$ or —NR$_2$. In other embodiments, F' is not substituted.

In some embodiments, F' is an optionally substituted cycloalkyl. For example, F' may be a $C_3$-$C_6$ cycloalkyl, optionally substituted with alkyl, halogen, or —OR. In some embodiments the cycloalkyl is specifically selected from, e.g., one of the following: cyclopropyl, cyclobutyl, cyclopentyl, and cyclohexyl, each of which may be optionally substituted. In some embodiments the cycloalkyl is specifically selected from, e.g., one of the following: cyclopropyl, cyclobutyl, cyclopentyl, cyclohexyl, and propellane, each of which may be optionally substituted. In some embodiments, E' is a bond and F' is an optionally substituted cycloalkyl. In some embodiments, E' is optionally substituted $C_1$-$C_6$ alkyl and F' is an optionally substituted cycloalkyl.

In some embodiments, F' is an optionally substituted heterocycle. For example, F' may be a 4-6 membered heterocycle, optionally substituted with alkyl, halogen, or OR. In some embodiments, the heterocycle contains one or more heteroatom selected from: O, S, SO, SO$_2$, B, N, and NR. Particular embodiments include, e.g., morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, E' is a bond and F' is an optionally substituted heterocycle. In some embodiments, E' is optionally substituted $C_1$-$C_6$ alkyl and F' is an optionally substituted heterocycle.

In some embodiments, F' is an optionally substituted aryl. For example, F' may be a $C_6$-$C_{10}$ aryl, e.g., a phenyl, that is optionally substituted, e.g., with one or more of alkyl, perfluoroalkyl (e.g., CF$_3$), —OR, —CN, —CO$_2$R, halogen, —SR, —SOR, —SO$_2$R, —SF$_5$ or —NR$_2$. In some embodiments, E' is a bond and F' is an optionally substituted aryl.

In some embodiments, E' is optionally substituted $C_1$-$C_6$ alkyl and F' is an optionally substituted aryl.

In some embodiments, F' is an optionally substituted heteroaryl. For example, F' may be a 5-6 membered heteroaryl, optionally substituted with alkyl, halogen, or OR. In some embodiments, the heteroaryl contains one or more heteroatom selected from the group consisting of O, S, SO, SO$_2$, B, N, and NR. Particular embodiments include, e.g., alkyl-triazole, tetrazole, imidazole, and isoxazole. In some embodiments, E' is a bond and F' is an optionally substituted heteroaryl. In some embodiments, E' is optionally substituted $C_1$-$C_6$ alkyl and F' is an optionally substituted heteroaryl.

In Formula (I), when $R^5$ is:

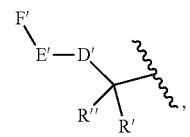

R' and R" may each independently selected from H, optionally substituted alkyl, —OR, halogen (e.g., F, Cl, Br, I), —N(R)$_2$, and optionally substituted cycloalkyl or heterocycle. In some embodiments, R' and R" are each H. In other embodiments, at least one of R' and R" is optionally substituted alkyl and any remaining R' or R" is H. In some embodiments, the optionally substituted alkyl is a $C_1$-$C_6$ alkyl or perfluoroalkyl. In some embodiments, the optionally substituted alkyl is methyl. In some embodiments, R' and R" are each independently optionally substituted $C_1$-$C_6$ alkyl.

Alternatively, R' and R" together may form a 3- to 6-membered cycloalkyl or heterocycle that is optionally substituted. In some embodiments, the 3- to 6-membered cycloalkyl or heterocycle is substituted by one or more R$^7$, as defined previously. In additional embodiments, R' and R" form a cyclopropyl, cyclobutyl, cyclopentyl, or cyclohexyl. In other embodiments, R' and R" form an oxetane. In some embodiments, R' and R" form an optionally substituted azetidine, oxetane, pyrrolidone or piperidine. In some embodiments, the nitrogen of the azetidine, pyrrolidone or piperidine may be substituted with R, SO$_2$R, COR, SO$_2$NR$_2$, CONR$_2$ and COOR. In some embodiments, when R' and R" form a ring, e.g., an optionally substituted cyclopropyl, cyclobutyl, cyclopentyl, or cyclohexyl, azetidine, oxetane, pyrrolidone or piperidine, then D'-E'-F' together form an —OH (i.e., D' is —O—, E' is a bond and F' is H).

In Formula (I), R$^1$ is an optionally substituted phenyl or an optionally substituted 5- or 6-membered heteroaryl. For example, in some embodiments, R$^1$ is optionally substituted phenyl or optionally substituted pyridine. In some embodiments, R$^1$ is an unsubstituted phenyl or an unsubstituted pyridine. In some embodiments, R$^1$ is a pyridine. In some embodiments the pyridine is attached at the 2 position, the 3 position or the 4 position, preferably the 3 position.

In Formula (I), R$^2$ and R$^3$ are independently an optionally substituted $C_{1-9}$ cyclic, $C_{3-9}$ heterocyclic, or halogen, or R$^2$ and R$^3$ together form an optionally substituted $C_{3-9}$ cyclic or 3- to 9-membered heterocyclic ring. In some embodiments, R$^2$ is a $C_1$-$C_6$ alkyl, a $C_3$-$C_{10}$ cycloalkyl (including cycloalkenyl), or a heterocycle, each of which maybe optionally substituted.

In some embodiments, R$^2$ and R$^3$ together form an optionally substituted $C_{3-9}$ cyclic or 3- to 9-membered heterocyclic ring, for example, a $C_3$-$C_{10}$ cycloalkyl (including cycloalkenyl), or a heterocycle, each of which maybe optionally substituted. Exemplary individual embodiments when $R^2$ and $R^3$ together form an optionally substituted $C_{3-9}$ cyclic or 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

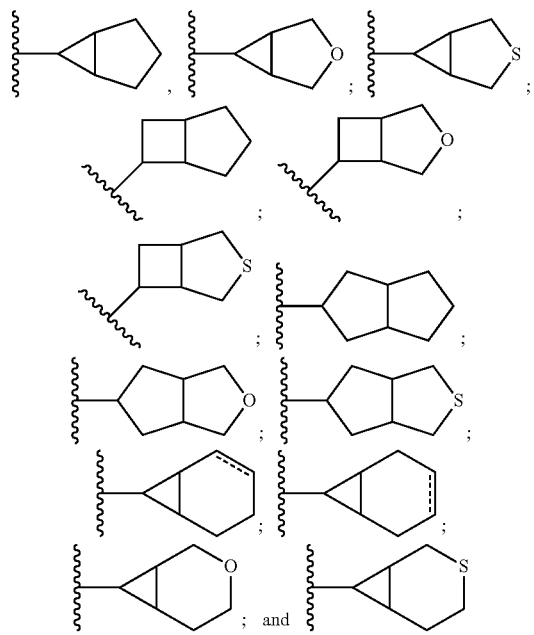

where one or more of the dashed bonds may optionally be a double bond and ⸹ indicates attachment to Z.

In some embodiments, one or more hydrogens in $R^2$ or $R^3$, or in both $R^2$ and $R^3$ are replaced with deuterium. In some embodiments, $R^2$ and $R^3$ form a perdeuterated cycloalkyl ring.

In some embodiments, $R^2$ and $R^3$ form a perdeuterated cyclopentane

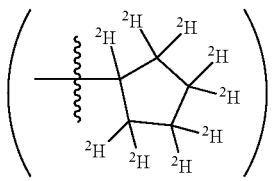

and ⸹ indicates attachment to Z. In some embodiments,

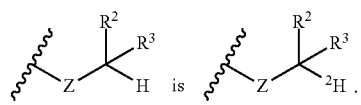

In some embodiments, compounds of the present disclosure include those represented by the following Formula (I'):

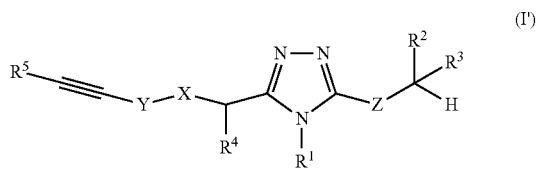

or a pharmaceutically acceptable salt, solvate or prodrug thereof, wherein:

Z is O, $SO_{0-2}$, NR, $C(R^7)_2$, alkenyl or alkynyl;

$R^2$ and $R^3$ are independently optionally substituted $C_{1-6}$ alkyl, optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

X is O, $SO_{0-2}$, or NR;

Y is an optionally substituted alkyl, optionally substituted alkenyl, optionally substituted aryl, optionally substituted heteroaryl, optionally substituted cycloalkyl, or optionally substituted non-aromatic heterocycle;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

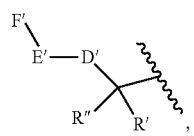

where

R' and R" are each independently selected from the group consisting of H, optionally substituted alkyl, —OR, halogen (e.g., F, Cl, Br, I), —$N(R)_2$, optionally substituted cycloalkyl, and optionally substituted heterocycle;

or R' and R" may together form an optionally substituted 3- to 6-membered cycloalkyl or optionally substituted 3- to 6-membered heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted alkyl, and optionally substituted cycloalkyl; and $R^7$ is independently selected from the group consisting of H, halogen, optionally substituted alkyl, optionally substituted cycloalkyl, —OR, and —$N(R)_2$.

In some embodiments of a compound of Formula (I'), X is one of the following moieties: O, S, SO, or $SO_2$. In some embodiments, X is O. In some embodiments, X is S, SO, or SO$_2$. In some embodiments, X is S. In some embodiments, X is NR. In some embodiments, X is NH.

In some embodiments of a compound of Formula (I'), Y is selected from the group consisting of an optionally substituted alkyl, an optionally substituted alkenyl, an optionally substituted aryl, an optionally substituted heteroaryl, an optionally substituted C$_3$-C$_{10}$ cycloalkyl, and an optionally substituted non-aromatic heterocycle (containing one or more O, S, SO, SO$_2$, B, N, or NR). In some embodiments, Y is selected from:

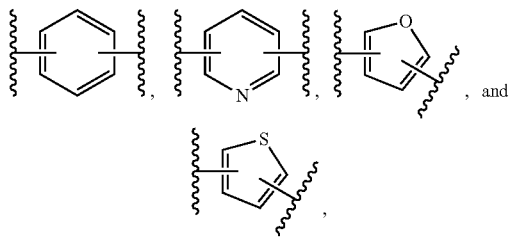

each of which may be optionally substituted. In some embodiments, Y is

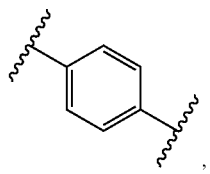 [SMILES: *c1ccc(*)cc1]

which may be optionally substituted, for example the phenylene may be substituted alkyl or cycloalkyl, halogen, —NR$_2$, —SF$_5$ and —OR. In some embodiments, the phenylene is substituted by methyl or perfluoromethyl. In some embodiments, the substitution is at a position ortho to the alkyne. Other examples within these embodiments, include phenylene moieties substituted by one or more fluoro moiety. For example, the phenylene moieties may be

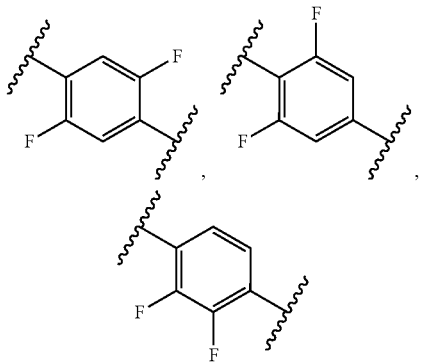

or further substituted variants thereof, e.g.,

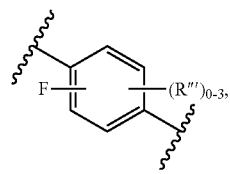

where R''' is a halogen (e.g., F, Cl, or Br), nitrile, a C$_1$-C$_6$ alkyl, or O—C$_1$-C$_6$ alkyl. In some embodiments, the phenylene is di-substituted, for example,

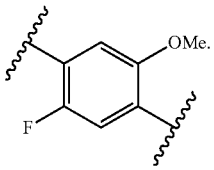 [SMILES: *c1cc(OC)c(*)cc1F]

In some embodiments, Y is phenylene optionally substituted with C$_1$-C$_6$ alkyl, C$_1$-C$_6$ haloalkyl, halogen, C$_1$-C$_6$ alkoxy, nitrile, or a combination of two or more thereof.

In some embodiments, Y is cyclobutane, cyclobutene, propellane (such as, but not limited to, [1.1.1.0$^{1,3}$] propellane), cubane, or

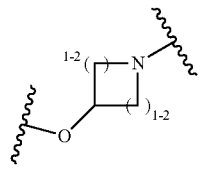

In Formula (I'), Z is O, SO$_{0-2}$, NR, C(R$^7$)$_2$, alkenyl or alkynyl. In some embodiments, Z is selected from O, S or C(R$^7$)$_2$, where R$^7$ is independently H, halogen, optionally substituted alkyl, optionally substituted cycloalkyl, or —N(R)$_2$. In some embodiments, R or R$^7$ is H. In some embodiments, Z is S.

In Formula (I'), R$^5$ is H, nitrile, an optionally substituted aryl, an optionally substituted heterocycle, optionally substituted C$_1$-C$_6$ alkyl, optionally substituted C$_3$-C$_9$ cycloalkyl, or

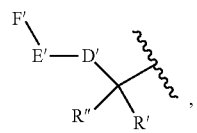

where R' and R'' are each independently selected from the group consisting of H, optionally substituted alkyl, —OR, halogen (e.g., F, Cl, Br, or I), —N(R)$_2$, optionally substituted cycloalkyl, and optionally substituted heterocycle;
or R' and R'' may together form an optionally substituted 3- to 6-membered cycloalkyl or optionally substituted 3- to 6-membered heterocycle;
D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;
E' is selected from a bond, an optionally substituted C$_1$-C$_6$ alkyl, optionally substituted C$_1$-C$_6$ alkenyl, and optionally substituted cycloalkyl; and
F' is selected from H, an optionally substituted cycloalkyl, an optionally substituted non-aromatic heterocycle, an optionally substituted aryl, and an optionally substituted heteroaryl.

When R$^5$ is an optionally substituted aryl, the moiety may be, e.g., a phenyl that is unsubstituted or substituted. In some embodiments, the phenyl may be substituted with one or more of alkyl, —OR, —CN, —CO$_2$R, halogen, —SR, —SOR, —SO$_2$R, —SF$_5$ and —NR$_2$.

When $R^5$ is an optionally substituted heterocycle, the moiety may be, e.g., morpholine or pyridine, optionally substituted with one or more alkyl, —OR, —CN, —CO$_2$R, halogen, —SR, —SOR, —SO$_2$R, —SF$_5$ or —NR$_2$.

In some embodiments, $R^5$ is $C_1$-$C_6$ alkyl optional substituted with alkoxy, hydroxy, amino, heterocyclyl, cycloalkyl, aryl, heteroaryl, or a combination of two or more thereof. In some embodiments, $R^5$ is H.

In some embodiments of a compound of Formula (I'), when $R^5$ is:

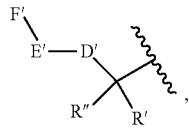

D', E' and F' may be defined as follows:

D' may be selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—; E' may be selected from the group consisting of a bond, an optionally substituted $C_1$-$C_6$ alkyl, optionally substituted $C_1$-$C_6$ alkenyl, and optionally substituted cycloalkyl; and F' may be selected from the group consisting of H, halogen, an optionally substituted cycloalkyl, an optionally substituted non-aromatic heterocycle, an optionally substituted aryl, and an optionally substituted heteroaryl.

D' is selected from the group consisting of —O—, —NR—, —OCONR—, —OCO—, —NRSO$_2$—, —NRCO—, —NRSO$_2$NR—, —NRCOO—, —NRCONR—, or —NRC(NR)NR—, where R is defined previously. In some embodiments, D' may be selected from the group consisting of O, NH, OCONH, OCO, NHSO$_2$, NHCO, NHSO$_2$NH, NHCOO, and NHCONH.

E' may be a bond or an optionally substituted $C_1$-$C_6$ alkyl or cycloalkyl. In some embodiments, E' is an optionally substituted $C_1$-$C_6$ alkyl. In some embodiments, E' is an optionally substituted $C_1$-$C_6$ alkyl and F' is H. In some embodiments, E' is $C_1$-$C_6$ alkyl substituted with a $C_3$-$C_7$ spirocycle. In some embodiments, E' is an optionally substituted $C_3$-$C_6$ cycloalkyl, (e.g., optionally substituted with alkyl, halogen, or —OR). In some embodiments the cycloalkyl is specifically selected from, e.g., one of the following: cyclopropyl, cyclobutyl, cyclopentyl, and cyclohexyl, each of which may be optionally substituted.

F' may be selected from the group consisting of H, an optionally substituted cycloalkyl, an optionally substituted non-aromatic heterocycle, an optionally substituted aryl, and an optionally substituted heteroaryl. In some embodiments, F' is an optionally substituted cycloalkyl, an optionally substituted non-aromatic heterocycle, an optionally substituted aryl, or an optionally substituted heteroaryl, each of which is described below in further detail. In some embodiments, F' is substituted with one or more alkyl, perfluoroalkyl (e.g., CF$_3$), —OR, —CN, —CO$_2$R, halogen, —SR, —SOR, —SO$_2$R, —SF$_5$ or —NR$_2$. In other embodiments, F' is not substituted.

In some embodiments, F' is an optionally substituted cycloalkyl. For example, F' may be a $C_3$-$C_6$ cycloalkyl, optionally substituted with alkyl, halogen, or —OR. In some embodiments, the cycloalkyl is specifically selected from, e.g., one of the following: cyclopropyl, cyclobutyl, cyclopentyl, and cyclohexyl, each of which may be optionally substituted. In some embodiments, the cycloalkyl is specifically selected from, e.g., one of the following: cyclopropyl, cyclobutyl, cyclopentyl, cyclohexyl, and propellane, each of which may be optionally substituted. In some embodiments, E' is a bond and F' is an optionally substituted cycloalkyl. In some embodiments, E' is optionally substituted $C_1$-$C_6$ alkyl and F' is an optionally substituted cycloalkyl.

In some embodiments, F' is an optionally substituted heterocycle. For example, F' may be a 4-6 membered non-aromatic heterocycle, optionally substituted with alkyl, halogen, or OR. In some embodiments, the heterocycle contains one or more heteroatom selected from: O, S, SO, SO$_2$, B, N, and NR. Particular embodiments include, e.g., morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, E' is a bond and F' is an optionally substituted non-aromatic heterocycle. In some embodiments, E' is optionally substituted $C_1$-$C_6$ alkyl and F' is an optionally substituted non-aromatic heterocycle.

In some embodiments, F' is an optionally substituted aryl. For example, F' may be a $C_6$-$C_{10}$ aryl, e.g., a phenyl, that is optionally substituted, e.g., with one or more of alkyl, perfluoroalkyl (e.g., CF$_3$), —OR, —CN, —CO$_2$R, halogen, —SR, —SOR, —SO$_2$R, —SF$_5$ or —NR$_2$. In some embodiments, E' is a bond and F' is an optionally substituted aryl. In some embodiments, E' is optionally substituted $C_1$-$C_6$ alkyl and F' is an optionally substituted aryl.

In some embodiments, F' is an optionally substituted heteroaryl. For example, F' may be a 5-6 membered heteroaryl, optionally substituted with alkyl, halogen, or OR. In some embodiments, the heteroaryl contains one or more heteroatom selected from O, S, SO, N, and NR. Particular embodiments include, e.g., alkyl-triazole, tetrazole, imidazole, and isoxazole. In some embodiments, E' is a bond and F' is an optionally substituted heteroaryl. In some embodiments, E' is optionally substituted $C_1$-$C_6$ alkyl and F' is an optionally substituted heteroaryl.

In some embodiments of a compound of Formula (I'), when $R^5$ is:

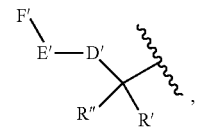

R' and R" may each independently selected from the group consisting of H, optionally substituted alkyl, —OR, halogen (e.g., F, Cl, Br, I), —N(R)$_2$, optionally substituted cycloalkyl, and optionally substituted heterocycle. In some embodiments, R' and R" are each H. In other embodiments, at least one of R' and R" is optionally substituted alkyl and any remaining R' or R" is H. In some embodiments, the optionally substituted alkyl is a $C_1$-$C_6$ alkyl or $C_1$-$C_6$ perfluoroalkyl. In some embodiments, the optionally substituted alkyl is methyl. In some embodiments, R' and R" are each independently optionally substituted $C_1$-$C_6$ alkyl.

Alternatively, R' and R" together may form a 3- to 6-membered cycloalkyl or heterocycle that is optionally substituted. In some embodiments, the 3- to 6-membered cycloalkyl or heterocycle is substituted by one or more $R^7$, as defined previously. In additional embodiments, R' and R" form a cyclopropyl, cyclobutyl, cyclopentyl, or cyclohexyl. In other embodiments, R' and R" form an oxetane. In some embodiments, R' and R" form an optionally substituted azetidine, oxetane, pyrrolidone or piperidine. In some embodiments, the nitrogen of the azetidine, pyrrolidone or piperidine may be substituted with R, SO$_2$R, COR, SO$_2$NR$_2$, CONR$_2$ and COOR. In some embodiments, when R' and R" form a ring, e.g., an optionally substituted cyclopropyl, cyclobutyl, cyclopentyl, or cyclohexyl, azetidine, oxetane, pyrrolidone or piperidine, then D'-E'-F' together form an —OH (i.e., D' is —O—, E' is a bond and F' is H).

In some embodiments of a compound of Formula (I'), R$^1$ is an optionally substituted phenyl or an optionally substituted 5- or 6-membered heteroaryl. For example, in some embodiments, R$^1$ is optionally substituted phenyl or optionally substituted pyridine. In some embodiments, R$^1$ is an unsubstituted phenyl or an unsubstituted pyridine. In some embodiments, R$^1$ is a pyridine. In some embodiments the pyridine is attached at the 2 position, the 3 position or the 4 position. In some embodiments the pyridine is attached at the 3 position. In some embodiments, R$^1$ is optionally substituted non-aromatic heterocyclic.

In some embodiments of a compound of Formula (I'), R$^2$ and R$^3$ are independently an optionally substituted C$_{1-9}$ cyclic, optionally substituted C$_{3-9}$ heterocyclic, or halogen, or R$^2$ and R$^3$ together form an optionally substituted C$_{3-9}$ cyclic or optionally substituted 3- to 9-membered heterocyclic ring. In some embodiments, R$^2$ is a C$_1$-C$_6$ alkyl, a C$_3$-C$_{10}$ cycloalkyl (including cycloalkenyl), or a heterocycle, each of which maybe optionally substituted.

In some embodiments, R$^2$ and R$^3$ together form an optionally substituted C$_{3-9}$ cyclic or optionally substituted 3- to 9-membered heterocyclic ring, for example, a C$_3$-C$_{10}$ cycloalkyl (including cycloalkenyl), or a heterocycle, each of which maybe optionally substituted. Exemplary individual embodiments when R$^2$ and R$^3$ together form an optionally substituted C$_{3-9}$ cyclic or optionally substituted 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

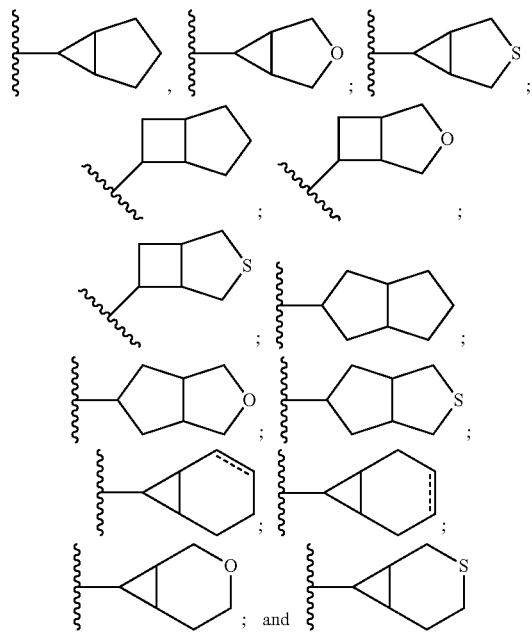

where one or more of the dashed bonds may optionally be a double bond and ⁝ indicates attachment to Z.

In some embodiments, one or more hydrogens in R$^2$ or R$^3$, or in both R$^2$ and R$^3$ are replaced with deuterium. In some embodiments, R$^2$ and R$^3$ form a perdeuterated cycloalkyl ring. In some embodiments, R$^2$ and R$^3$ form a perdeuterated cyclopentane

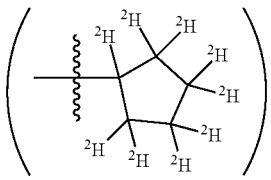

and ⁝
indicates attachment to Z. In some embodiments,

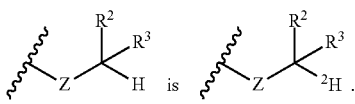

In some embodiments, compounds of the present disclosure include those represented by the following Formula (II):

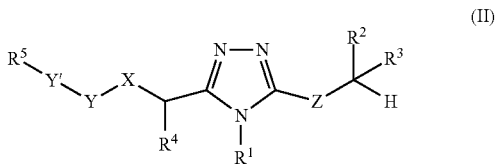

or a pharmaceutically acceptable salt, solvate or prodrug thereof, wherein:
X is O, SO$_{0-2}$, or NR;
Y is optionally substituted alkyl, optionally substituted alkenyl, alkynyl, optionally substituted aryl, optionally substituted heteroaryl, optionally substituted cycloalkyl, or optionally substituted non-aromatic heterocyclic;
Y' is alkynyl, optionally substituted heteroaryl, optionally substituted cycloalkyl, or optionally substituted non-aromatic heterocyclic;
R$^2$ and R$^3$ are independently optionally substituted C$_{1-6}$ alkyl, optionally substituted C$_{1-9}$ cyclic, optionally substituted C$_{3-9}$ heterocyclic, or halogen, or R$^2$ and R$^3$ together form an optionally substituted C$_{3-9}$ cyclic or optionally substituted 3- to 9-membered heterocyclic ring; and
the remaining variables have the same values as for Formula (I').

In some embodiments of a compound of Formula (II), X is one of the following moieties: O, S, SO, or SO$_2$. In some embodiments, X is O. In some embodiments, X is S, SO, or SO$_2$. In some embodiments, X is S. In some embodiments, X is NR. In some embodiments, X is NH.

In some embodiments of a compound of Formula (II), Y' is selected from the group consisting of an alkyne, an optionally substituted heteroaryl, an optionally substituted C$_3$-C$_{10}$ cycloalkyl, and an optionally substituted non-aromatic heterocycle (containing one or more O, S, SO, SO$_2$, N, or NR). In some embodiments, Y' is selected from the group consisting of:

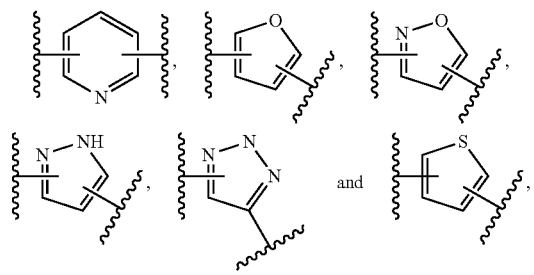

each of which may be optionally substituted. In some embodiments, Y' is cyclobutane, cyclobutene, propellane (such as, but not limited to, [1.1.1.0$^{1,3}$] propellane), cubane, or

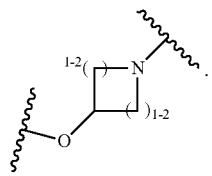

In some embodiments, Y is selected from the group consisting of an optionally substituted alkyl, an optionally substituted alkenyl, an optionally substituted aryl, an optionally substituted heteroaryl, an optionally substituted $C_3$-$C_{10}$ cycloalkyl, and an optionally substituted non-aromatic heterocycle (containing one or more O, S, SO, $SO_2$, B, N, or NR). In some embodiments, Y is selected from:

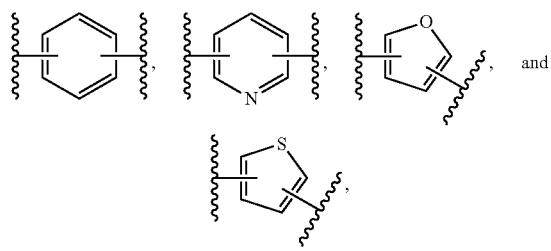

each of which may be optionally substituted. In some embodiments, Y is

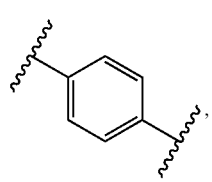 [SMILES: *c1ccc(*)cc1]

which may be optionally substituted, for example the phenylene may be substituted alkyl or cycloalkyl, halogen, —$NR_2$, —$SF_5$ and —OR. In some embodiments, the phenylene is substituted by methyl or perfluoromethyl. In some embodiments, the substitution is at a position ortho to the alkyne. Other examples within these embodiments, include phenylene moieties substituted by one or more fluoro moiety. For example, the phenylene moieties may be

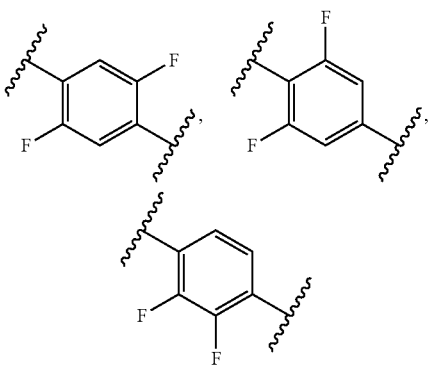

or further substituted variants thereof, e.g.,

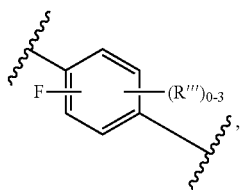

where R''' is a halogen (e.g., F, Cl, or Br), nitrile, a $C_1$-$C_6$ alkyl, or O—$C_1$-$C_6$ alkyl. In some embodiments, the phenylene is di-substituted, for example,

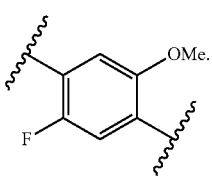 [SMILES: *c1cc(OC)c(*)cc1F]

In some embodiments, Y is phenylene optionally substituted with $C_1$-$C_6$ alkyl, $C_1$-$C_6$ haloalkyl, halogen, $C_1$-$C_6$ alkoxy, nitrile, or a combination of two or more thereof.

In some embodiments, Y is cyclobutane, cyclobutene, propellane (such as, but not limited to, [1.1.1.0$^{1,3}$] propellane), cubane, or

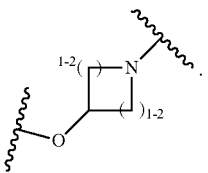

In Formula (II), Z is O, $SO_{0-2}$, NR, $C(R^7)_2$, alkenyl or alkynyl. In some embodiments, Z is selected from the group consisting of O, S, and $C(R^7)_2$, where $R^7$ is independently H, halogen, optionally substituted alkyl, optionally substituted cycloalkyl, or —$N(R)_2$. In some embodiments, R or $R^7$ is H. In some embodiments, Z is S.

In Formula (II), $R^5$ is H, nitrile, an optionally substituted aryl, an optionally substituted heterocycle, optionally substituted $C_1$-$C_6$ alkyl, optionally substituted $C_3$-$C_9$ cycloalkyl, or

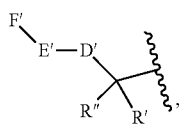

where R' and R" are each independently selected from the group consisting of H, optionally substituted alkyl, —OR, halogen (e.g., F, Cl, Br, or I), —N(R)$_2$, optionally substituted cycloalkyl, and optionally substituted heterocycle;

or R' and R" may together form an optionally substituted 3- to 6-membered cycloalkyl or optionally substituted 3- to 6-membered heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted C$_1$-C$_6$ alkyl, optionally substituted C$_1$-C$_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl.

When R$^5$ is an optionally substituted aryl, the moiety may be, e.g., a phenyl that is unsubstituted or substituted. In some embodiments, the phenyl may be substituted with one or more of alkyl, —OR, —CN, —CO$_2$R, halogen, —SR, —SOR, —SO$_2$R, —SF$_5$ and —NR$_2$.

When R$^5$ is an optionally substituted heterocycle, the moiety may be, e.g., morpholine or pyridine, optionally substituted with one or more alkyl, —OR, —CN, —CO$_2$R, halogen, —SR, —SOR, —SO$_2$R, —SF$_5$ or —NR$_2$.

In some embodiments, R$^5$ is C$_1$-C$_6$ alkyl optional substituted with alkoxy, hydroxy, amino, heterocyclyl, cycloalkyl, aryl, heteroaryl, or a combination of two or more thereof. In some embodiments, R$^5$ is H.

In some embodiments of a compound of Formula (II), when R$^5$ is:

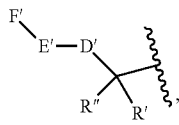

D', E' and F' may be defined as follows:

D' may be selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—; E' may be selected from the group consisting of a bond, an optionally substituted C$_1$-C$_6$ alkyl, optionally substituted C$_1$-C$_6$ alkenyl, and optionally substituted cycloalkyl; and F' may be selected from the group consisting of H, halogen, an optionally substituted cycloalkyl, an optionally substituted non-aromatic heterocycle, an optionally substituted aryl, and an optionally substituted heteroaryl.

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—, where R is defined previously. In some embodiments, D' may be selected from the group consisting of O, NH, OCONH, OCO, NHSO$_2$, NHCO, NHSO$_2$NH, NHCOO, and NHCONH.

E' may be a bond or an optionally substituted C$_1$-C$_6$ alkyl or cycloalkyl. In some embodiments, E' is an optionally substituted C$_1$-C$_6$ alkyl. In some embodiments, E' is an optionally substituted C$_1$-C$_6$ alkyl and F' is H. In some embodiments, E' is C$_1$-C$_6$ alkyl substituted with a C$_3$-C$_7$ spirocycle. In some embodiments, E' is an optionally substituted C$_3$-C$_6$ cycloalkyl, (e.g., optionally substituted with alkyl, halogen, or —OR). In some embodiments, the cycloalkyl is specifically selected from, e.g., one of the following: cyclopropyl, cyclobutyl, cyclopentyl, and cyclohexyl, each of which may be optionally substituted.

F' may be selected from the group consisting of H, an optionally substituted cycloalkyl, an optionally substituted non-aromatic heterocycle, an optionally substituted aryl, and an optionally substituted heteroaryl. In some embodiments, F' is an optionally substituted cycloalkyl, an optionally substituted non-aromatic heterocycle, an optionally substituted aryl, or an optionally substituted heteroaryl, each of which is described below in further detail. In some embodiments, F' is substituted with one or more alkyl, perfluoroalkyl (e.g., CF$_3$), —OR, —CN, —CO$_2$R, halogen, —SR, —SOR, —SO$_2$R, —SF$_5$ or —NR$_2$. In other embodiments, F' is not substituted.

In some embodiments, F' is an optionally substituted cycloalkyl. For example, F' may be a C$_3$-C$_6$ cycloalkyl, optionally substituted with alkyl, halogen, or —OR. In some embodiments, the cycloalkyl is specifically selected from, e.g., one of the following: cyclopropyl, cyclobutyl, cyclopentyl, and cyclohexyl, each of which may be optionally substituted. In some embodiments, the cycloalkyl is specifically selected from, e.g., one of the following: cyclopropyl, cyclobutyl, cyclopentyl, cyclohexyl, and propellane, each of which may be optionally substituted. In some embodiments, E' is a bond and F' is an optionally substituted cycloalkyl. In some embodiments, E' is optionally substituted C$_1$-C$_6$ alkyl and F' is an optionally substituted cycloalkyl.

In some embodiments, F' is an optionally substituted heterocycle. For example, F' may be a 4-6 membered non-aromatic heterocycle, optionally substituted with alkyl, halogen, or OR. In some embodiments, the heterocycle contains one or more heteroatom selected from: O, S, SO, SO$_2$, B, N, and NR. Particular embodiments include, e.g., morpholine, azetidine, alkyl-piperidine, alkyl-piperazine, alkyl-diazepane, thiomorpholine 1,1-dioxide, isoindoline-1,3-dione, tetrahydropyran, and pyrrolidone. In some embodiments, E' is a bond and F' is an optionally substituted non-aromatic heterocycle. In some embodiments, E' is optionally substituted C$_1$-C$_6$ alkyl and F' is an optionally substituted non-aromatic heterocycle.

In some embodiments, F' is an optionally substituted aryl. For example, F' may be a C$_6$-C$_{10}$ aryl, e.g., a phenyl, that is optionally substituted, e.g., with one or more of alkyl, perfluoroalkyl (e.g., CF$_3$), —OR, —CN, —CO$_2$R, halogen, —SR, —SOR, —SO$_2$R, —SF$_5$ or —NR$_2$. In some embodiments, E' is a bond and F' is an optionally substituted aryl. In some embodiments, E' is optionally substituted C$_1$-C$_6$ alkyl and F' is an optionally substituted aryl.

In some embodiments, F' is an optionally substituted heteroaryl. For example, F' may be a 5-6 membered heteroaryl, optionally substituted with alkyl, halogen, or OR. In some embodiments, the heteroaryl contains one or more heteroatom selected from O, S, SO, N, and NR. Particular embodiments include, e.g., alkyl-triazole, tetrazole, imidazole, and isoxazole. In some embodiments, E' is a bond and F' is an optionally substituted heteroaryl. In some embodiments, E' is optionally substituted $C_1$-$C_6$ alkyl and F' is an optionally substituted heteroaryl.

In some embodiments of a compound of Formula (II), when $R^5$ is:

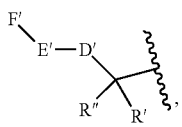

R' and R" may each independently selected from the group consisting of H, optionally substituted alkyl, —OR, halogen (e.g., F, Cl, Br, I), —N(R)$_2$, optionally substituted cycloalkyl, and optionally substituted heterocycle. In some embodiments, R' and R" are each H. In other embodiments, at least one of R' and R" is optionally substituted alkyl and any remaining R' or R" is H. In some embodiments, the optionally substituted alkyl is a $C_1$-$C_6$ alkyl or $C_1$-$C_6$ perfluoroalkyl. In some embodiments, the optionally substituted alkyl is methyl. In some embodiments, R' and R" are each independently optionally substituted $C_1$-$C_6$ alkyl.

Alternatively, R' and R" together may form a 3- to 6-membered cycloalkyl or heterocycle that is optionally substituted. In some embodiments, the 3- to 6-membered cycloalkyl or heterocycle is substituted by one or more $R^7$, as defined previously. In additional embodiments, R' and R" form a cyclopropyl, cyclobutyl, cyclopentyl, or cyclohexyl. In other embodiments, R' and R" form an oxetane. In some embodiments, R' and R" form an optionally substituted azetidine, oxetane, pyrrolidone or piperidine. In some embodiments, the nitrogen of the azetidine, pyrrolidone or piperidine may be substituted with R, SO$_2$R, COR, SO$_2$NR$_2$, CONR$_2$ or COOR. In some embodiments, when R' and R" form a ring, e.g., an optionally substituted cyclopropyl, cyclobutyl, cyclopentyl, or cyclohexyl, azetidine, oxetane, pyrrolidone or piperidine, then D'-E'-F' together form an —OH (i.e., D' is —O—, E' is a bond and F' is H).

In some embodiments of a compound of Formula (II), $R^1$ is an optionally substituted phenyl or an optionally substituted 5- or 6-membered heteroaryl. For example, in some embodiments, $R^1$ is optionally substituted phenyl or optionally substituted pyridine. In some embodiments, $R^1$ is an unsubstituted phenyl or an unsubstituted pyridine. In some embodiments, $R^1$ is a pyridine. In some embodiments the pyridine is attached at the 2 position, the 3 position or the 4 position. In some embodiments the pyridine is attached at the 3 position. In some embodiments, $R^1$ is optionally substituted non-aromatic heterocyclic.

In some embodiments of a compound of Formula (II), $R^2$ and $R^3$ are independently an optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring. In some embodiments, $R^2$ is a $C_1$-$C_6$ alkyl, a $C_3$-$C_{10}$ cycloalkyl (including cycloalkenyl), or a heterocycle, each of which maybe optionally substituted. In some embodiments, $R^2$ is optionally substituted $C_{1-6}$ alkyl. In some embodiments, $R^2$ is $C_{1-6}$ alkyl substituted with a $C_{3-9}$ heterocyclic group, a $C_{1-9}$ cyclic group, or one or more alkenes.

In some embodiments, $R^2$ and $R^3$ together form an optionally substituted $C_{3-9}$ cyclic or optionally substituted 3- to 9-membered heterocyclic ring, for example, a $C_3$-$C_{10}$ cycloalkyl (including cycloalkenyl), or a heterocycle, each of which maybe optionally substituted. Exemplary individual embodiments when $R^2$ and $R^3$ together form an optionally substituted $C_{3-9}$ cyclic or optionally substituted 3- to 9-membered heterocyclic ring, include cyclopropyl, cyclobutyl, cyclopentyl, cyclohexyl, cyclopentene, and cyclohexene, each of which may be optionally substituted, for example, by one or more deuterium or fluorine moiety. Other embodiments include bicyclic structures, such as:

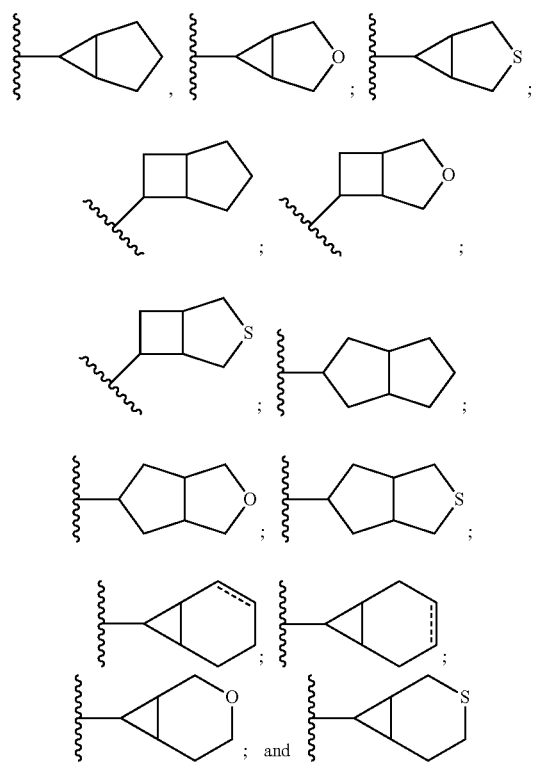

where one or more of the dashed bonds may optionally be a double bond and ⁝ indicates attachment to Z.

In some embodiments, one or more hydrogens in $R^2$ or $R^3$, or in both $R^2$ and $R^3$ are replaced with deuterium. In some embodiments, $R^2$ and $R^3$ form a perdeuterated cycloalkyl ring. In some embodiments, $R^2$ and $R^3$ form a perdeuterated cyclopentane

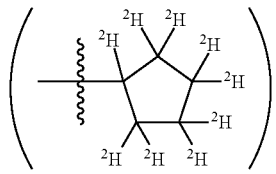

and ⁝ indicates attachment to Z. In some embodiments,

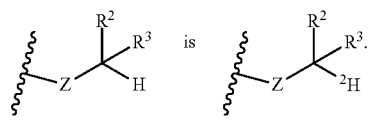

In some embodiments, the compounds of the present disclosure are selected from the compounds of Table I or a pharmaceutically acceptable salt or prodrug thereof.

TABLE I

[Structure: R⁵—≡—Y—X—C(R⁴)—(triazole: N—N, N with R¹)—Z—C(R²)(R³)H]

| R⁵ | Y | X | R⁴ | R¹ | Z | R² R³ |
|---|---|---|---|---|---|---|
| H | alkyl or alkenyl | O | H | optionally substituted 5- or 6-membered heteroaryl | S | a C₃₋₉ cyclic or C₃₋₉ heterocyclic ring |
| nitrile | alkyl or alkenyl | O | H | optionally substituted 5- or 6-membered heteroaryl | S | a C₃₋₉ cyclic or C₃₋₉ heterocyclic ring |
| optionally substituted aryl | alkyl or alkenyl | O | H | optionally substituted 5- or 6-membered heteroaryl | S | a C₃₋₉ cyclic or C₃₋₉ heterocyclic ring |
| optionally substituted heterocycle | alkyl or alkenyl | O | H | optionally substituted 5- or 6-membered heteroaryl | S | a C₃₋₉ cyclic or C₃₋₉ heterocyclic ring |
| optionally substituted C₁-C₆ alkyl | alkyl or alkenyl | O | H | optionally substituted 5- or 6-membered heteroaryl | S | a C₃₋₉ cyclic or C₃₋₉ heterocyclic ring |
| optionally substituted C₃-C₉ cycloalkyl | alkyl or alkenyl | O | H | optionally substituted 5- or 6-membered heteroaryl | S | a C₃₋₉ cyclic or C₃₋₉ heterocyclic ring |
| [F, E—D, R″, R′ substituent group] | alkyl or alkenyl | O | H | optionally substituted 5- or 6-membered heteroaryl | S | a C₃₋₉ cyclic or C₃₋₉ heterocyclic ring |
| H | optionally substituted aryl | O | H | optionally substituted 5- or 6-membered heteroaryl | S | an optionally substituted C₃₋₉ cyclic or optionally substituted C₃₋₉ heterocyclic ring |
| nitrile | optionally substituted aryl | O | H | optionally substituted 5- or 6-membered heteroaryl | S | an optionally substituted C₃₋₉ cyclic or optionally substituted C₃₋₉ heterocyclic ring |
| optionally substituted aryl | optionally substituted aryl | O | H | optionally substituted 5- or 6-membered heteroaryl | S | an optionally substituted C₃₋₉ cyclic or optionally substituted C₃₋₉ heterocyclic ring |
| optionally substituted heterocycle | optionally substituted aryl | O | H | optionally substituted 5- or 6-membered heteroaryl | S | an optionally substituted C₃₋₉ cyclic or optionally substituted C₃₋₉ heterocyclic ring |
| optionally substituted C₁-C₆ alkyl | optionally substituted aryl | O | H | optionally substituted 5- or 6-membered heteroaryl | S | an optionally substituted C₃₋₉ cyclic or optionally substituted C₃₋₉ heterocyclic ring |
| optionally substituted C₃-C₉ cycloalkyl | optionally substituted aryl | O | H | optionally substituted 5- or 6-membered heteroaryl | S | an optionally substituted C₃₋₉ cyclic or optionally substituted C₃₋₉ heterocyclic ring |
| [F, E—D, R″, R′ substituent group] | optionally substituted aryl | O | H | optionally substituted 5- or 6-membered heteroaryl | S | an optionally substituted C₃₋₉ cyclic or optionally substituted C₃₋₉ heterocyclic ring |

In some embodiments, when $R^5$ is

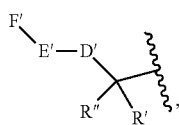

the moiety can be, for example, one of the following of Table II. In some embodiments, one or more of the moieties in Table II are substituted (e.g., E' is an optionally substituted $C_1$-$C_6$ alkyl).

TABLE II

| F' | E' | D' | R' | R" |
|---|---|---|---|---|
| H | $C_1$-$C_6$ alkyl | —O— | H | H |
| H | $C_1$-$C_6$ alkyl | —NR— | H | H |
| H | $C_1$-$C_6$ alkyl | —OCONR— | H | H |
| H | $C_1$-$C_6$ alkyl | —OCO— | H | H |
| H | $C_1$-$C_6$ alkyl | —NRSO$_2$— | H | H |
| H | $C_1$-$C_6$ alkyl | —NRCO— | H | H |
| H | $C_1$-$C_6$ alkyl | —NRSO$_2$NR— | H | H |
| H | $C_1$-$C_6$ alkyl | —NRCOO— | H | H |
| H | $C_1$-$C_6$ alkyl | —NRCONR— | H | H |
| H | $C_1$-$C_6$ alkyl | —NRC(NR)NR— | H | H |
| optionally substituted cycloalkyl | $C_1$-$C_6$ alkyl | —O— | H | H |
| optionally substituted cycloalkyl | $C_1$-$C_6$ alkyl | —NR— | H | H |
| optionally substituted cycloalkyl | $C_1$-$C_6$ alkyl | —OCONR— | H | H |
| optionally substituted cycloalkyl | $C_1$-$C_6$ alkyl | —OCO— | H | H |
| optionally substituted cycloalkyl | $C_1$-$C_6$ alkyl | —NRSO$_2$— | H | H |
| optionally substituted cycloalkyl | $C_1$-$C_6$ alkyl | —NRCO— | H | H |
| optionally substituted cycloalkyl | $C_1$-$C_6$ alkyl | —NRSO$_2$NR— | H | H |
| optionally substituted cycloalkyl | $C_1$-$C_6$ alkyl | —NRCOO— | H | H |
| optionally substituted cycloalkyl | $C_1$-$C_6$ alkyl | —NRCONR— | H | H |
| optionally substituted cycloalkyl | $C_1$-$C_6$ alkyl | —NRC(NR)NR— | H | H |
| optionally substituted heterocycle | $C_1$-$C_6$ alkyl | —O— | H | H |
| optionally substituted heterocycle | $C_1$-$C_6$ alkyl | —NR— | H | H |
| optionally substituted heterocycle | $C_1$-$C_6$ alkyl | —OCONR— | H | H |
| optionally substituted heterocycle | $C_1$-$C_6$ alkyl | —OCO— | H | H |
| optionally substituted heterocycle | $C_1$-$C_6$ alkyl | —NRSO$_2$— | H | H |
| optionally substituted heterocycle | $C_1$-$C_6$ alkyl | —NRCO— | H | H |
| optionally substituted heterocycle | $C_1$-$C_6$ alkyl | —NRSO$_2$NR— | H | H |
| optionally substituted heterocycle | $C_1$-$C_6$ alkyl | —NRCOO— | H | H |
| optionally substituted heterocycle | $C_1$-$C_6$ alkyl | —NRCONR— | H | H |
| optionally substituted heterocycle | $C_1$-$C_6$ alkyl | —NRC(NR)NR— | H | H |
| optionally substituted aryl | $C_1$-$C_6$ alkyl | —O— | H | H |
| optionally substituted aryl | $C_1$-$C_6$ alkyl | —NR— | H | H |
| optionally substituted aryl | $C_1$-$C_6$ alkyl | —OCONR— | H | H |
| optionally substituted aryl | $C_1$-$C_6$ alkyl | —OCO— | H | H |
| optionally substituted aryl | $C_1$-$C_6$ alkyl | —NRSO$_2$— | H | H |
| optionally substituted aryl | $C_1$-$C_6$ alkyl | —NRCO— | H | H |
| optionally substituted aryl | $C_1$-$C_6$ alkyl | —NRSO$_2$NR— | H | H |
| optionally substituted aryl | $C_1$-$C_6$ alkyl | —NRCOO— | H | H |
| optionally substituted aryl | $C_1$-$C_6$ alkyl | —NRCONR— | H | H |
| optionally substituted aryl | $C_1$-$C_6$ alkyl | —NRC(NR)NR— | H | H |
| optionally substituted heteroaryl | $C_1$-$C_6$ alkyl | —O— | H | H |
| optionally substituted heteroaryl | $C_1$-$C_6$ alkyl | —NR— | H | H |
| optionally substituted heteroaryl | $C_1$-$C_6$ alkyl | —OCONR— | H | H |
| optionally substituted heteroaryl | $C_1$-$C_6$ alkyl | —OCO— | H | H |
| optionally substituted heteroaryl | $C_1$-$C_6$ alkyl | —NRSO$_2$— | H | H |
| optionally substituted heteroaryl | $C_1$-$C_6$ alkyl | —NRCO— | H | H |
| optionally substituted heteroaryl | $C_1$-$C_6$ alkyl | —NRSO$_2$NR— | H | H |
| optionally substituted heteroaryl | $C_1$-$C_6$ alkyl | —NRCOO— | H | H |
| optionally substituted heteroaryl | $C_1$-$C_6$ alkyl | —NRCONR— | H | H |
| optionally substituted heteroaryl | $C_1$-$C_6$ alkyl | —NRC(NR)NR— | H | H |
| optionally substituted cycloalkyl | bond | —O— | H | H |
| optionally substituted cycloalkyl | bond | —NR— | H | H |
| optionally substituted cycloalkyl | bond | —OCONR— | H | H |
| optionally substituted cycloalkyl | bond | —OCO— | H | H |
| optionally substituted cycloalkyl | bond | —NRSO$_2$— | H | H |
| optionally substituted cycloalkyl | bond | —NRCO— | H | H |
| optionally substituted cycloalkyl | bond | —NRSO$_2$NR— | H | H |
| optionally substituted cycloalkyl | bond | —NRCOO— | H | H |
| optionally substituted cycloalkyl | bond | —NRCONR— | H | H |
| optionally substituted cycloalkyl | bond | —NRC(NR)NR— | H | H |
| optionally substituted heterocycle | bond | —NR— | H | H |
| optionally substituted heterocycle | bond | —OCONR— | H | H |
| optionally substituted heterocycle | bond | —OCO— | H | H |
| optionally substituted heterocycle | bond | —NRSO$_2$— | H | H |
| optionally substituted heterocycle | bond | —NRCO— | H | H |
| optionally substituted heterocycle | bond | —NRSO$_2$NR— | H | H |
| optionally substituted heterocycle | bond | —NRCOO— | H | H |
| optionally substituted heterocycle | bond | —NRCONR— | H | H |
| optionally substituted heterocycle | bond | —NRC(NR)NR— | H | H |
| optionally substituted aryl | bond | —NR— | H | H |
| optionally substituted aryl | bond | —OCONR— | H | H |
| optionally substituted aryl | bond | —OCO— | H | H |
| optionally substituted aryl | bond | —NRSO$_2$— | H | H |
| optionally substituted aryl | bond | —NRCO— | H | H |
| optionally substituted aryl | bond | —NRSO$_2$NR— | H | H |
| optionally substituted aryl | bond | —NRCOO— | H | H |
| optionally substituted aryl | bond | —NRCONR— | H | H |
| optionally substituted aryl | bond | —NRC(NR)NR— | H | H |
| optionally substituted heteroaryl | bond | —NR— | H | H |
| optionally substituted heteroaryl | bond | —OCONR— | H | H |
| optionally substituted heteroaryl | bond | —OCO— | H | H |
| optionally substituted heteroaryl | bond | —NRSO$_2$— | H | H |
| optionally substituted heteroaryl | bond | —NRCO— | H | H |
| optionally substituted heteroaryl | bond | —NRSO$_2$NR— | H | H |
| optionally substituted heteroaryl | bond | —NRCOO— | H | H |
| optionally substituted heteroaryl | bond | —NRCONR— | H | H |
| optionally substituted heteroaryl | bond | —NRC(NR)NR— | H | H |

In some embodiments, the compounds of the present disclosure are selected from the compounds of Table III (shown below) or a pharmaceutically acceptable salt or prodrug thereof. It should be noted that the moieties of the compounds of Table III fall within the scope of compounds of Formulae (I), (I'), or (II). The present disclosure includes embodiments where one or more of the variable moieties of Formulae (I), (I'), or (II) are represented by the equivalent moiety of one or more of the compounds of Table III without requiring the other specific moieties of the same compound of Table III.

Additional species within the scope of the disclosure are presented in Table III.

TABLE III

| No | Compound | Analytical Data; M + H (LC-HRMS) |
|---|---|---|
| 1 | | 529.2939 |
| 2 | | 391.1587 |
| 3 | | 513.2989 |
| 4 | | 432.1853 |
| 5 | | 416.1542 |

TABLE III-continued

| No | Compound | Analytical Data; M + H (LC-HRMS) |
|---|---|---|
| 6 | | 543.2733 |
| 7 | | 586.1944 |
| 8 | | 490.2270 |
| 9 | | 495.2212 |
| 10 | | 504.2426 |
| 11 | | 462.2322 |

TABLE III-continued
| No | Compound | Analytical Data; M + H (LC-HRMS) |
|---|---|---|
| 12 | 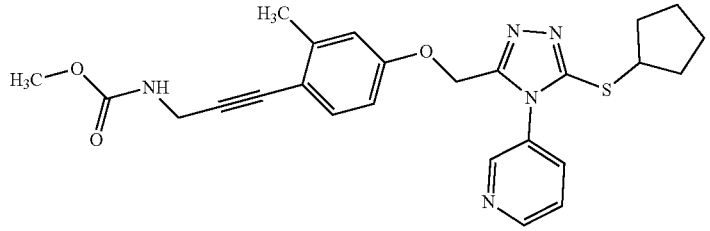 [SMILES: COC(=O)NCC#Cc1ccc(OCc2nnc(SC3CCCC3)n2-c2cccnc2)cc1C] | 478.1907 |
| 13 | 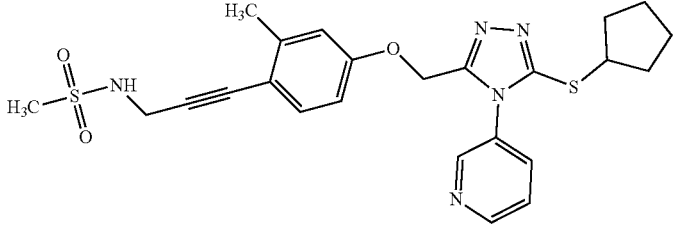 [SMILES: Cc1cc(OCc2nnc(SC3CCCC3)n2-c2cccnc2)ccc1C#CCNS(C)(=O)=O] | 498.1627 |
| 14 | 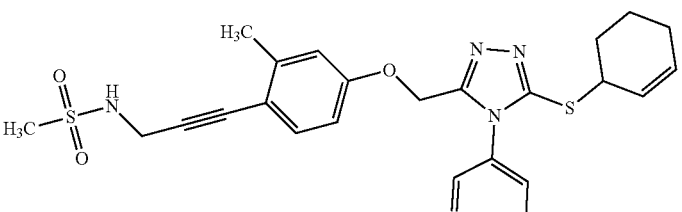 | 510.1628 |
| 15 | 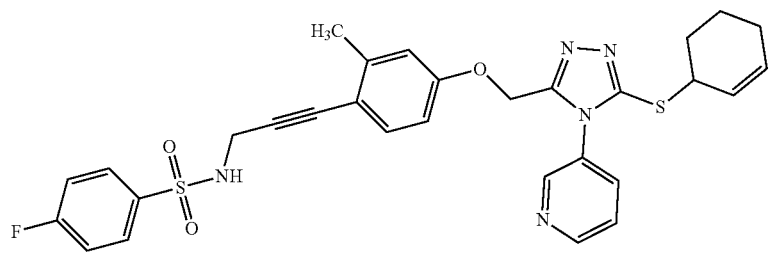 [SMILES: Cc1cc(OCc2nnc(SC3C=CCCC3)n2-c2cccnc2)ccc1C#CCNS(=O)(=O)c1ccc(F)cc1] | 590.1693 |
| 16 | 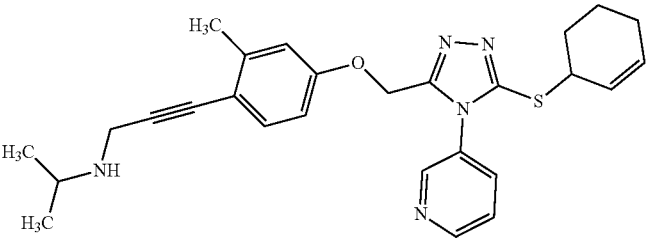 [SMILES: Cc1cc(OCc2nnc(SC3C=CCCC3)n2-c2cccnc2)ccc1C#CCNC(C)C] | 474.2327 |
| 17 | 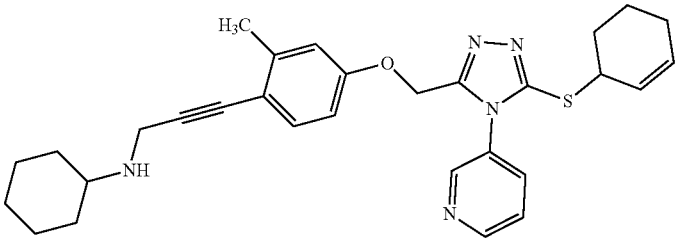 [SMILES: Cc1cc(OCc2nnc(SC3C=CCCC3)n2-c2cccnc2)ccc1C#CCNC1CCCCC1] | 514.2637 |

TABLE III-continued
| No | Compound | Analytical Data; M + H (LC-HRMS) |
|---|---|---|
| 18 | 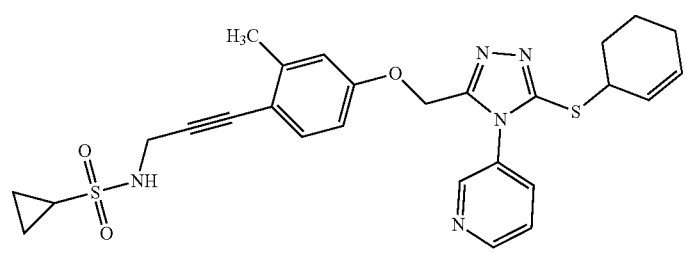 [SMILES: Cc1cc(OCc2nnc(SC3C=CCCC3)n2-c2cccnc2)ccc1C#CCNS(=O)(=O)C1CC1] | 536.1788 |
| 19 | 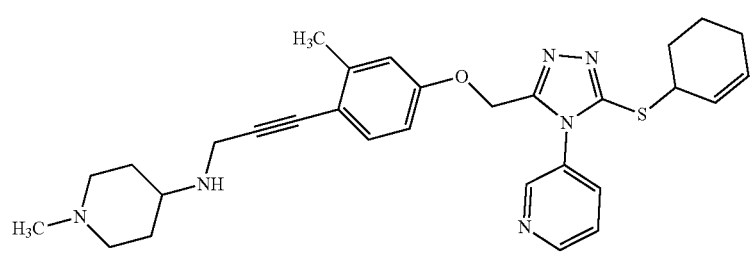 [SMILES: Cc1cc(OCc2nnc(SC3C=CCCC3)n2-c2cccnc2)ccc1C#CCNC1CCN(C)CC1] | 529.2745 |
| 20 | 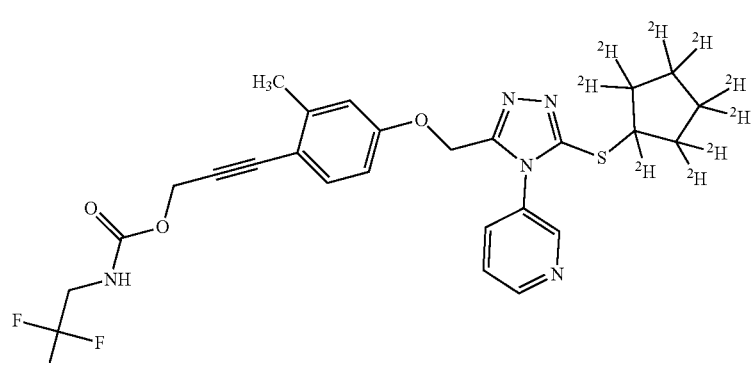 | 555.2343 |
| 21 | 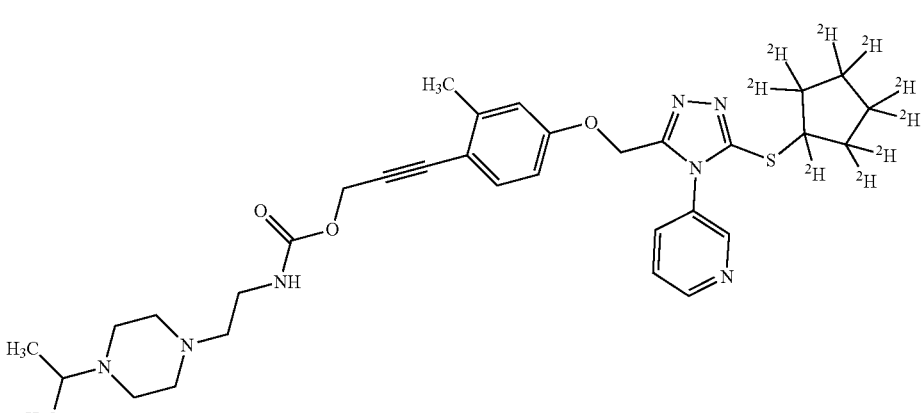 | 627.3783 |

TABLE III-continued
| No | Compound | Analytical Data; M + H (LC-HRMS) |
|---|---|---|
| 22 | 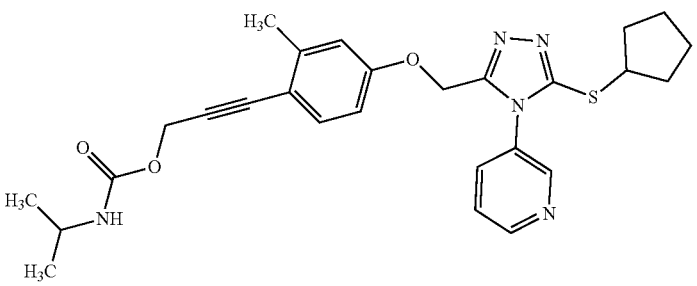 [SMILES: Cc1cc(OCc2nnc(SC3CCCC3)n2-c2cccnc2)ccc1C#CCOC(=O)NC(C)C] | 506.2220 |
| 23 | 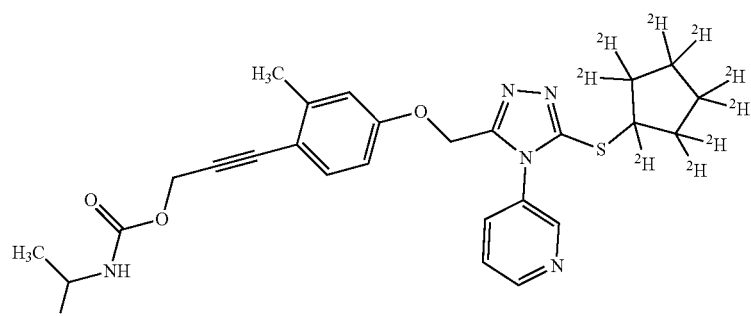 | 515.2785 |
| 24 | 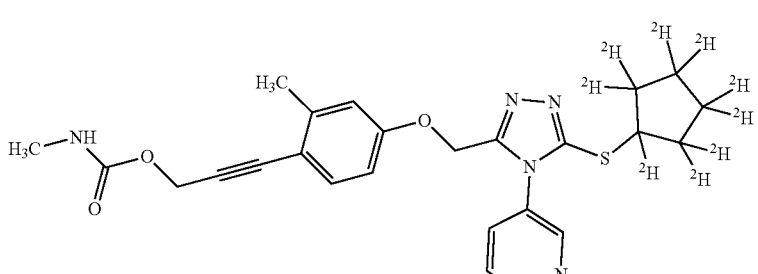 | 487.2470 |
| 25 | 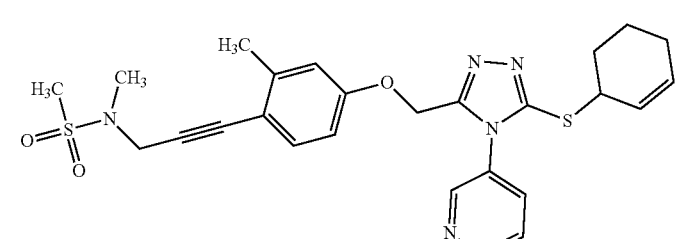 | 524.1787 |
| 26 | 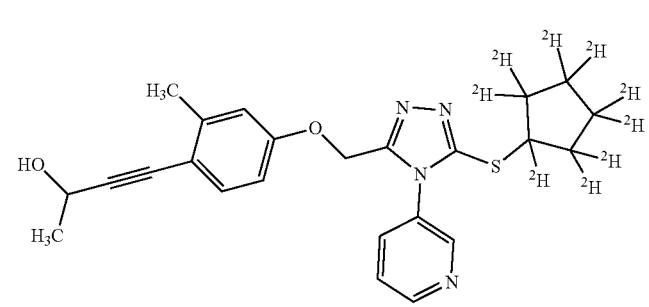 [SMILES: [2H]C1([2H])C([2H])([2H])C([2H])([2H])C([2H])(Sc2nnc(COc3ccc(C#CC(C)O)c(C)c3)n2-c2cccnc2)C1([2H])[2H]] | 444.2415 |

TABLE III-continued

| No | Compound | Analytical Data; M + H (LC-HRMS) |
|---|---|---|
| 27 | | 458.2569 |
| 28 | | 461.2007 |
| 29 | | 630.3221 |
| 30 | | 670.3534 |
| 31 | | 582.2955 |

TABLE III-continued

| No | Compound | Analytical Data; M + H (LC-HRMS) |
|---|---|---|
| 32 | | 641.3940 |
| 33 | | 539.1891 |
| 34 | | 475.1796 |
| 35 | | 568.2682 |
| 36 | | 444.2407 |

TABLE III-continued
| No | Compound | Analytical Data; M + H (LC-HRMS) |
|---|---|---|
| 37 | 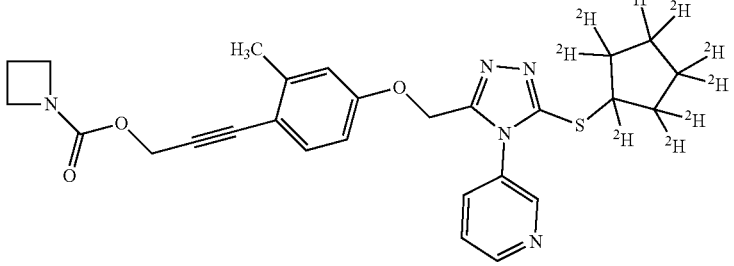 | 513.2626 |
| 38 | 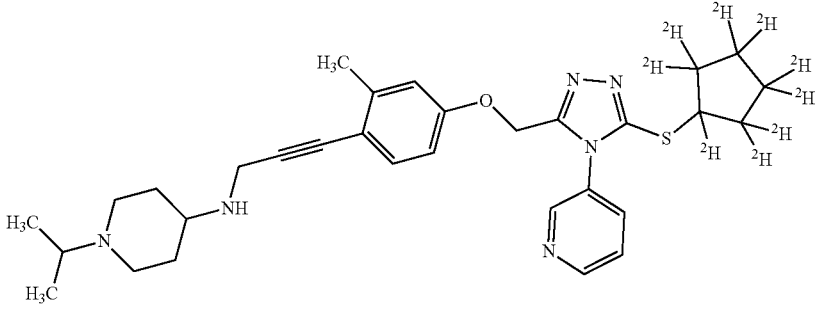 [SMILES: [2H]C1([2H])C([2H])([2H])C([2H])([2H])C([2H])(Sc2nnc(COc3ccc(C#CCNC4CCN(C(C)C)CC4)c(C)c3)n2-c2cccnc2)C1([2H])[2H]] | 554.3619 |
| 39 | 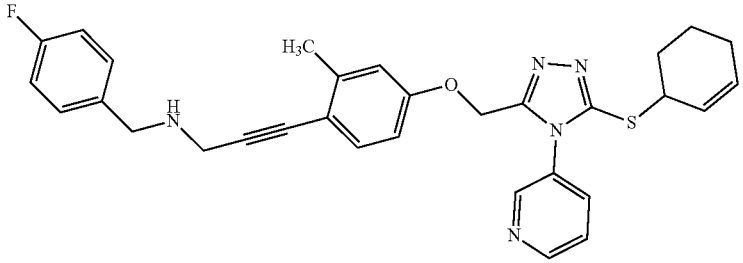 [SMILES: Cc1cc(OCc2nnc(SC3C=CCCC3)n2-c2cccnc2)ccc1C#CCNCc1ccc(F)cc1] | 540.2230 |
| 40 | 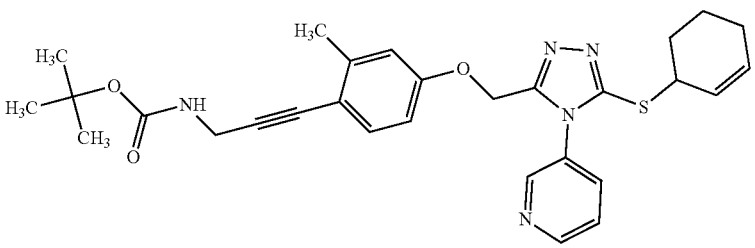 [SMILES: Cc1cc(OCc2nnc(SC3C=CCCC3)n2-c2cccnc2)ccc1C#CCNC(=O)OC(C)(C)C] | 532.2374 |
| 41 | 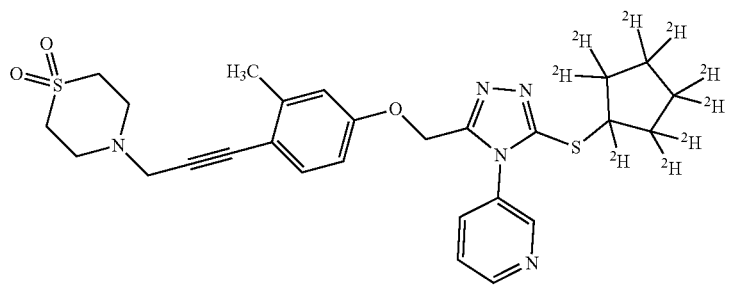 [SMILES: [2H]C1([2H])C([2H])([2H])C([2H])([2H])C([2H])(Sc2nnc(COc3ccc(C#CCN4CCS(=O)(=O)CC4)c(C)c3)n2-c2cccnc2)C1([2H])[2H]] | 547.2501 |

TABLE III-continued
| No | Compound | Analytical Data; M + H (LC-HRMS) |
|---|---|---|
| 42 | 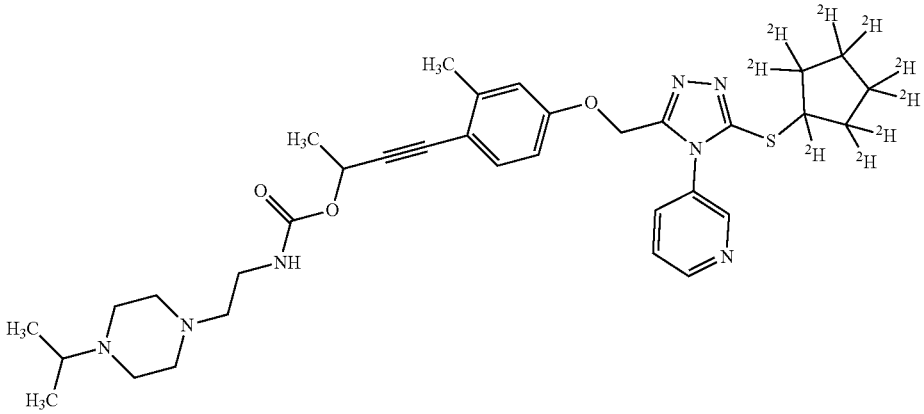 [SMILES: [2H]C1([2H])C([2H])([2H])C([2H])([2H])C([2H])(Sc2nnc(COc3ccc(C#CC(C)OC(=O)NCCN4CCN(C(C)C)CC4)c(C)c3)n2-c2cccnc2)C1([2H])[2H]] | 627.3783 |
| 43 | 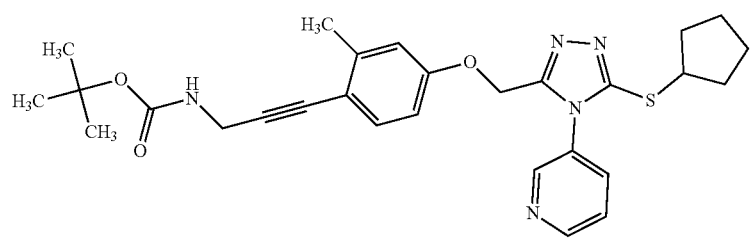 [SMILES: Cc1cc(OCc2nnc(SC3CCCC3)n2-c2cccnc2)ccc1C#CCNC(=O)OC(C)(C)C] | 520.2376 |
| 44 | 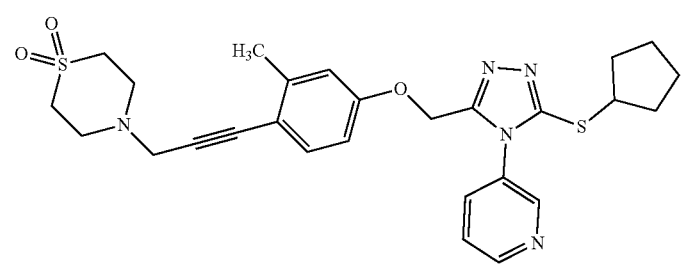 [SMILES: Cc1cc(OCc2nnc(SC3CCCC3)n2-c2cccnc2)ccc1C#CCN1CCS(=O)(=O)CC1] | 538.1943 |
| 45 | 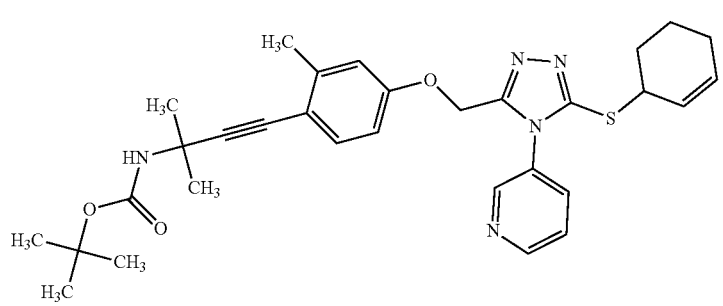 [SMILES: Cc1cc(OCc2nnc(SC3C=CCCC3)n2-c2cccnc2)ccc1C#CC(C)(C)NC(=O)OC(C)(C)C] | 560.2686 |

TABLE III-continued

| No | Compound | Analytical Data; M + H (LC-HRMS) |
|---|---|---|
| 46 | | 529.2940 |
| 47 | | 562.1904 |
| 48 | | 363.1277 |
| 49 | | 520.2376 |
| 50 | | 550.1907 |

TABLE III-continued

| No | Compound | Analytical Data; M + H (LC-HRMS) |
|---|---|---|
| 51 | | 373.2019 |
| 52 | | 506.2567 |
| 53 | | 600.2997 |
| 54 | | 492.2063 |
| 55 | | 435.1668 |

TABLE III-continued

| No | Compound | Analytical Data; M + H (LC-HRMS) |
|---|---|---|
| 56 | | 416.1539 |
| 57 | | 505.2269 |
| 58 | | 421.1691 |
| 59 | | 602.2907 |
| 60 | | 630.3221 |

TABLE III-continued

| No | Compound | Analytical Data; M + H (LC-HRMS) |
|---|---|---|
| 61 | | 630.2858 |
| 62 | | 698.3096 |
| 63 | | 581.2002 |
| 64 | | 565.2050 |
| 65 | | 594.2312 |

TABLE III-continued
| No | Compound | Analytical Data; M + H (LC-HRMS) |
|---|---|---|
| 66 | 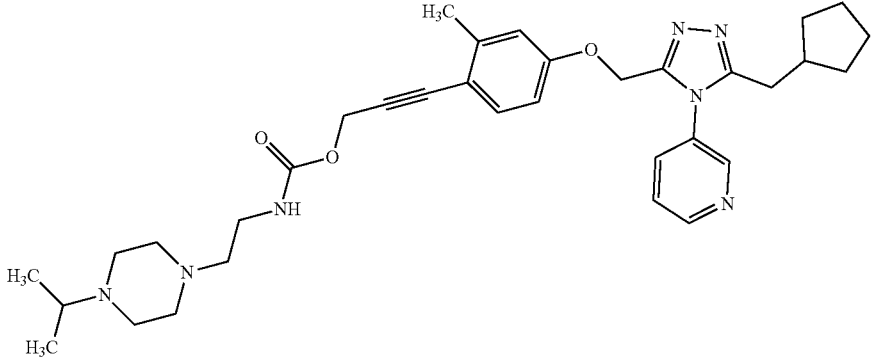 [SMILES: Cc1cc(OCc2nnc(CC3CCCC3)n2-c2cccnc2)ccc1C#CCOC(=O)NCCN1CCN(C(C)C)CC1] | 600.3653 |
| 67 | 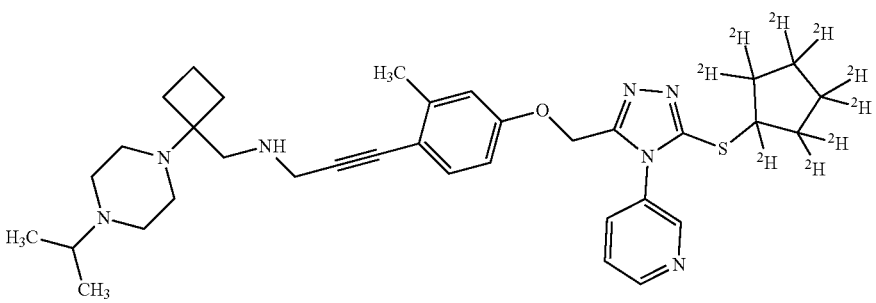 [SMILES: [2H]C1([2H])C([2H])([2H])C([2H])([2H])C([2H])(Sc2nnc(COc3ccc(C#CCNCC4(N5CCN(C(C)C)CC5)CCC4)c(C)c3)n2-c2cccnc2)C1([2H])[2H]] | 623.4198 |
| 68 | 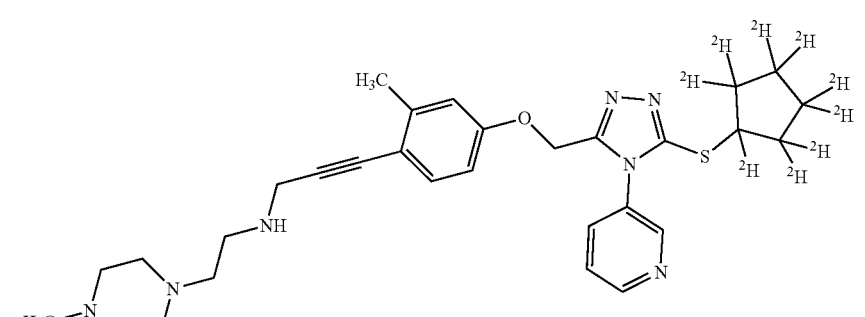 | 555.3572 |
| 69 | 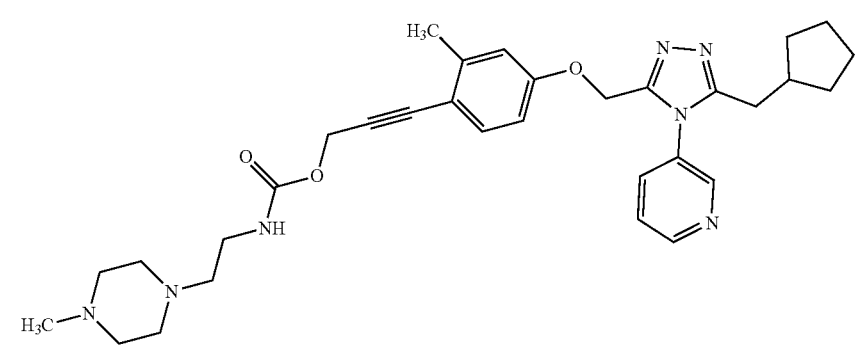 [SMILES: Cc1cc(OCc2nnc(CC3CCCC3)n2-c2cccnc2)ccc1C#CCOC(=O)NCCN1CCN(C)CC1] | 572.3339 |

TABLE III-continued

| No | Compound | Analytical Data; M + H (LC-HRMS) |
|---|---|---|
| 70 | | 600.3290 |
| 71 | | 630.3221 |
| 72 | | 574.2479 |
| 73 | | 629.3379 |

TABLE III-continued

| No | Compound | Analytical Data; M + H (LC-HRMS) |
|---|---|---|
| 74 | | 451.1597 |
| 75 | | 573.2642 |
| 76 | | 559.2486 |
| 77 | | 606.2655 |
| 78 | | 679.2731 |

TABLE III-continued
| No | Compound | Analytical Data; M + H (LC-HRMS) |
|---|---|---|
| 79 | 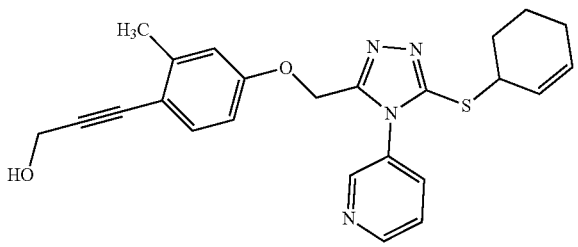 | 433.1689 |
| 80 | 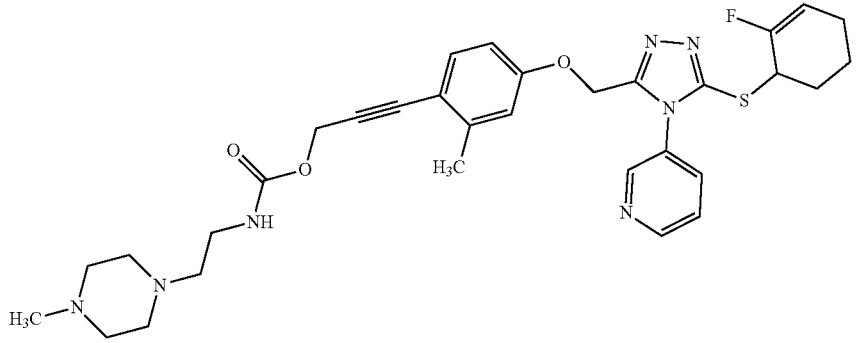 [SMILES: Cc1cc(OCc2nnc(SC3CCCC=C3F)n2-c2cccnc2)ccc1C#CCOC(=O)NCCN1CCN(C)CC1] | 620.2809 |
| 81 | 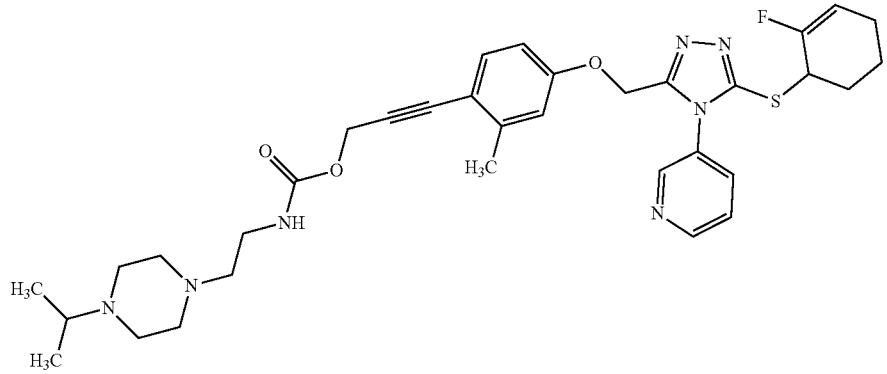 [SMILES: Cc1cc(OCc2nnc(SC3CCCC=C3F)n2-c2cccnc2)ccc1C#CCOC(=O)NCCN1CCN(C(C)C)CC1] | 648.3122 |
| 82 | 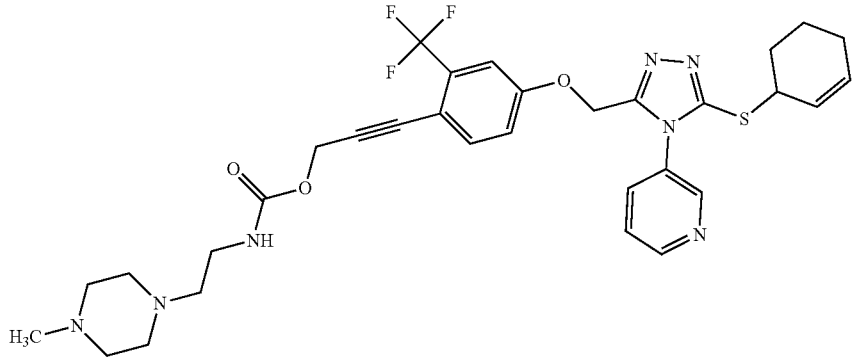 [SMILES: CN1CCN(CCNC(=O)OCC#Cc2ccc(OCc3nnc(SC4C=CCCC4)n3-c3cccnc3)cc2C(F)(F)F)CC1] | 656.2618 |

TABLE III-continued

| No | Compound | Analytical Data; M + H (LC-HRMS) |
|---|---|---|
| 83 | | 474.1956 |
| 84 | | 467.1296 |
| 85 | | 636.2523 |
| 86 | | 500.2113 |
| 87 | | 500.2112 |

TABLE III-continued
| No | Compound | Analytical Data; M + H (LC-HRMS) |
|---|---|---|
| 88 | 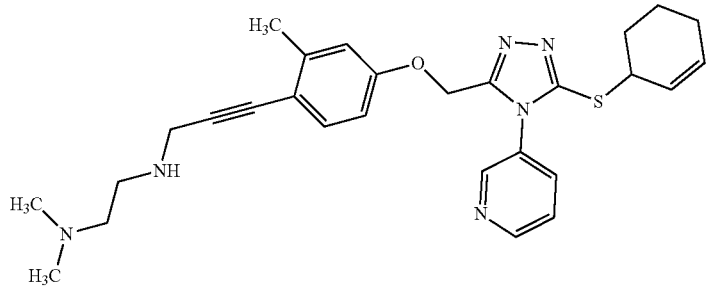 [SMILES: Cc1cc(OCc2nnc(SC3C=CCCC3)n2-c2cccnc2)ccc1C#CCNCCN(C)C] | 503.2584 |
| 89 | 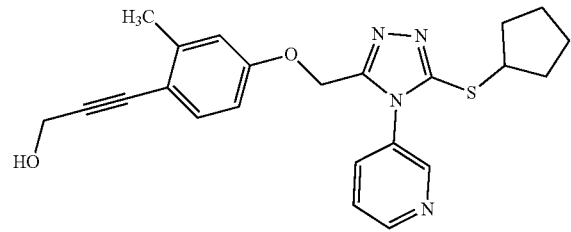 | 421.1696 |
| 90 | 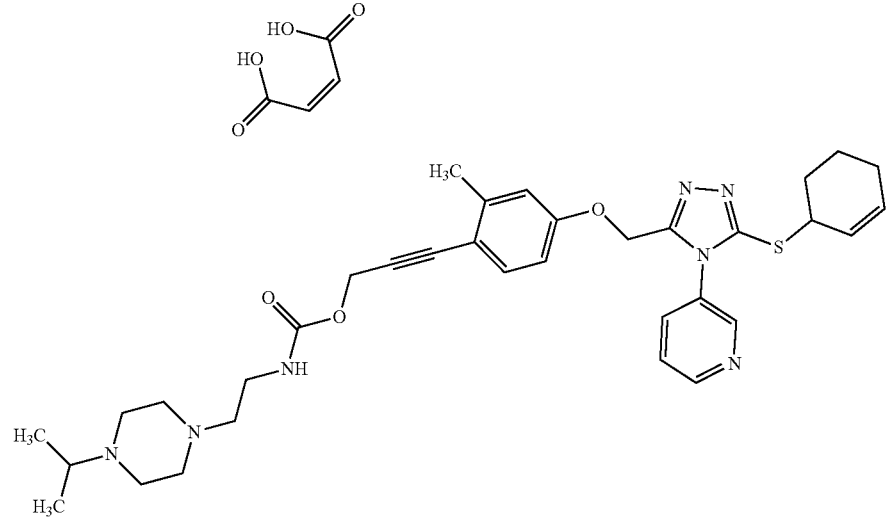 | 630.3218 |
| 91 | 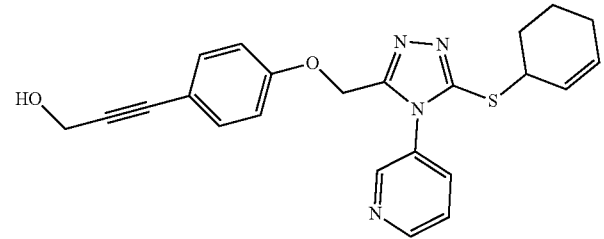 [SMILES: OCC#Cc1ccc(OCc2nnc(SC3C=CCCC3)n2-c2cccnc2)cc1] | 433.1690 |

TABLE III-continued
| No | Compound | Analytical Data; M + H (LC-HRMS) |
|---|---|---|
| 92 | 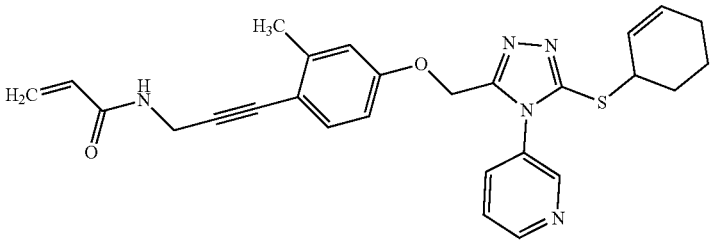 [SMILES: C=CC(=O)NCC#Cc1ccc(OCc2nnc(SC3C=CCCC3)n2-c2cccnc2)cc1C] | 486.1957 |
| 93 | 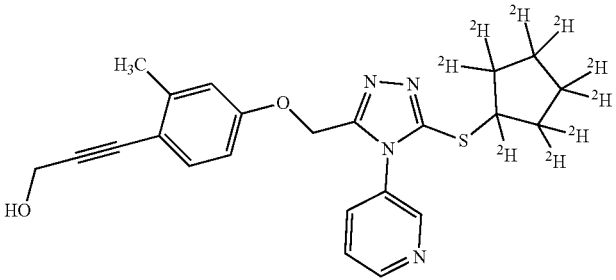 [SMILES: [2H]C1([2H])C([2H])([2H])C([2H])([2H])C([2H])(Sc2nnc(COc3ccc(C#CCO)c(C)c3)n2-c2cccnc2)C1([2H])[2H]] | 430.2256 |
| 94 | 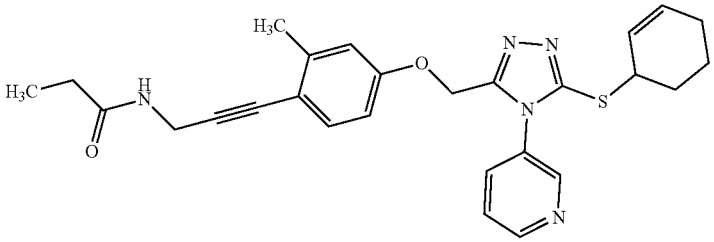 [SMILES: CCC(=O)NCC#Cc1ccc(OCc2nnc(SC3C=CCCC3)n2-c2cccnc2)cc1C] | 488.2114 |
| 95 | 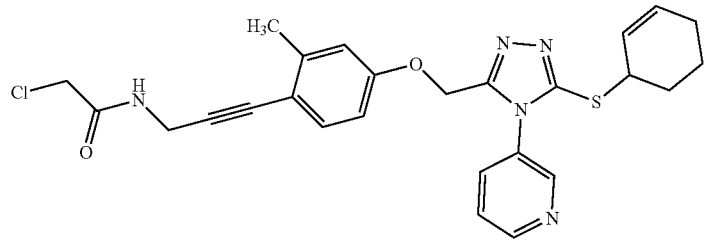 [SMILES: Cc1cc(OCc2nnc(SC3C=CCCC3)n2-c2cccnc2)ccc1C#CCNC(=O)CCl] | 508.1568 |
| 96 | 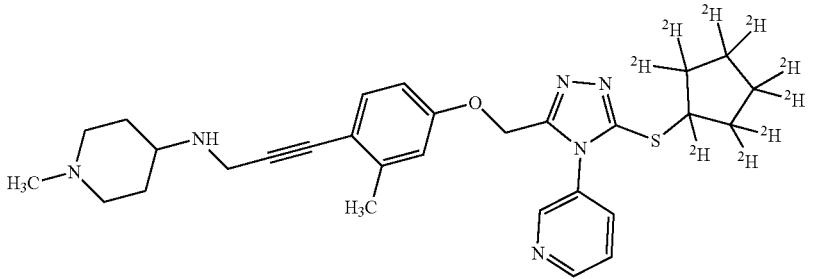 [SMILES: [2H]C1([2H])C([2H])([2H])C([2H])([2H])C([2H])(Sc2nnc(COc3ccc(C#CCNC4CCN(C)CC4)c(C)c3)n2-c2cccnc2)C1([2H])[2H]] | 554.3619 |

TABLE III-continued

| No | Compound | Analytical Data; M + H (LC-HRMS) |
|---|---|---|
| 97 | | 437.1437 |
| 98 | | 465.1590 |
| 99 | | 405.1917 |
| 100 | | 627.3783 |
| 101 | | 587.2799 |

TABLE III-continued

| No | Compound | Analytical Data; M + H (LC-HRMS) |
|---|---|---|
| 102 | | 587.2438 |
| 103 | | 500.2115 |
| 104 | | 541.2017 |
| 105 | | 434.2003 |

TABLE III-continued

| No | Compound | Analytical Data; M + H (LC-HRMS) |
|---|---|---|
| 106 | | 491.2219 |
| 107 | | 606.2655 |
| 108 | | 573.2642 |
| 109 | | 436.2129 |

TABLE III-continued

| No | Compound | Analytical Data; M + H (LC-HRMS) |
|---|---|---|
| 110 | | 683.3373 |
| 111 | | 727.3636 |
| 112 | | 488.2114 |
| 113 | | 455.1345 |

TABLE III-continued

| No | Compound | Analytical Data; M + H (LC-HRMS) |
|----|----------|----------------------------------|
| 114 | | 455.1348 |
| 115 | | 444.1487 |
| 116 | | 467.1546 |
| 117 | | 429.2414 |
| 118 | | 595.2298 |

TABLE III-continued
| No | Compound | Analytical Data; M + H (LC-HRMS) |
|---|---|---|
| 119 | 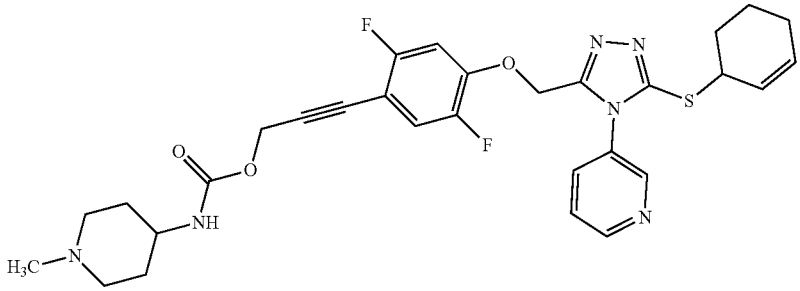 [SMILES: CN1CCC(NC(=O)OCC#Cc2cc(F)c(OCc3nnc(SC4C=CCCC4)n3-c3cccnc3)cc2F)CC1] | 595.2296 |
| 120 | 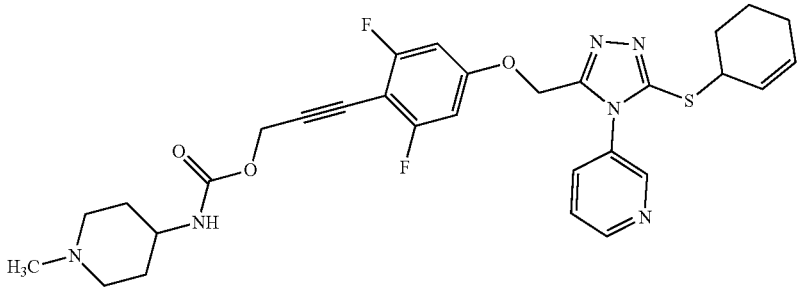 [SMILES: CN1CCC(NC(=O)OCC#Cc2c(F)cc(OCc3nnc(SC4C=CCCC4)n3-c3cccnc3)cc2F)CC1] | 595.2297 |
| 121 | 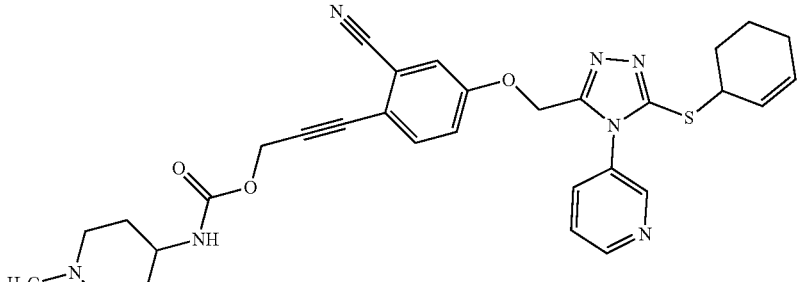 | 585.2437 |
| 122 | 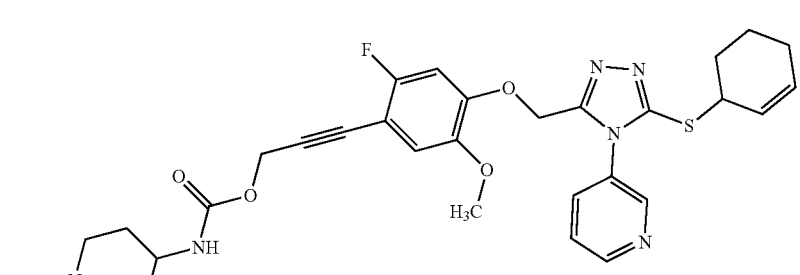 | 607.2493 |
| 123 | 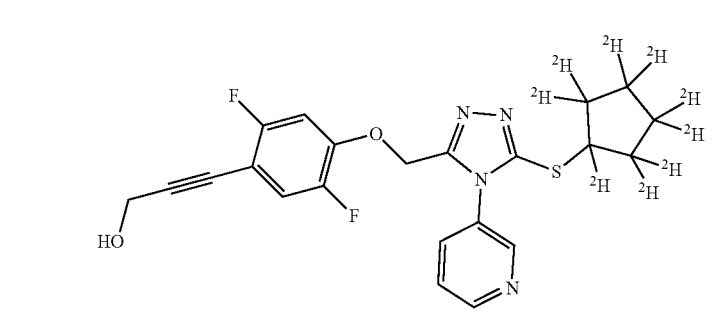 [SMILES: [2H]C1([2H])C([2H])([2H])C([2H])([2H])C([2H])(Sc2nnc(COc3cc(F)c(C#CCO)cc3F)n2-c2cccnc2)C1([2H])[2H]] | 452.1905 |

TABLE III-continued
| No | Compound | Analytical Data; M + H (LC-HRMS) |
|---|---|---|
| 124 | 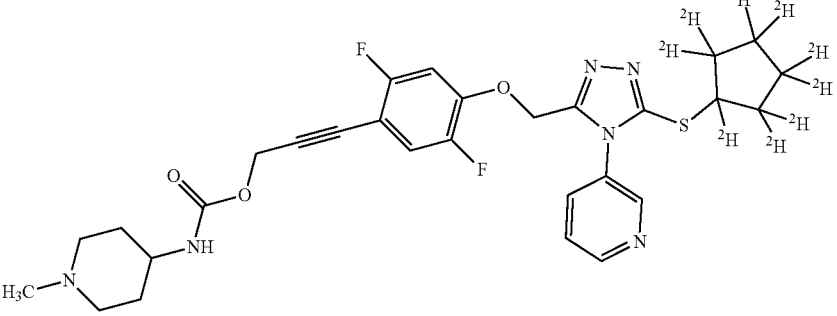 | 592.2858 |
| 125 | 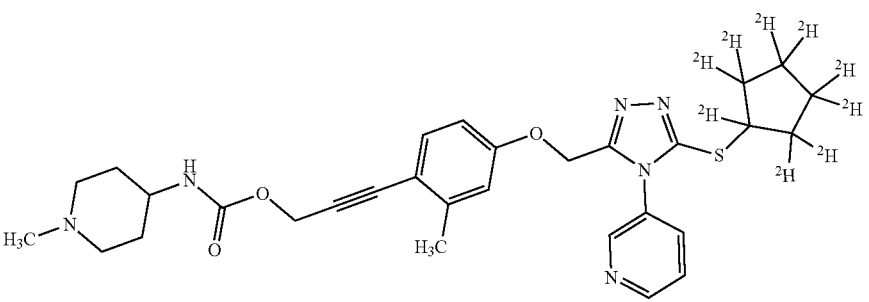 [SMILES: [2H]C1([2H])C([2H])([2H])C([2H])([2H])C([2H])(Sc2nnc(COc3ccc(C#CCOC(=O)NC4CCN(C)CC4)c(C)c3)n2-c2cccnc2)C1([2H])[2H]] | 570.3203 |
| 126 | 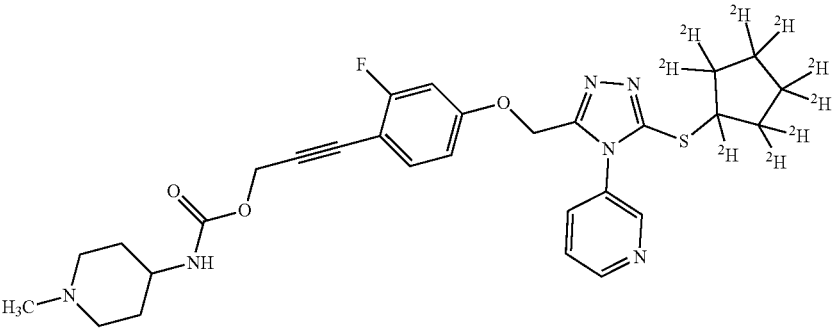 [SMILES: [2H]C1([2H])C([2H])([2H])C([2H])([2H])C([2H])(Sc2nnc(COc3ccc(C#CCOC(=O)NC4CCN(C)CC4)c(F)c3)n2-c2cccnc2)C1([2H])[2H]] | 574.2957 |
| 127 | 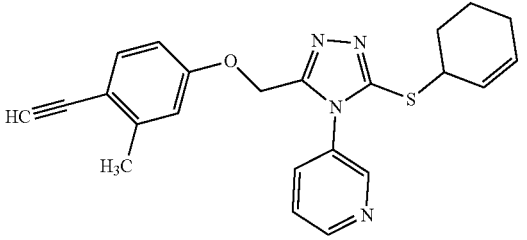 [SMILES: C#Cc1ccc(OCc2nnc(SC3C=CCCC3)n2-c2cccnc2)cc1C] | 403.1584 |
| 128 | 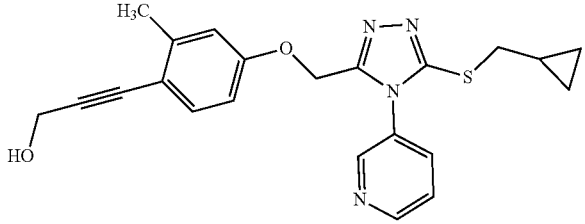 [SMILES: Cc1cc(OCc2nnc(SCC3CC3)n2-c2cccnc2)ccc1C#CCO] | 407.1534 |

TABLE III-continued
| No | Compound | Analytical Data; M + H (LC-HRMS) |
|---|---|---|
| 129 | 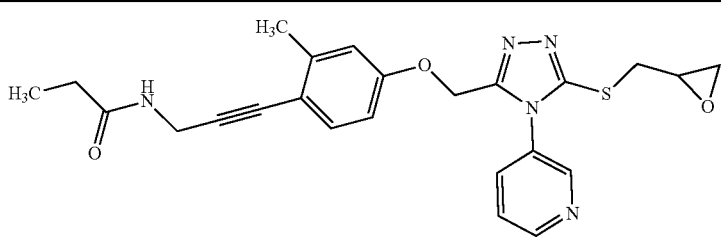 | 464.1745 |
| 130 | 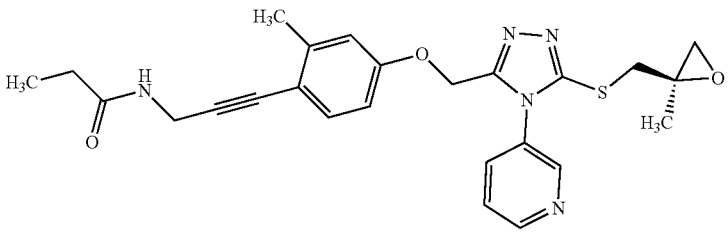 [SMILES: CCC(=O)NCC#Cc1ccc(OCc2nnc(SC[C@@]3(C)CO3)n2-c2cccnc2)cc1C] | 478.1906 |
| 131 | 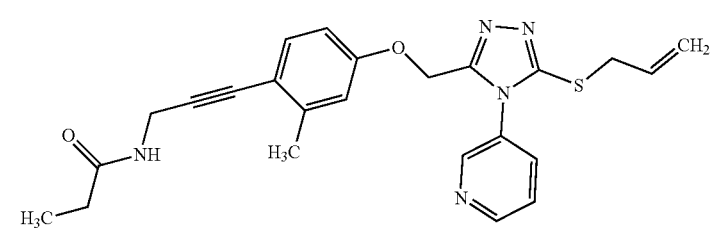 [SMILES: C=CCSc1nnc(COc2ccc(C#CCNC(=O)CC)c(C)c2)n1-c1cccnc1] | 448.1803 |
| 132 | 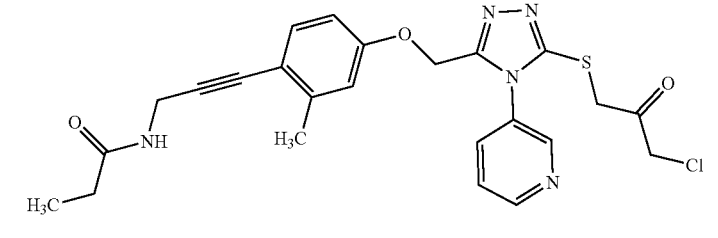 [SMILES: CCC(=O)NCC#Cc1ccc(OCc2nnc(SCC(=O)CCl)n2-c2cccnc2)cc1C] | 498.1357 |
| 133 | 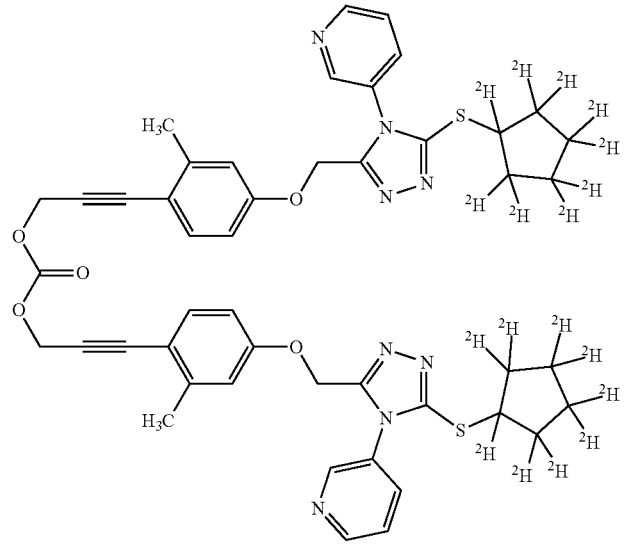 [SMILES: [2H]C1([2H])C([2H])([2H])C([2H])([2H])C([2H])(Sc2nnc(COc3ccc(C#CCOC(=O)OCC#Cc4ccc(OCc5nnc(SC6([2H])C([2H])([2H])C([2H])([2H])C([2H])([2H])C6([2H])[2H])n5-c5cccnc5)cc4C)c(C)c3)n2-c2cccnc2)C1([2H])[2H]] | 885.4229 |

TABLE III-continued

| No | Compound | Analytical Data; M + H (LC-HRMS) |
|---|---|---|
| 134 | 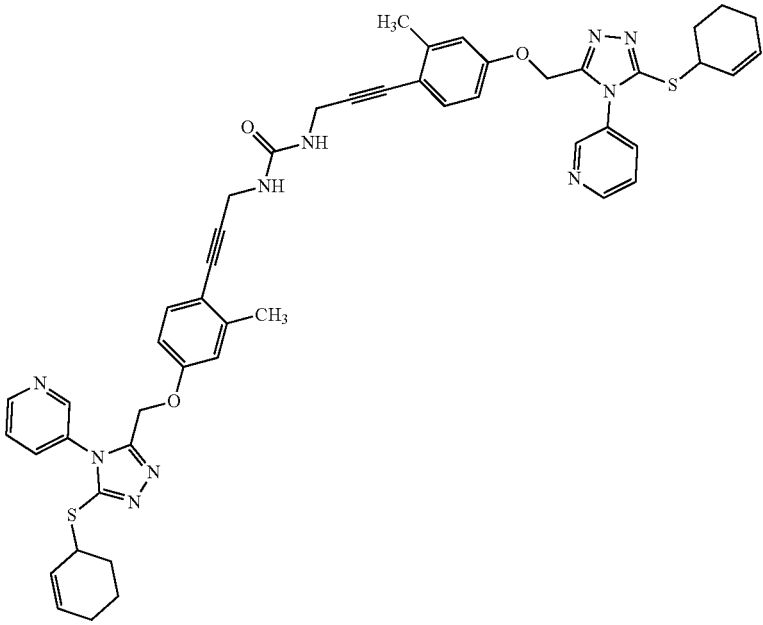 [SMILES: Cc1cc(OCc2nnc(SC3C=CCCC3)n2-c2cccnc2)ccc1C#CCNC(=O)NCC#Cc1ccc(OCc2nnc(SC3C=CCCC3)n2-c2cccnc2)cc1C] | 889.3425 |

II. Methods of Treatment

In some embodiments, the compounds of the present disclosure have a Biomol Green™ $IC_{50}$ value of less than about 25 µM, meaning that at a concentration of 25 µM, the compounds inhibit the activity of p97 by at least about half. In other embodiments, the compounds inhibit the activity of p97 in the assay by more than half. Biomol Green (Enzo) is a bioluminescent, homogeneous assay that measures ADP formed from a biochemical reaction. Because of its high sensitivity, the assay is suitable for monitoring enzyme activities at very early substrate conversions requiring very low amount of enzymes. This is critical since inhibitor potency has to be demonstrated at the cellular level where ATP is present at millimolar concentrations. The assay procedure used may be the same as in Zhang et al., "Altered cofactor regulation with disease-associated p97/VCP mutations," *Proc. Natl. Acad. Sci. USA,* 112(14), E1705-E1714 (2015).

One aspect of the present invention includes methods of modulating p97 in a subject in need thereof. In some embodiments, the treatment of the subject in need thereof comprises administering a compound of the present disclosure (e.g., a compound of Formulae (I), (I'), (II) or Tables I or III) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

In some embodiments, modulation of p97 includes allosteric modulation of p97. In some embodiments, modulation of p97 can be understood as activation of p97 or inhibition of p97. In some embodiments, modulation of p97 leads to at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, including increments therein, increase or decrease in p97 activity. In some embodiments, modulation of p97 leads to at least 2-, 3-, 4-, 5-, 6-, 7-, 8-, 9-, 10-, 15-, 20-, 25-, 30-, 35-, 40-, 45-, 50-, 55-, 60-, 65-, 70-, 75-, 80-, 85-, 90-, 95-, 100-, 200-, 300-, 400-, 500-, 600-, 700-, 800-, 900-, or 1000-fold, including increments therein, increase or decrease in p97 activity.

Another aspect of the present invention includes methods of inhibiting p97 in a subject in need thereof. In some embodiments, the treatment of the subject in need thereof comprises administering a compound of the present disclosure (e.g., a compound of Formulae (I), (I'), (II) or Tables I or III) to the subject suspected of, or already suffering from elevated activity of p97, in an amount sufficient to cure, or at least partially arrest, the symptoms of elevated activity of p97. As such, some embodiments of the disclosure include methods of treating a subject in need thereof who is suffering from, suspected as having, or at risk of having elevated activity of p97.

Another aspect of the present invention includes methods of treating cancers or neurodegenerative disorders susceptible to treatment by p97 modulation or p97 inhibition in a subject diagnosed as having, suspected as having, or at risk of having cancer or a neurodegenerative disorder susceptible to treatment by p97 modulation or p97 inhibition. As such, some embodiments of the disclosure include methods of treating a subject in need thereof who is suffering from, suspected as having, or at risk of having cancer or a neurodegenerative disorder susceptible to treatment by p97 modulation or p97 inhibition. In some embodiments, the treatment of the subject in need thereof comprises administering a compound of the present disclosure (e.g., a compound of Formulae (I), (I'), (II) or Tables I or III) to the subject suspected of, or already suffering from cancer or a neurodegenerative disorder susceptible to treatment by p97 modulation or p97 inhibition, in an amount sufficient to cure, or at least partially arrest, the symptoms of the disease, including its complications and intermediate pathological phenotypes in development of the disease.

In some embodiments, cancers susceptible to treatment by p97 modulation or p97 inhibition include but are not limited to solid tumor cancers, non-small cell lung carcinoma, multiple myeloma, or mantle cell lymphoma. In some embodiments, cancers susceptible to treatment by p97 modulation or p97 inhibition include a solid tumor. See Valle et al., "Critical Role of VCP/p97 in the Pathogenesis and Progression of Non-Small Cell Lung Carcinoma," *PlosOne*, 6(12): e29073 (2011) and Deshaies, "Proteotoxic crisis, the ubiquitin-proteasome system, and cancer therapy," *BMC Biology* 12(94), 1 (2014).

In some embodiments, neurodegenerative disorders susceptible to treatment by p97 modulation or p97 inhibition include but are not limited to inclusion body myopathy (IBM), Paget's disease of the bone (PDB), frontotemporal dementia (FTD) and amyotrophic lateral sclerosis (ALS)). Neurodegenerative disorders also include subjects having p97 mutations, and symptoms manifesting as, for example, Parkinsonism, ataxia, cataracts, dilated cardiomyopathy, hepatic fibrosis, and hearing loss.

The compound may be included in a pharmaceutical formulation, such as those disclosed herein, and may be administered in any pharmaceutically acceptable manner, including methods of administration described herein.

The compounds useful in the methods of the present invention are administered to a mammal in an amount effective in treating or preventing elevated activity of p97, cancers susceptible to treatment by p97 modulation or p97 inhibition, or neurodegenerative disorders susceptible to treatment by p97 modulation or p97 inhibition. The therapeutically effective amount can be determined by methods known in the art.

An effective amount of a compound useful in the methods of the present invention, for example in a pharmaceutical composition, may be administered to a mammal in need thereof by any of a number of well-known pharmaceutically acceptable methods for administering pharmaceutical compounds. The compound may be administered systemically or locally. In one embodiment, the compound is administered intravenously. For example, the compounds useful in the methods of the present technology may be administered via rapid intravenous bolus injection. In some embodiments, the compound is administered as a constant rate intravenous infusion. The compound may also be administered orally, topically, intranasally, intramuscularly, subcutaneously, or transdermally. Other routes of administration include intracerebroventricularly or intrathecally. Intracerebroventiculatly refers to administration into the ventricular system of the brain. Intrathecally refers to administration into the space under the arachnoid membrane of the spinal cord.

The compounds useful in the methods of the present technology may also be administered to mammals by sustained or controlled release, as is known in the art. Sustained release administration is a method of drug delivery to achieve a certain level of the drug over a particular period of time. The level typically is measured by serum or plasma concentration.

In one preferred embodiment, the compounds are administered orally. In one preferred embodiment, the compounds are administered intravenously. In one preferred embodiment, the compounds are administered at less than about 1 gram per day. In other embodiments of the invention, the compounds are administered at less than about 10, at less than about 9, at less than about 8, at less than about 7, at less than about 6, at less than about 5, less than about 4, less than about 3, less than about 2, less than about 1, less than about 0.9, less than about 0.8, less than about 0.7, less than about 0.6, less than about 0.5, less than about 0.4, less than about 0.3, less than about 0.2, or less than about 0.1 grams per day, or any amount in between these values.

III. Pharmaceutical Formulations

For oral administration, liquid or solid dose formulations may be used. Some non-limiting examples of oral dosage formulations include tablets, gelatin capsules, pills, troches, elixirs, suspensions, syrups, wafers, chewing gum and the like. The compounds can be mixed with a suitable pharmaceutical carrier (vehicle) or excipient as understood by practitioners in the art. Non-limiting examples of carriers and excipients include starch, milk, sugar, certain types of clay, gelatin, lactic acid, stearic acid or salts thereof, including magnesium or calcium stearate, talc, vegetable fats or oils, gums and glycols.

For systemic, intracerebroventricular, intrathecal, topical, intranasal, subcutaneous, or transdermal administration, formulations of the compounds useful in the methods of the present technology may utilize conventional diluents, carriers, or excipients etc., such as are known in the art can be employed to deliver the compounds. For example, the formulations may comprise one or more of the following: a stabilizer, a surfactant (such as a nonionic, ionic, anionic, cationic, or zwitterionic surfactant), and optionally a salt and/or a buffering agent. The compound may be delivered in the form of a solution or in a reconstituted lyophilized form.

In some embodiments, the stabilizer may, for example, be an amino acid, such as for instance, glycine or an oligosaccharide, such as for example, sucrose, tetralose, lactose or a dextran. Alternatively, the stabilizer may be a sugar alcohol, such as for instance, sorbitol, mannitol, xylitol, or a combination thereof. In some embodiments, the stabilizer or combination of stabilizers constitutes from about 0.1% to about 10% by weight of the formulation, or any percentage in between these two values.

In some embodiments, the surfactant is a nonionic surfactant, such as a polysorbate. Some examples of suitable surfactants include polysorbates (e.g., Tween20, Tween80); a polyethylene glycol or a polyoxyethylene polyoxypropylene glycol, such as Pluronic F-68 at from about 0.001% (w/v) to about 10% (w/v), or any percentage in between these two values.

A salt or buffering agent may be any salt or buffering agent, such as for example, sodium chloride, or sodium/potassium phosphate, respectively. In certain embodiments, the buffering agent maintains the pH of the pharmaceutical composition in the range of about 5.5 to about 7.5, or any pH in between these two values. The salt and/or buffering agent is also useful to maintain the osmolality at a level suitable for administration to a human or an animal. In some embodiments, the salt or buffering agent is present at a roughly isotonic concentration of about 150 mM to about 300 mM.

The formulations of the compounds useful in the methods of the present technology may additionally comprise one or more conventional additives. Some non-limiting examples of such additives include a solubilizer such as, for example, glycerol; an antioxidant such as for example, benzalkonium chloride (a mixture of quaternary ammonium compounds, known as "quats"), benzyl alcohol, chloretone or chlorobutanol; anaesthetic agent such as for example a morphine derivative; or an isotonic agent etc., such as described above. As a further precaution against oxidation or other spoilage, the pharmaceutical compositions may be stored under nitrogen gas in vials sealed with impermeable stoppers.

The mammal can be any mammal, including, for example, farm animals, such as sheep, pigs, cows, and horses; pet animals, such as dogs and cats; laboratory animals, such as rats, mice and rabbits. In some embodiments, the mammal is a human.

IV. Combination Therapy

In some embodiments, the compounds of the present disclosure may be combined with one or more additional therapies for the prevention or treatment of a disease or condition amenable to treatment by modulation of p97 or inhibition of p97, including but not limited to inclusion body myopathy (IBM), Paget's disease of the bone (PDB), frontotemporal dementia (FTD), and amyotrophic lateral sclerosis (ALS). Additional therapeutic agents or active agents include, but are not limited to, alkylating agents, nitrosoureas, antimetabolites, antitumor antibiotics, plant vinca alkaloids, and steroid hormones.

The multiple therapeutic agents may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents.

For example, drugs useful in treating inclusion body myopathy (IBM) include, but are not limited to, Arimoclomol, medications that suppress the immune system, such as corticosteroids (e.g., prednisone), immunosuppressants (e.g., methotrexate, azathioprine, cyclophosphamide, and cyclosporine), oxandrolone, Acthar (preparation of ACTH in 16% gelatin formulation), intravenous immune globulin (IVIG), biological agents (e.g., an antibody against myostatin, MYO-029), anti-TNF agents, Rituximab (rituxan), and Alemtuzumab (campath).

Drugs useful in treating Paget's disease of the bone (PDB) include, but are not limited to, Calcitonin (salmon and human), Bisphosphonates (e.g., etidronate, clodronate, aminobisphosphonates, alendronate, risedronate, pamidronate, zoledronate, tiludronate), zoledronic acid, densosumab, calcium, vitamin D, and painkillers (e.g., ibuprofen and paracetamol).

Drugs useful in treating frontotemporal dementia (FTD) include, but are not limited to, Cholinesterase inhibitors, such as donepezil (Aricept®), rivastigmine (Exelon®) and galantamine (Razadyne®), antidepressants (e.g., fluoxetine (Prozac®), sertraline (Zoloft®), paroxetine (Paxil®), fluvoxamine (Luvox®), citalopram (Celexa®), escitalopram (Lexapro®), trazodone (Desyrel®), venlafaxine (Effexor®), duloxetine (Cymbalta®), bupropion (Wellbutrin®), mirtazepine (Remeron®)), antipsychotics (e.g., olanzepine (Zyprexa®), quetiapine (Seroquel® or Ketipinor®), risperidone (Risperdal®), ziprasidone (Geodon®), aripiprazole (Abilify®), paliperidone (INVEGA®)), valproic acid and divalproex sodium (Depacon™, Depakene®, Depakote®, Depakote® ER), carbamazepine (Tegretol®), gabapentin (Neurontin®), and Memantine (Namenda®).

Drugs useful in treating amyotrophic lateral sclerosis (ALS) include, but are not limited to, riluzole (Rilutek), Radicava (edaravone), pain relievers or muscle relaxants such as baclofen (Gablofen, Kemstro, Lioresal) or diazepam (Diastat, Valium).

In some embodiments, the compounds of the present disclosure can be combined with proteosome inhibitors. In another embodiment, the compounds of the present disclosure can be combined with other anti-cancer agents. In another embodiment, the compounds of the present disclosure can be combined with heat shock protein (HSP) inhibitors. In another embodiment, the compounds of the present disclosure can be combined with two or more of proteasome inhibitors, HSP inhibitors, and other anti-cancer agents.

V. Definitions

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements, or use of a "negative" limitation.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Generally, reference to a certain element such as hydrogen or H is meant to include all isotopes of that element. For example, if a group is defined to include hydrogen or H, it also includes deuterium and tritium. Hence, isotopically labeled compounds are within the scope of the invention. In some embodiments, one or more of the H in Formulae (I) or (I') or (II) is replaced with a deuterium.

In general, "substituted" refers to an organic group (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. The present disclosure is understood to include embodiments where, for instance a "substituted alkyl" optionally contains one or more alkene and/or alkyne. A substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; aryl groups; heteroaryl groups; cycloalkyl groups; heterocyclyl groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocycle and heteroaryl groups also include rings and fused ring systems in which a bond to a hydrogen atom is replaced with a bond to a carbon atom. Therefore, substituted cycloalkyl, aryl, heterocycle and heteroaryl groups may also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above. As stated above, the present disclosure is understood to include embodiments where, for instance a "substituted alkyl" optionally contains one or more alkene and/or alkyne.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-di-substituted cyclohexyl groups, which may be substituted with substituents such as those listed above. In some embodiments, a cycloalkyl group has one or more alkene bonds, but is not aromatic.

Bridged cycloalkyl groups are cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups may be substituted one or more times with non-hydrogen and non-carbon groups as defined above. Representative substituted bridged cycloalkyl groups may be mono-substituted or substituted more than once, such as, but not limited to, mono-, di- or tri-substituted adamantyl groups, which may be substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Heterocycle groups include aromatic (also referred to as heteroaryl) and non-aromatic ring compounds containing 3 or more ring members, of which one or more is a heteroatom such as, but not limited to, N, O, S or B. In some embodiments, heterocycle groups include 3 to 20 ring members, whereas other such groups have 3 to 6, 3 to 10, 3 to 12, or 3 to 15 ring members. Heterocycle groups encompass unsaturated, partially saturated and saturated ring systems, such as, for example, imidazolyl, imidazolinyl and imidazolidinyl groups. The phrase "heterocycle group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocycle groups that have other groups, such as alkyl, oxo or halo groups, bonded to one of the ring members. Rather, these are referred to as "substituted heterocycle groups". Heterocycle groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocycle groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, S or B. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The term "amine" (or "amino") as used herein refers to —NHR* and —NR*R* groups, wherein R* are independently hydrogen, or a substituted or unsubstituted alkyl, alkenyl, alkynyl, cycloalkyl, aryl, aralkyl, heterocyclylalkyl or heterocycle group as defined herein. In some embodiments, the amine is $NH_2$, methylamino, dimethylamino, ethylamino, diethylamino, propylamino, isopropylamino, phenylamino, or benzylamino.

The term "amide" refers to a —NR*R*C(O)— group wherein R* each independently refer to a hydrogen, ($C_1$-$C_8$)alkyl, or ($C_3$-$C_6$)aryl.

Those of skill in the art will appreciate that compounds of the invention may exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

As readily understood by one skilled in the art, a wide variety of functional groups and other structures may exhibit tautomerism, and all tautomers of compounds as described herein are within the scope of the present invention.

Stereoisomers of compounds, also known as "optical isomers," include all chiral, diastereomeric, and racemic forms of a structure, unless the specific stereochemistry is expressly indicated. Thus, compounds used in the present invention include enriched or resolved optical isomers at any or all stereogenic atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

By "pharmaceutically acceptable" is meant a material that is not biologically or otherwise undesirable, e.g., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. and Drug administration.

By "patient" is meant any animal for which treatment is desirable. Patients may be mammals, and typically, as used herein, a patient is a human individual.

The term "pharmaceutically acceptable salt," as used herein, represents salts or zwitterionic forms of the compounds of the present invention which are water or oil-soluble or dispersible; which are suitable for treatment of diseases without undue toxicity, irritation, and allergic-response; which are commensurate with a reasonable benefit/risk ratio; and which are effective for their intended use. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds of the compounds of the present invention and the like.

The term "solvates" is used in its broadest sense. For example, the term solvates includes hydrates formed when a compound of the present invention contains one or more bound water molecules.

Certain compounds within the scope of the disclosure are derivatives referred to as prodrugs. The expression "prodrug" denotes a derivative of a known direct acting drug, e.g. esters and amides, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology* 112: 309-23 (1985); Bodor, N., "Novel Approaches in Prodrug Design," *Drugs of the Future,* 6: 165-82 (1981); and Bundgaard, H., "Design of Prodrugs: Bioreversible-Derivatives for Various Functional Groups and Chemical Entities," in DESIGN OF PRODRUGS (H. Bundgaard, ed.), Elsevier (1985), Goodman and Gilmans, THE PHARMACOLOGICAL BASIS OF THERAPEUTICS, 8th ed., McGraw-Hill (1992). In some embodiments, the "prodrug" is a compound that generally converts to an active compound of the present disclosure within a physiological environment (e.g., stomach, colon, blood). Pro-drugs include esters, carbonates, carbamates, oximes of active alcohols (and/or acids for esters), amides, carbamates, ureas, oximes, Mannich bases, imines of amines (and/or acids for amides), carbondithianes of active thiols, conjugates of reactive species such as a,b-unsaturated carbonyl derivatives. The selection and synthesis of prodrugs include strategies such as those in: Karaman, R., "Prodrugs design based on inter- and intra-molecular chemical processes," *Chem. Biol. Drug Des.,* 82: 643-668 (2013); Huttunen et al., "Prodrugs—from serendipity to rational design," *Pharmacol. Rev.,* 63, 750-771 (2011); Blencowe et al., "Self-immolative linkers in polymeric delivery systems," *Polym. Chem.,* 2: 773-790 (2011); Arpicco et al., "Anticancer prodrugs: An overview of major strategies and recent developments," *Curr. Top. Med. Chem.* (Sharjah, United Arab Emirates), 11: 2346-2381 (2011); Tietze et al., "Antibody-directed enzyme prodrug therapy: A promising approach for a selective treatment of cancer based on prodrugs and monoclonal antibodies" *Chem. Biol. Drug Des.,* 74: 205-211 (2009); Simplicio et al., "Prodrugs for amines," *Molecules,* 13: 519-547 (2008); Rautio et al., "Prodrugs: Design and clinical applications," *Nat. Rev. Drug Discovery,* 7: 255-270 (2008); Lee et al., "Pro-drug and Antedrug: Two Diametrical Approaches in Designing Safer Drugs," *Arch. Pharm. Res.,* 25: 111-136 (2002); and Lee, *Chem. Biol. Drug Des.,* 82: 643-668 (2013). In some embodiments, the prodrug is a dimer. Two non-limiting examples are:

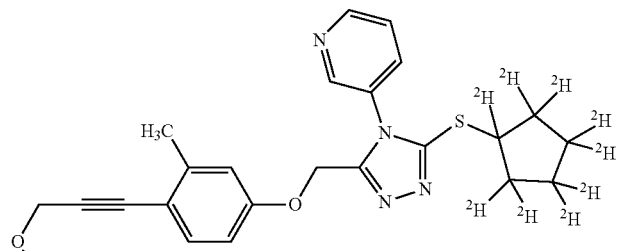
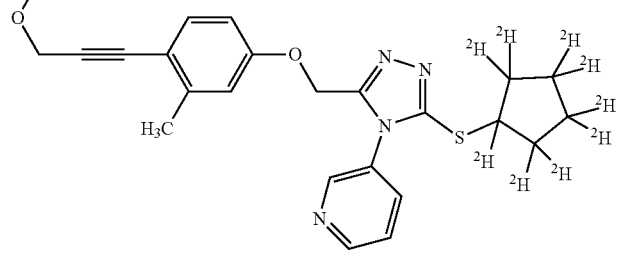

and

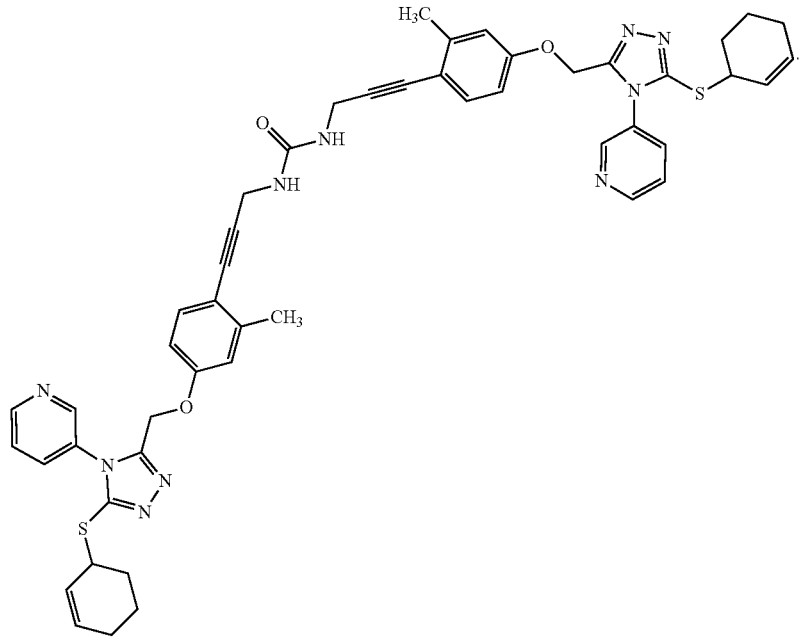

Similar analogs may be prepared based on any compound of Table III, and are included in the present technology.

Generally, reference to a certain moiety capable of being protected (such as hydroxy, amine, carbonyl, etc.) includes the protected groups in some embodiments of the disclosure. For example, in some embodiments, an —OH moiety as included herein also includes —OP, where P is a protecting group. Protecting groups, as referred to herein may be selected by one of ordinary skill in the art, and include the groups and strategies set forth in the art, for example, those such as described in R. Larock, *Comprehensive Organic Transformations*, VCH Publishers (1989); T. W. Greene and P. G. M. Wuts, Greene's protective groups in organic synthesis, John Wiley & Sons (2006); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

This disclosure is not limited to particular embodiments described, as such may, of course, vary. It is also to be understood that the terminology used herein is for the purpose of describing particular embodiments only, and is not intended to be limiting, since the scope of the present invention will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

VI. Working Examples

The present technology is further illustrated by the following examples, which should not be construed as limiting in any way.

General Information.

All non-aqueous reactions were carried out under a nitrogen atmosphere in oven- or flame-dried glassware unless otherwise noted. Anhydrous tetrahydrofuran and diethyl ether were distilled from sodium benzophenone ketyl; anhydrous dichloromethane and toluene were distilled from $CaH_2$; alternatively, the same solvents were obtained from a solvent purification system using alumina columns. All other solvents and reagents were used as obtained from commercial sources without further purification unless noted. Reactions were monitored via TLC using 250 μm pre-coated silica gel 60 $F_{254}$ plates, which were visualized with 254 nm and/or 365 nm UV light and by staining with $KMnO_4$ (1.5 g $KMnO_4$, 10 g $K_2CO_3$, and 1.25 mL 10% NaOH in 200 mL water), cerium molybdate (0.5 g $Ce(NH_4)_2(NO_3)_6$, 12 g $(NH_4)_6Mo_7O_{24} \cdot 4H_2O$, and 28 mL conc. $H_2SO_4$ in 235 mL water), or vanillin (6 g vanillin and 1.5 mL conc. $H_2SO_4$ in 100 mL EtOH). Flash chromatography was performed with SiliCycle silica gel 60 (230-400 mesh) or with ISCO MPLC. $^1H$ and $^{13}C$ NMR spectra were recorded on Bruker Avance 300, 400, or 500 MHz spectrometers, using the residual solvent as an internal standard. IR spectra were obtained on a Smiths IdentifyIR or PerkinElmer Spectrum 100. FIRMS data were obtained on a Thermo Scientific Exactive FIRMS coupled to a Thermo Scientific Accela HPLC system using a 2.1×50 mm 3.5 μm Waters XTerra $C_{18}$ column eluting with $MeCN/H_2O$ containing 0.1% formic acid. Purity of compounds was assessed using the same HPLC system with either the PDA or an Agilent 385 ELSD. All final screening samples passed QC based on >95% purity by LC/MS/ELSD analysis.

General Synthetic Methods

The compounds of the present disclosure can be prepared using the following general methods and procedures. The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley, and Sons, 1991), Rodd's *Chemistry of Carbon Compounds*, Volumes 1-5, and Supplementals (Elsevier Science Publishers, 1989), *Organic Reactions*, Volumes 1-40 (John Wiley, and Sons, 1991), *March's Advanced Organic Chemistry*, (John Wiley, and Sons, 5$^{th}$ Edition, 2001), and *Larock's Comprehensive Organic Transformations* (VCH Publishers Inc., 1989).

More specifically, compounds provided herein can be synthesized as shown below (see Schemes 1 and 2), and following adaptations of the methods shown below and/or methods known to a skilled artisan and/or by using different commercially available starting materials.

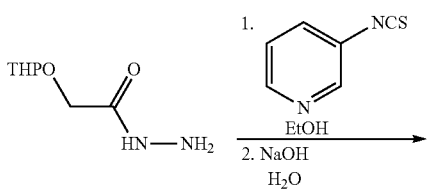

-continued

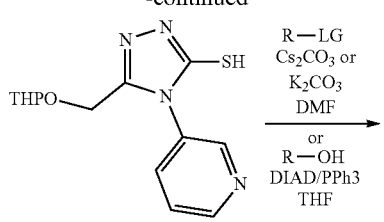

(Similar to: Polucci, P. et al. *J. Med. Chem.* 2013, 437)

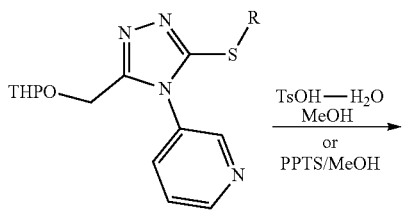

(LG = leaving group, Br, I, Cl, OMs, OTs)

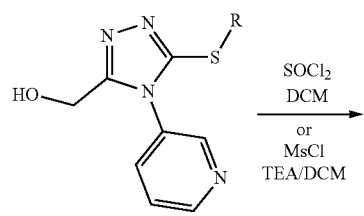

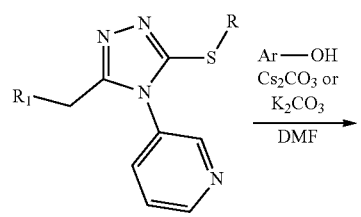

$R_1$ = Cl, OMs

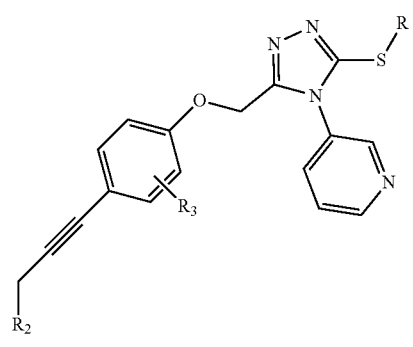

$R_2$ = OH, NPhth

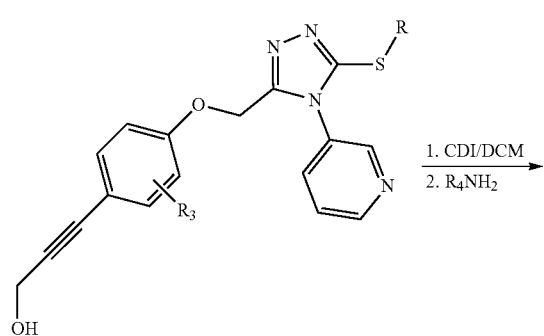

-continued

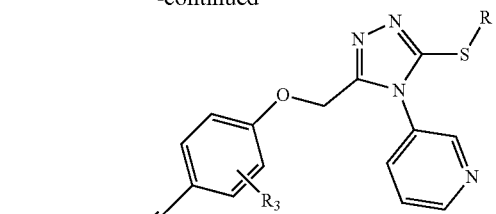

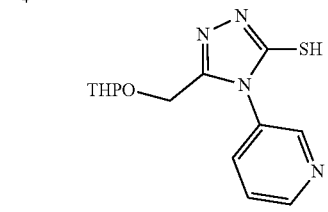

The following general scheme demonstrates an exemplary synthesis of certain compounds within the scope of the disclosure. R of Scheme 1 corresponds to

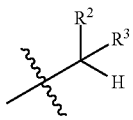

of Formulae (I), (I'), or (II). $R_3$ of Scheme 1 corresponds to optional substitution on Y of Formulae (I), (I'), or (II), when Y is optionally substituted phenyl. $R_4$ of Scheme 1 corresponds to E'-F' of $R^5$ of Formulae (I), (I'), or (II). It would be understood by one of skill in the art that various intermediates in this scheme may be modified accordingly to afford the desired end product.

4-(Pyridin-3-yl)-5-(((tetrahydro-2H-pyran-2-yl)oxy)methyl)-4H-1,2,4-triazole-3-thiol To a solution of 2-((tetrahydro-2H-pyran-2-yl)oxy)acetohydrazide (18.7 g, 107.3 mmol) in EtOH (150 mL) was added 3-isothiocyanatopyridine (14.0 g, 102.8 mmol) at room temperature. After 10 min, a thick precipitate formed and the solution was heated at reflux for 1.5 h. The solution was cooled to room temperature, then further at 0° C. The light brown solid was collected by filtration, washed with hexanes and dried in vacuo to give product (23.9 g, 75%) as a light brown solid. This solid was treated with 1M NaOH (140 mL) at room temperature and the solution was heated to reflux for 2 h. The solution was cooled to room temperature, then to 0° C. and neutralized to pH 6 with 2M HCl. The solid was collected by filtration, washed with cold H$_2$O (10 mL) and further dried under vacuum. The light brown solid was diluted with PhMe (100 mL) and concentrated (2×) to give product as a light brown solid (21.7 g, 97%). M.p. 166-168° C.; IR (neat) 3033, 2943, 2709, 1589, 1437, 1319, 1121, 1108, 964 cm$^{-1}$; $^1$H NMR (500 MHz, DMSO-d$_6$) δ 14.06 (s, 1H), 8.71 (dd, J=4.8, 1.5 Hz, 1H), 8.66 (dd, J=2.5, 0.6 Hz, 1H), 7.96 (ddd, J=8.1, 2.5, 1.5 Hz, 1H), 7.63 (ddd, J=8.1, 4.8, 0.6 Hz, 1H), 4.47 (d, J=13.0 Hz, 1H), 4.44 (t, J=3.0 Hz, 1H), 4.37 (d, J=13.0 Hz, 1H), 3.29-3.25 (m, 1H), 3.19 (td, J=10.3, 3.2 Hz, 1H), 1.47-1.35 (m, 4H), 1.31-1.22 (m, 2H); $^{13}$C NMR (125 MHz, DMSO-$d_6$) δ 169.3, 150.7, 149.5, 149.3, 136.7, 131.3, 124.5, 97.7, 61.1, 59.0, 29.9, 25.1, 18.6; HRMS (LCMS ESI+) m/z calcd for $C_{13}H_{17}O_2N_4S$ [M+H] 293.1072, found 293.1064.

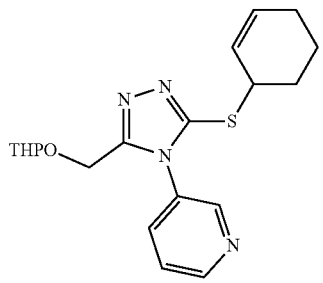

3-(3-(Cyclohex-2-en-1-ylthio)-5-(((tetrahydro-2H-pyran-2-yl)oxy)methyl)-4H-1,2,4-triazol-4-yl)pyridine 3-Bromocyclohexene (0.383 g, 2.14 mmol) was added to a solution of 4-(pyridin-3-yl)-5-(((tetrahydro-2H-pyran-2-yl)oxy)methyl)-4H-1,2,4-triazole-3-thiol (0.500 g, 1.71 mmol) and $Cs_2CO_3$ (0.697 g, 2.14 mmol) in DMF (3.0 mL). The reaction mixture was heated at 80° C. for 2.5 h. The reaction mixture was cooled to room temperature, diluted with $H_2O$, and extracted with EtOAc (3×). The combined organic phase was washed with brine (3×), dried ($Na_2SO_4$), filtered, and concentrated. The residue was purified by chromatography on $SiO_2$ (EtOAc) to give product as a light yellow solid (0.454 g, 68%). $^1$H NMR (500 MHz, CDCl$_3$) δ 8.76 (dd, J=4.8, 1.5 Hz, 1H), 8.65 (d, J=2.5 Hz, 1H), 7.73-7.71 (m, 1H), 7.49 (ddd, J=8.1, 4.8, 0.7 Hz, 1H), 5.87 (dtd, J=9.8, 3.8, 1.5 Hz, 1H), 5.76-5.72 (m, 1H), 4.68 (dd, J=12.6, 5.0 Hz, 1H), 4.58-4.53 (m, 2H), 4.50 (dd, J=12.6, 4.7 Hz, 1H), 3.47-3.39 (m, 2H), 2.11-1.96 (m, 4H), 1.77-1.39 (m, 8H); $^{13}$C NMR (125 MHz, CDCl$_3$) δ 152.8, 150.9, 148.4, 135.0, 132.2, 130.4, 125.5, 123.9, 98.25, 98.22, 61.6, 58.8, 44.1, 30.0, 29.2, 25.1, 24.8, 19.1, 18.7.

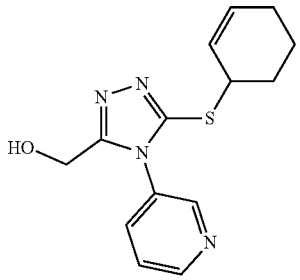 [SMILES: OCc1nnc(SC2C=CCCC2)n1-c1cccnc1]

(5-(Cyclohex-2-en-1-ylthio)-4-(pyridin-3-yl)-4H-1,2,4-triazol-3-yl)methanol

To a solution of 3-(3-(cyclohex-2-en-1-ylthio)-5-(((tetrahydro-2H-pyran-2-yl)oxy)methyl)-4H-1,2,4-triazol-4-yl)pyridine (0.678 g, 1.73 mmol) in MeOH (5.0 mL) was added p-toluenesulfonic acid monohydrate (0.084 g, 0.43 mmol) at room temperature. After 30 h, the reaction mixture was extracted with EtOAc, washed with saturated NaHCO$_3$ (2×). The combined organic layer was washed with brine, dried (Na$_2$SO$_4$), filtered and concentrated to give product as a white solid (0.25 g, 50%). $^1$H NMR (500 MHz, CDCl$_3$) δ 8.77 (dd, J=4.7, 1.2 Hz, 1H), 8.68 (d, J=2.3 Hz, 1H), 7.84 (ddd, J=8.0, 2.3, 1.2 Hz, 1H), 7.52 (dd, J=8.0, 4.7 Hz, 1H), 5.89-5.85 (m, 1H), 5.74-5.70 (m, 1H), 4.63 (s, 2H), 4.52-4.49 (m, 1H), 2.09-1.94 (m, 4H), 1.77-1.62 (m, 3H); $^{13}$C NMR (125 MHz, CDCl$_3$) δ 155.2, 152.7, 151.0, 148.0, 135.0, 132.3, 130.1, 125.4, 124.2, 54.5, 44.1, 29.2, 24.8, 19.1; HRMS (LCMS ESI+) m/z calcd for $C_{14}H_{17}ON_4S$ [M+H] 289.1123, found 289.1119.

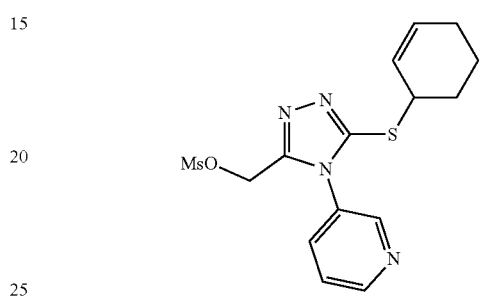

(5-(Cyclohex-2-en-1-ylthio)-4-(pyridin-3-yl)-4H-1,2,4-triazol-3-yl)methyl methanesulfonate To a solution of (5-(cyclohex-2-en-1-ylthio)-4-(pyridin-3-yl)-4H-1,2,4-triazol-3-yl)methanol (0.050 g, 0.17 mmol) and DIPEA (0.038 mL, 0.22 mmol) in CH$_2$Cl$_2$ (1.9 mL) at 0° C. was added MsCl (0.015 mL, 0.19 mmol). The reaction was stirred at 0° C. and slowly warmed to room temperature over about 2.5 h. The reaction was diluted with CH$_2$Cl$_2$, washed with saturated NaHCO$_3$, saturated NH$_4$Cl, dried (MgSO$_4$), filtered, and concentrated. The product was obtained as a mixture of the mesylate and chloride that was carried on without further purification. HRMS (LCMS ESI+) m/z calcd for $C_{15}H_{19}O_3N_4S_2$ [M+H] 367.0893, found 367.0890 and HRMS (LCMS ESI+) calcd for $C_{14}H_{16}N_4ClS$ [M+H] 307.0779, found 307.0776.

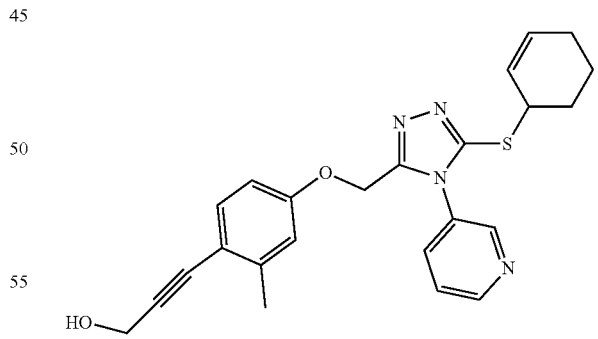

3-(4-((5-(Cyclohex-2-en-1-ylthio)-4-(pyridin-3-yl)-4H-1,2,4-triazol-3-yl)methoxy)-2-methylphenyl)prop-2-yn-1-ol To a solution of crude (5-(cyclohex-2-en-1-ylthio)-4-(pyridin-3-yl)-4H-1,2,4-triazol-3-yl)methyl methanesulfonate (0.225 g, 0.614 mmol) in dry DMF (9 mL) was added 4-(3-hydroxyprop-1-yn-1-yl)-3-methylphenol (0.110 g, 0.675 mmol) and Cs₂CO₃ (0.220 g, 0.675 mmol). The reaction mixture was stirred at room temperature overnight. The reaction mixture was extracted with EtOAc and washed with H₂O. The aqueous layer was back extracted with EtOAc (3×). The combined organic layer was dried (MgSO₄), filtered, and concentrated. The residue was purified by flash chromatography (ISCO-Rf, 0-100% EtOAc/hexanes) to give the product as an off-white foam (0.213 g, 80%). HRMS (LCMS ESI+) calcd for $C_{27}H_{32}O_2N_5S$ [M+H] 433.1693, found 433.1689.

19.8, 18.8; HRMS (LCMS ESI+) calcd for $C_{34}H_{44}O_3N_7S$ [M+H] 630.3221, found 630.3221.

Additional compounds were prepared using analogous experimental procedures and are shown in Table III.

Scheme 2. Assay Method

The assay procedure used were those disclosed in Zhang, et al., "Altered cofactor regulation with disease-associated p97/VCP mutations," *Proc. Natl. Acad. Sci. USA*, 112(14), E1705-E1714 (2015). The following Table IV provides

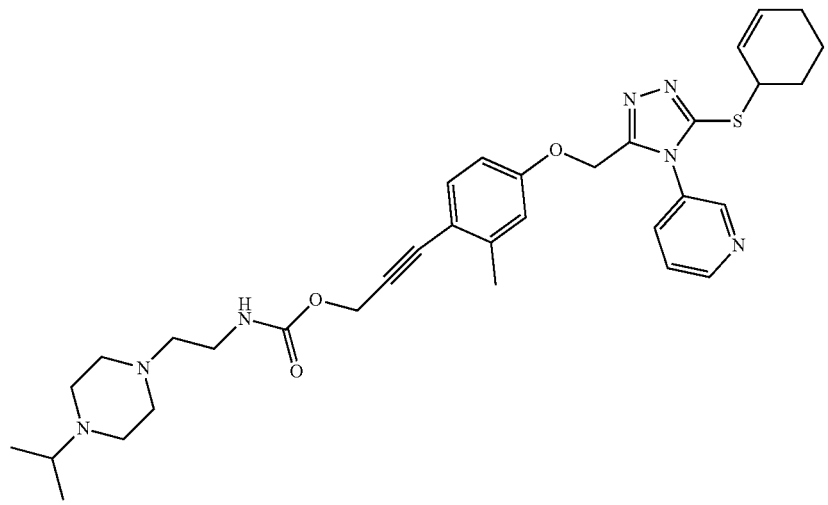 [SMILES: Cc1cc(OCc2nnc(SC3C=CCCC3)n2-c2cccnc2)ccc1C#CCOC(=O)NCCN1CCN(C(C)C)CC1]

3-(4-((5-(Cyclohex-2-en-1-ylthio)-4-(pyridin-3-yl)-4H-1,2,4-triazol-3-yl)methoxy)-2-methylphenyl)prop-2-yn-1-yl (2-(4-isopropylpiperazin-1-yl)ethyl) carbamate To a solution of 3-(4-((5-(cyclohex-2-en-1-ylthio)-4-(pyridin-3-yl)-4H-1,2,4-triazol-3-yl)methoxy)-2-methylphenyl)prop-2-yn-1-ol (0.055 g, 0.13 mmol) in dry CH₂Cl₂ (1.5 mL) was added CDI (0.023 g, 0.14 mmol). The reaction mixture was stirred at room temperature for 2 h. A solution of 2-(4-isopropylpiperazin-1-yl)ethan-1-amine (0.033 g, 0.19 mmol) in dry CH₂Cl₂ (0.5 mL) was then added and the reaction stirred for 2 d at room temperature. The reaction mixture was extracted with CH₂Cl₂ and washed with brine. The organic layer was dried (MgSO₄), filtered, and concentrated. The residue was purified by flash chromatography (ISCO-Rf, 0-20% MeOH/EtOAc) followed by filtration through basic alumina (Al₂O₃, 0-3% MeOH/CH₂Cl₂) to give the product as a white foam (0.058 g, 73%). IR (neat) 3303, 2936, 2815, 1719, 1485, 1445, 1230, 1127, 1023, 984, 707 cm⁻¹; ¹H NMR (600 MHz, acetone-d₆) δ 8.74 (dd, J=4.8, 1.5 Hz, 1H), 8.71 (d, J=2.5 Hz, 1H), 7.98 (ddd, J=8.1, 2.5, 1.5 Hz, 1H), 7.62 (dd, J=8.1, 4.8 Hz, 1H), 7.27 (d, J=8.5 Hz, 1H), 6.82 (d, J=2.5 Hz, 1H), 6.75 (dd, J=8.5, 2.6 Hz, 1H), 6.27 (t, J=4.1 Hz, 1H), 5.87-5.84 (m, 1H), 5.74-5.69 (m, 1H), 5.17-5.22 (m, 2H), 4.88 (s, 2H), 4.41-4.39 (m, 1H), 3.25 (q, J=6.1 Hz, 2H), 2.58 (sept, J=6.5 Hz, 1H), 2.50-2.35 (m, 10H), 2.32 (s, 3H), 2.04-1.99 (m, 3H), 1.97-1.92 (m, 1H), 1.72-1.69 (m, 1H), 1.69-1.59 (m, 1H), 0.96 (d, J=6.5 Hz, 6H); ¹³C NMR (151 MHz, acetone-d₆) δ 158.7, 156.3, 152.9, 152.5, 151.8, 149.0, 143.0, 136.0, 134.1, 132.6, 131.2, 126.5, 125.0, 116.7, 116.3, 113.1, 88.3, 84.6, 60.9, 58.2, 54.8, 54.4, 53.1, 49.2, 44.8, 38.9, 25.4, 20.8, relevant results. The compound number correlates to the numbered compounds in Table III.

TABLE IV

| No. | P97 Biomolgreen; 200 µM ATP; IC₅₀ (µM); |
|---|---|
| 1 | 0.16 |
| 2 | 0.049 |
| 3 | 0.17 |
| 4 | 0.044 |
| 5 | 0.021 |
| 6 | 0.044 |
| 7 | 0.13 |
| 8 | 0.039 |
| 9 | 0.1 |
| 10 | 0.092 |
| 11 | 0.007 |
| 12 | 0.029 |
| 13 | 0.05 |
| 14 | 0.035 |
| 15 | 0.074 |
| 16 | 0.055 |
| 17 | 0.04 |
| 18 | 0.035 |
| 19 | 0.036 |
| 20 | 0.034 |
| 21 | 0.034 |
| 22 | 0.027 |
| 23 | 0.032 |
| 24 | 0.026 |
| 25 | 0.066 |
| 26 | 0.068 |
| 27 | 0.16 |
| 28 | 0.096 |
| 29 | 0.019 |
| 30 | 0.011 |
| 31 | 0.052 |
| 32 | 0.023 |

TABLE IV-continued

| No. | P97 Biomolgreen; 200 μM ATP; IC$_{50}$ (μM); |
|---|---|
| 33 | 0.043 |
| 34 | 0.098 |
| 35 | 0.064 |
| 36 | 0.069 |
| 37 | 0.07 |
| 38 | 0.095 |
| 39 | 0.11 |
| 40 | 0.14 |
| 41 | 0.16 |
| 42 | 0.13 |
| 43 | 0.048 |
| 44 | 0.18 |
| 45 | 0.64 |
| 46 | 0.19 |
| 47 | 0.29 |
| 48 | 0.67 |
| 49 | 0.26 |
| 50 | 0.28 |
| 51 | 0.44 |
| 52 | 0.55 |
| 53 | 1.1 |
| 54 | 2 |
| 55 | 5.3 |
| 56 | >6.7 |
| 57 | 0.11 |
| 58 | 0.093 |
| 59 | 0.025 |
| 60 | 0.019 |
| 61 | 0.029 |
| 62 | 0.11 |
| 63 | 0.048 |
| 64 | 0.06 |
| 65 | 0.047 |
| 66 | 0.12 |
| 67 | 0.2 |
| 68 | 0.17 |
| 69 | 0.066 |
| 70 | 0.098 |
| 71 | 0.026 |
| 72 | 0.18 |
| 73 | 0.052 |
| 74 | 0.51 |
| 75 | 0.025 |
| 76 | 0.03 |
| 77 | 0.02 |
| 78 | 0.09 |
| 79 | 0.037 |
| 80 | 0.23 |
| 81 | 0.16 |
| 82 | 0.043 |
| 83 | 0.046 |
| 84 | 2.108 |
| 85 | 0.934 |
| 86 | 0.06 |
| 87 | 0.058 |
| 88 | 0.06 |
| 89 | 0.028 |
| 90 | 0.084 |
| 91 | 0.032 |
| 92 | 0.026 |
| 93 | 0.048 |
| 94 | 0.03 |
| 95 | 0.03 |
| 96 | 0.067 |
| 97 | 0.026 |
| 98 | 4.819 |
| 99 | 0.183 |
| 100 | 0.025 |
| 101 | 0.03 |
| 102 | 0.03 |
| 103 | 0.03 |
| 104 | 0.05 |
| 105 | 0.03 |
| 106 | 0.02 |
| 107 | 0.013 |
| 108 | 0.015 |
| 109 | 0.03 |
| 110 | 0.06 |
| 111 | 0.03 |
| 112 | 0.025 |
| 113 | 0.04 |
| 114 | 0.02 |
| 115 | 0.1 |
| 116 | 0.04 |
| 117 | 0.99 |
| 118 | 0.017 |
| 119 | 0.012 |
| 120 | 0.012 |
| 121 | 0.03 |
| 122 | 0.019 |
| 123 | 0.021 |
| 124 | 0.01 |
| 125 | 0.016 |
| 126 | 0.016 |
| 127 | 0.038 |
| 128 | 0.13 |
| 129 | not active |
| 130 | not active |
| 131 | 0.33 |
| 132 | 2.775 |
| 133 | 0.91 |
| 134 | 0.25 |

Paragraph A1. A compound having a structure of formula (I):

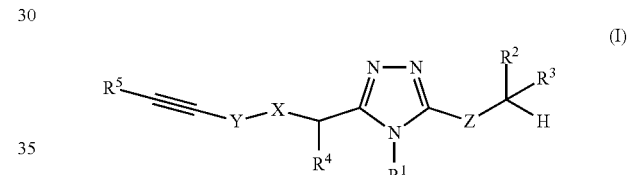

or a pharmaceutically acceptable salt, solvate or prodrug thereof, wherein:

Z is O, SO$_{0-2}$, NR, C(R$^7$)$_2$, alkenyl or alkynyl;

R$^2$ and R$^3$ are independently an optionally substituted C$_{1-9}$, cyclic C$_{3-9}$, heterocyclic or halogen, or R$^2$ and R$^3$ together form an optionally substituted C$_{3-9}$ cyclic or 3- to 9-membered heterocyclic ring;

R$^1$ is optionally substituted phenyl or an optionally substituted 5- or 6-membered heteroaryl;

R$^4$ is H, C(R$^7$)$_2$, aryl, or heteroaryl;

X is O or SO$_{0-2}$;

Y is an optionally substituted alkyl, alkenyl, aryl, heteroaryl, cycloalkyl, or heterocycle;

R$^5$ is H, nitrile, an optionally substituted aryl, an optionally substituted heterocycle, optionally substituted C$_1$-C$_6$ alkyl, optionally substituted C$_3$-C$_9$ cycloalkyl, or

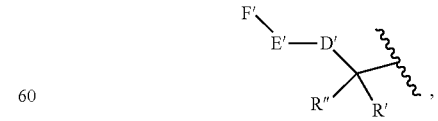

where

R' and R'' are each independently selected from H, optionally substituted alkyl, —OR, halogen (e.g., F, Cl, Br, I), —N(R)$_2$, and optionally substituted cycloalkyl or heterocycle;

or R' and R" may together form a 3- to 6-membered cycloalkyl or heterocycle that is optionally substituted;

D' is selected from —O—, —NR—, —OCONR—, —NRSO$_2$—, —NRCO—, —NRSO$_2$NR—, —NRCOO—, —NRCONR—, and —NRC(NR)NR—;

E' is selected from a bond or an optionally substituted C$_1$-C$_6$ alkyl or cycloalkyl; and F' is selected from H, an optionally substituted cycloalkyl, an optionally substituted heterocycle, an optionally substituted aryl, and an optionally substituted heteroaryl;

R is selected from H, optionally substituted alkyl, or optionally substituted cycloalkyl; and R$^7$ is selected from H, halogen, optionally substituted alkyl, optionally substituted cycloalkyl, —OR, and —N(R)$_2$.

Paragraph A2. The compound of Paragraph A1, wherein X is O or S.

Paragraph A3. The compound of Paragraph A1, wherein Y is selected from:

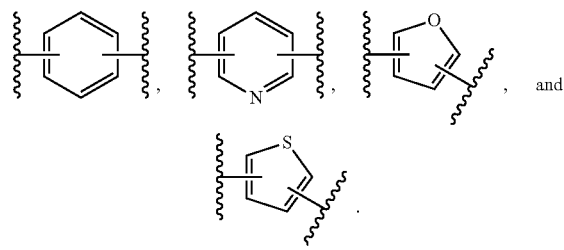

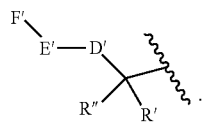

Paragraph A4. The compound of Paragraph A1, wherein Z is selected from: O, S and CH$_2$.

Paragraph A5. The compound of Paragraph A1, wherein R$^5$ is a phenyl, optionally substituted with one or more alkyl, —OR, —CN, —CO$_2$R, halogen, —SR, —SOR, —SO$_2$R, —SF$_5$ or —NR$_2$.

Paragraph A6. The compound of Paragraph A1, wherein R$^5$ is a heterocycle, e.g., morpholine or pyridine, optionally substituted with one or more alkyl, —OR, —CN, —CO$_2$R, halogen, —SR, —SOR, —SO$_2$R, —SF$_5$ or —NR$_2$.

Paragraph A7. The compound of Paragraph A1, wherein R$^5$ is

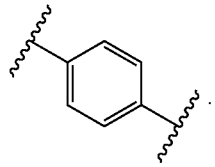 [SMILES: *c1ccc(*)cc1]

Paragraph A8. The compound of Paragraph A7, wherein R' and R" together form a 3- to 6-membered cycloalkyl or heterocycle.

Paragraph A9. The compound of Paragraph A7, wherein R' and R" are each H, or at least one of R' and R" is methyl and any remaining R' or R" is H.

Paragraph A10. The compound of Paragraph A7, wherein at least one of R' and R" is an optionally substituted alkyl.

Paragraph A11. The compound of Paragraph A7, wherein E' is a C$_1$-C$_6$ alkyl and F' is H.

Paragraph A12. The compound of Paragraph A7, wherein F' is an optionally substituted cycloalkyl selected from: cyclopropyl, cyclobutyl, cyclopentyl, and cyclohexyl.

Paragraph A13. The compound of Paragraph A7, wherein F' is an optionally substituted heterocycle selected from: morpholine, azetidine, alkyl-piperidine, alkyl-piperazine, alkyl-diazepane, thiomorpholine 1,1-dioxide, isoindoline-1, 3-dione, tetrahydropyran, and pyrrolidone.

Paragraph A14. The compound of Paragraph A7, wherein F' is an optionally substituted aryl selected from: phenyl, optionally substituted with one or more of: alkyl, —CF$_3$, —OR, —CN, —CO$_2$R, halogen, —SR, —SOR, —SO$_2$R, —SF$_5$ or —NR$_2$.

Paragraph A15. The compound of Paragraph A7, wherein F' is an optionally substituted heteroaryl selected from: alkyl-triazole, tetrazole, imidazole, and isoxazole.

Paragraph A16. The compound of Paragraph A1, wherein R$^1$ is pyridine.

Paragraph A17. The compound of Paragraph A1, wherein R$^2$ and R$^3$ together are a cyclopropyl, cyclopentyl or cyclohexene.

Paragraph A18. The compound of Paragraph A1, wherein Y is an optionally substituted Paragraph A19. A compound selected from Table III or a pharmaceutically acceptable salt, solvate or prodrug thereof.

Paragraph A20. A pharmaceutical composition comprising a compound of any one of Paragraphs A1-A19 and at least one pharmaceutically acceptable excipient.

Paragraph A21. A method of inhibiting p97 in a subject in need thereof, comprising administering to the subject a therapeutically effective amount of a compound of any one of Paragraphs A1-A19 or a therapeutically effective amount of a pharmaceutical composition of Paragraph A20.

Paragraph A22. A method of treating cancer or a neurodegenerative disease susceptible to treatment by p97 inhibition in a subject in need thereof comprising administering to the subject a therapeutically effective amount of a compound of any one of Paragraphs A1-A19 or a therapeutically effective amount of a pharmaceutical composition of Paragraph A20.

Paragraph A23. A method of inhibiting p97 in a subject in need thereof, comprising administering to the subject a therapeutically effective amount of a compound of any one of Paragraphs A1-A19 or a therapeutically effective amount of a pharmaceutical composition of Paragraph A20.

Paragraph A24. A method of treating cancer or a neurodegenerative disease susceptible to treatment by p97 inhibition in a subject in need thereof comprising administering to the subject a therapeutically effective amount of a compound of any one of Paragraphs A1-A19 or a therapeutically effective amount of a pharmaceutical composition of Paragraph A20.

Paragraph A25. The method of Paragraph A22 or Paragraph A24, wherein the method is a method of treating cancer susceptible to treatment by p97 inhibition is selected from the group consisting of a solid tumor, non-small cell lung carcinoma, multiple myeloma, and mantle cell lymphoma.

Paragraph A26. The method of Paragraph A22 or Paragraph A24, wherein the method is a method of treating a neurodegenerative disease susceptible to treatment is selected from the group consisting of inclusion body myopathy (IBM), Paget's disease of the bone (PDB), frontotemporal dementia (FTD) and amyotrophic lateral sclerosis (ALS).

Paragraph B1. A compound having a structure of formula (I'):

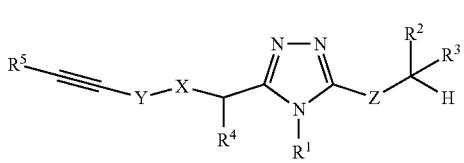

or a pharmaceutically acceptable salt, solvate or prodrug thereof, wherein:

Z is O, $SO_{0-2}$, NR, $C(R^7)_2$, alkenyl or alkynyl;

$R^2$ and $R^3$ are independently optionally substituted $C_{1-6}$ alkyl, optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

X is O, $SO_{0-2}$, or NR;

Y is an optionally substituted alkyl, optionally substituted alkenyl, optionally substituted aryl, optionally substituted heteroaryl, optionally substituted cycloalkyl, or optionally substituted non-aromatic heterocycle;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

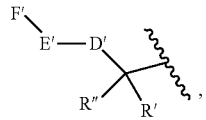

where

R' and R" are each independently selected from the group consisting of H, optionally substituted alkyl, —OR, halogen, —N(R)$_2$, optionally substituted cycloalkyl, and optionally substituted heterocycle;

or R' and R" may together form an optionally substituted 3- to 6-membered cycloalkyl or optionally substituted 3- to 6-membered heterocycle;

D' is selected from the group consisting of —O—, —NR—, —OCONR—, —OCO—, —NRSO$_2$—, —NRCO—, —NRSO$_2$NR—, —NRCOO—, —NR-CONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted alkyl, and optionally substituted cycloalkyl; and $R^7$ is independently selected from the group consisting of H, halogen, optionally substituted alkyl, optionally substituted cycloalkyl, —OR, and —N(R)$_2$.

Paragraph B2. The compound of Paragraph B1, wherein X is O or S.

Paragraph B3. The compound of Paragraph B1 or Paragraph B2, wherein Y is selected from:

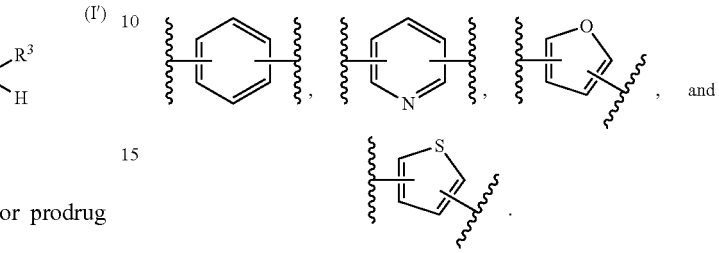

and

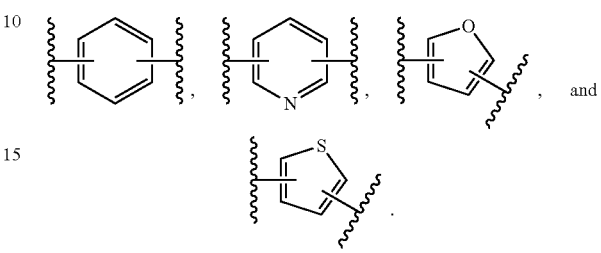

Paragraph B4. The compound of any one of Paragraphs B1-B3, wherein Z is selected from: O, S and CH$_2$.

Paragraph B5. The compound of any one of Paragraphs B1-B4, wherein $R^5$ is a phenyl, optionally substituted with one or more alkyl, —OR, —CN, —CO$_2$R, halogen, —SR, —SOR, —SO$_2$R, —SF$_5$ or —NR$_2$.

Paragraph B6. The compound of any one of Paragraphs B1-B4, wherein $R^5$ is a heterocycle, e.g., morpholine or pyridine, optionally substituted with one or more alkyl, —OR, —CN, —CO$_2$R, halogen, —SR, —SOR, —SO$_2$R, —SF$_5$ or —NR$_2$.

Paragraph B7. The compound of any one of Paragraphs B1-B4, wherein $R^5$ is

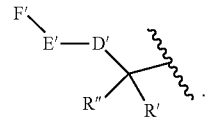

Paragraph B8. The compound of Paragraph B7, wherein R' and R" together form a 3- to 6-membered cycloalkyl or heterocycle.

Paragraph B9. The compound of Paragraph B7, wherein R' and R" are each H, or at least one of R' and R" is methyl and any remaining R' or R" is H.

Paragraph B10. The compound of Paragraph B7, wherein at least one of R' and R" is an optionally substituted alkyl.

Paragraph B11. The compound of Paragraph B7, wherein E' is a $C_1$-$C_6$ alkyl and F' is H.

Paragraph B12. The compound of Paragraph B7, wherein F' is an optionally substituted cycloalkyl selected from: cyclopropyl, cyclobutyl, cyclopentyl, and cyclohexyl.

Paragraph B13. The compound of Paragraph B7, wherein F' is an optionally substituted heterocycle selected from: morpholine, azetidine, alkyl-piperidine, alkyl-piperazine, alkyl-diazepane, thiomorpholine 1,1-dioxide, isoindoline-1,3-dione, tetrahydropyran, and pyrrolidone.

Paragraph B14. The compound of Paragraph B7, wherein F' is an optionally substituted aryl selected from: phenyl, optionally substituted with one or more of: alkyl, —CF$_3$, —OR, —CN, —CO$_2$R, halogen, —SR, —SOR, —SO$_2$R, —SF$_5$ or —NR$_2$.

Paragraph B15. The compound of Paragraph B7, wherein F' is an optionally substituted heteroaryl selected from: alkyl-triazole, tetrazole, imidazole, and isoxazole.

Paragraph B16. The compound of any one of Paragraphs B1-B15, wherein $R^1$ is pyridine.

Paragraph B17. The compound of any one of Paragraphs B1-B16, wherein $R^2$ and $R^3$ together are a cyclopropyl, cyclopentyl or cyclohexene.

Paragraph B18. The compound of Paragraph B2 or any one of Paragraphs B4-B17, wherein Y is an optionally substituted

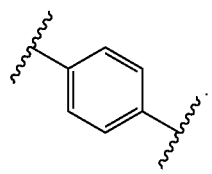 [SMILES: *c1ccc(*)cc1]

Paragraph B19. A compound selected from Table III or a pharmaceutically acceptable salt, solvate or prodrug thereof.

Paragraph B20. A pharmaceutical composition comprising a compound of any one of Paragraphs B1-B19 and at least one pharmaceutically acceptable excipient.

Paragraph B21. A method of inhibiting p97 in a subject in need thereof, comprising administering to the subject a therapeutically effective amount of a compound of any one of Paragraphs B1-B19 or a therapeutically effective amount of a pharmaceutical composition of Paragraph B20.

Paragraph B22. A method of modulating p97 in a subject in need thereof, comprising administering to the subject a therapeutically effective amount of a compound of any one of Paragraphs B1-B19 or a therapeutically effective amount of a pharmaceutical composition of Paragraph B20.

Paragraph B23. A method of treating cancer or a neurodegenerative disease susceptible to treatment by p97 inhibition in a subject in need thereof comprising administering to the subject a therapeutically effective amount of a compound of any one of Paragraphs B1-B19 or a therapeutically effective amount of a pharmaceutical composition of Paragraph B20.

Paragraph B24. The method of Paragraph B23, wherein the method is a method of treating cancer susceptible to treatment by p97 inhibition, and wherein the cancer is selected from the group consisting of a solid tumor, non-small cell lung carcinoma, multiple myeloma, and mantle cell lymphoma.

Paragraph B25. The method of Paragraph B23, wherein the method is a method of treating a neurodegenerative disease susceptible to treatment by p97 inhibition, and wherein the neurodegenerative disease is selected from the group consisting of inclusion body myopathy (IBM), Paget's disease of the bone (PDB), frontotemporal dementia (FTD) and amyotrophic lateral sclerosis (ALS).

Paragraph B26. A method of treating cancer or a neurodegenerative disease susceptible to treatment by p97 modulation in a subject in need thereof comprising administering to the subject a therapeutically effective amount of a compound of any one of Paragraphs B1-B19 or a therapeutically effective amount of a pharmaceutical composition of Paragraph B20.

Paragraph B27. The method of Paragraph B26, wherein the method is a method of treating cancer susceptible to treatment by p97 modulation, and wherein the cancer is selected from the group consisting of a solid tumor, non-small cell lung carcinoma, multiple myeloma, and mantle cell lymphoma.

Paragraph B28. The method of Paragraph B26, wherein the method is a method of treating a neurodegenerative disease susceptible to treatment by p97 modulation, and wherein the neurodegenerative disease is selected from the group consisting of inclusion body myopathy (IBM), Paget's disease of the bone (PDB), frontotemporal dementia (FTD) and amyotrophic lateral sclerosis (ALS).

Paragraph C1. A compound having a structure of formula (II):

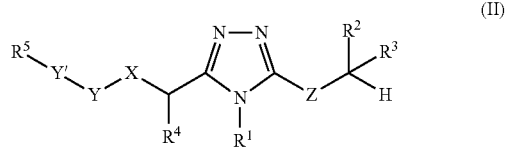

or a pharmaceutically acceptable salt, solvate or prodrug thereof, wherein:

X is O, $SO_{0-2}$, or NR;

Y is optionally substituted alkyl, optionally substituted alkenyl, alkynyl, optionally substituted aryl, optionally substituted heteroaryl, optionally substituted cycloalkyl, or optionally substituted non-aromatic heterocyclic;

Y' is alkynyl, optionally substituted heteroaryl, optionally substituted cycloalkyl, or optionally substituted non-aromatic heterocyclic;

$R^2$ and $R^3$ are independently optionally substituted $C_{1-6}$ alkyl, optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

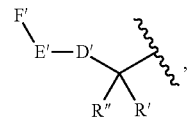

where

R' and R" are each independently selected from the group consisting of H, optionally substituted alkyl, —OR, halogen, —N(R)$_2$, optionally substituted cycloalkyl, and optionally substituted heterocycle;

or R' and R" may together form an optionally substituted 3- to 6-membered cycloalkyl or optionally substituted 3- to 6-membered heterocycle;

D' is selected from the group consisting of —O—, —NR—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted alkyl, and optionally substituted cycloalkyl; and $R^7$ is independently selected from the group consisting of H, halogen, optionally substituted alkyl, optionally substituted cycloalkyl, —OR, and —N(R)$_2$.

Paragraph C2. The compound of Paragraph C1, wherein X is O or S.

Paragraph C3. The compound of Paragraph C1 or Paragraph C2, wherein Y is selected from:

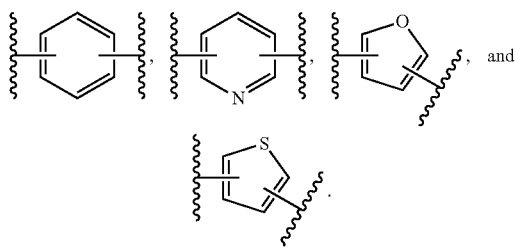

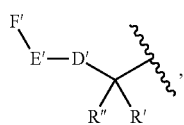

Paragraph C4. The compound of any one of Paragraphs C1-C3, wherein Z is selected from: O, S and CH$_2$.

Paragraph C5. The compound of any one of Paragraphs C1-C4, wherein $R^5$ is a phenyl, optionally substituted with one or more alkyl, —OR, —CN, —CO$_2$R, halogen, —SR, —SOR, —SO$_2$R, —SF$_5$ or —NR$_2$.

Paragraph C6. The compound of any one of Paragraphs C1-C4, wherein $R^5$ is a heterocycle, e.g., morpholine or pyridine, optionally substituted with one or more alkyl, —OR, —CN, —CO$_2$R, halogen, —SR, —SOR, —SO$_2$R, —SF$_5$ or —NR$_2$.

Paragraph C7. The compound of any one of Paragraphs C1-C4, wherein $R^5$ is

Paragraph C8. The compound of Paragraph C7, wherein R' and R" together form a 3- to 6-membered cycloalkyl or heterocycle.

Paragraph C9. The compound of Paragraph C7, wherein R' and R" are each H, or at least one of R' and R" is methyl and any remaining R' or R" is H.

Paragraph C10. The compound of Paragraph C7, wherein at least one of R' and R" is an optionally substituted alkyl.

Paragraph C11. The compound of Paragraph C7, wherein E' is a C$_1$-C$_6$ alkyl and F' is H.

Paragraph C12. The compound of Paragraph C7, wherein F' is an optionally substituted cycloalkyl selected from: cyclopropyl, cyclobutyl, cyclopentyl, and cyclohexyl.

Paragraph C13. The compound of Paragraph C7, wherein F' is an optionally substituted heterocycle selected from: morpholine, azetidine, alkyl-piperidine, alkyl-piperazine, alkyl-diazepane, thiomorpholine 1,1-dioxide, isoindoline-1,3-dione, tetrahydropyran, and pyrrolidone.

Paragraph C14. The compound of Paragraph C7, wherein F' is an optionally substituted aryl selected from: phenyl, optionally substituted with one or more of: alkyl, —CF$_3$, —OR, —CN, —CO$_2$R, halogen, —SR, —SOR, —SO$_2$R, —SF$_5$ or —NR$_2$.

Paragraph C15. The compound of Paragraph C7, wherein F' is an optionally substituted heteroaryl selected from: alkyl-triazole, tetrazole, imidazole, and isoxazole.

Paragraph C16. The compound of any one of Paragraphs C1-C15, wherein $R^1$ is pyridine.

Paragraph C17. The compound of any one of Paragraphs C1-C16, wherein $R^2$ and $R^3$ together are a cyclopropyl, cyclopentyl or cyclohexene.

Paragraph C18. The compound of Paragraph C2 or any one of Paragraphs C4-C17, wherein Y is an optionally substituted

Paragraph C19. A compound selected from Table III or a pharmaceutically acceptable salt, solvate or prodrug thereof.

Paragraph C20. A pharmaceutical composition comprising a compound of any one of Paragraphs C1-C19 and at least one pharmaceutically acceptable excipient.

Paragraph C21. A method of inhibiting p97 in a subject in need thereof, comprising administering to the subject a therapeutically effective amount of a compound of any one of Paragraphs B1-B19 or a therapeutically effective amount of a pharmaceutical composition of Paragraph B20.

Paragraph C22. A method of modulating p97 in a subject in need thereof, comprising administering to the subject a therapeutically effective amount of a compound of any one of Paragraphs C1-C19 or a therapeutically effective amount of a pharmaceutical composition of Paragraph C20.

Paragraph C23. A method of treating cancer or a neurodegenerative disease susceptible to treatment by p97 inhibition in a subject in need thereof comprising administering to the subject a therapeutically effective amount of a compound of any one of Paragraphs C1-C19 or a therapeutically effective amount of a pharmaceutical composition of Paragraph C20.

Paragraph C24. The method of Paragraph C23, wherein the method is a method of treating cancer susceptible to treatment by p97 inhibition, and wherein the cancer is selected from the group consisting of a solid tumor, non-small cell lung carcinoma, multiple myeloma, and mantle cell lymphoma.

Paragraph C25. The method of Paragraph C23, wherein the method is a method of treating a neurodegenerative disease susceptible to treatment by p97 inhibition, and wherein the neurodegenerative disease is selected from the group consisting of inclusion body myopathy (IBM), Paget's disease of the bone (PDB), frontotemporal dementia (FTD) and amyotrophic lateral sclerosis (ALS).

Paragraph C26. A method of treating cancer or a neurodegenerative disease susceptible to treatment by p97 modulation in a subject in need thereof comprising administering to the subject a therapeutically effective amount of a compound of any one of Paragraphs C1-C19 or a therapeutically effective amount of a pharmaceutical composition of Paragraph C20.

Paragraph C27. The method of Paragraph C26, wherein the method is a method of treating cancer susceptible to treatment by p97 modulation, and wherein the cancer is selected from the group consisting of a solid tumor, non-small cell lung carcinoma, multiple myeloma, and mantle cell lymphoma.

Paragraph C28. The method of Paragraph C26, wherein the method is a method of treating a neurodegenerative disease susceptible to treatment by p97 modulation, and wherein the neurodegenerative disease is selected from the group consisting of inclusion body myopathy (IBM), Paget's disease of the bone (PDB), frontotemporal dementia (FTD) and amyotrophic lateral sclerosis (ALS).

The invention claimed is:

1. A compound having a structure of formula (I):

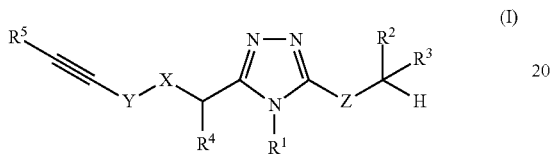

(I)

or a pharmaceutically acceptable salt, solvate or prodrug thereof, wherein:

Z is O, $SO_{0-2}$, NR, $C(R^7)_2$, alkenyl or alkynyl;

$R^2$ and $R^3$ are independently an optionally substituted $C_{1-9}$ cyclic, $C_{3-9}$ heterocyclic, or halogen, or $R^2$ and $R^3$ together form an optionally substituted $C_{3-9}$ cyclic or 3- to 9-membered heterocyclic ring;

$R^1$ is optionally substituted phenyl or an optionally substituted 5- or 6-membered heteroaryl;

$R^4$ is H, $C(R^7)_2$, aryl, or heteroaryl;

X is O or $SO_{0-2}$;

Y is an optionally substituted alkyl, alkenyl, aryl, heteroaryl, cycloalkyl, or heterocycle;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

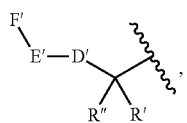

where

R' and R" are each independently selected from H, optionally substituted alkyl, —OR, halogen, —N(R)$_2$, and optionally substituted cycloalkyl or heterocycle;

or R' and R" may together form a 3- to 6-membered cycloalkyl or heterocycle that is optionally substituted;

D' is selected from the group consisting of —O—, —NR—, —OCONR—, —NRSO$_2$—, —NRCO—, —NRSO$_2$NR—, —NRCOO—, —NRCONR—, and —NRC(NR)NR—;

E' is selected from a bond or an optionally substituted $C_1$-$C_6$ alkyl or cycloalkyl;

F' is selected from the group consisting of H, an optionally substituted cycloalkyl, an optionally substituted heterocycle, an optionally substituted aryl, and an optionally substituted heteroaryl;

R is selected from the group consisting of H, optionally substituted alkyl, and optionally substituted cycloalkyl; and $R^7$ is selected from the group consisting of H, halogen, optionally substituted alkyl, optionally substituted cycloalkyl, —OR, and —N(R)$_2$.

2. A compound having a structure of formula (II):

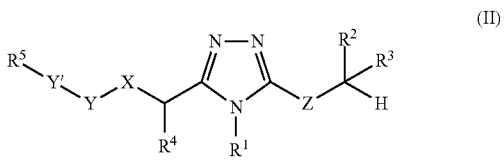

(II)

or a pharmaceutically acceptable salt, solvate or prodrug thereof, wherein:

X is O, $SO_{0-2}$, or NR;

Y is optionally substituted alkyl, optionally substituted alkenyl, alkynyl, optionally substituted aryl, optionally substituted heteroaryl, optionally substituted cycloalkyl, or optionally substituted non-aromatic heterocyclic;

Y' is alkynyl, optionally substituted heteroaryl, or optionally substituted non-aromatic heterocyclic;

$R^2$ and $R^3$ are independently optionally substituted $C_{1-6}$ alkyl, optionally substituted $C_{1-9}$ cyclic, optionally substituted $C_{3-9}$ heterocyclic, or halogen, or $R^2$ and $R^3$ together form an optionally substituted $C_{3-9}$ cyclic or optionally substituted 3- to 9-membered heterocyclic ring;

Z is O, $SO_{0-2}$, NR, $C(R^7)_2$, alkenyl or alkynyl;

$R^1$ is optionally substituted phenyl, optionally substituted 5- or 6-membered heteroaryl, or optionally substituted non-aromatic heterocyclic;

$R^4$ is H, $C(R^7)_2$, aryl, or heteroaryl;

$R^5$ is H, nitrile, an optionally substituted aryl, an optionally substituted heterocycle, optionally substituted $C_1$-$C_6$ alkyl, optionally substituted $C_3$-$C_9$ cycloalkyl, or

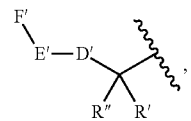

where

R' and R" are each independently selected from the group consisting of H, optionally substituted alkyl, —OR, halogen, —N(R)$_2$, optionally substituted cycloalkyl, and optionally substituted heterocycle;

or R' and R" may together form an optionally substituted 3- to 6-membered cycloalkyl or optionally substituted 3- to 6-membered heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl;

R is independently selected from the group consisting of H, optionally substituted alkyl, and optionally substituted cycloalkyl; and R[7] is independently selected from the group consisting of H, halogen, optionally substituted alkyl, optionally substituted cycloalkyl, —OR, and —N(R)$_2$.

3. The compound of claim 2, wherein Y' is alkynyl.
4. The compound of claim 2, wherein X is O or S.
5. The compound of claim 2, wherein Y is selected from:

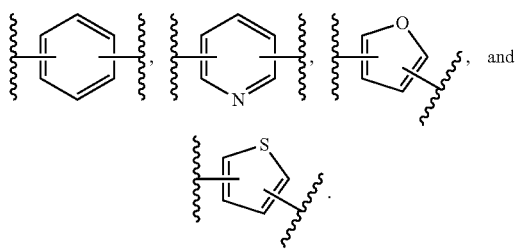

6. The compound of claim 2, wherein Z is selected from O, S and CH$_2$.
7. The compound of claim 2, wherein R$^5$ is a phenyl, optionally substituted with one or more alkyl, —OR, —CN, —CO$_2$R, halogen, —SR, —SOR, —SO$_2$R, —SF$_5$ or —NR$_2$.
8. The compound of claim 2, wherein R$^5$ is a heterocycle optionally substituted with one or more alkyl, —OR, —CN, —CO$_2$R, halogen, —SR, —SOR, —SO$_2$R, —SF$_5$ or —NR$_2$.
9. The compound of claim 2, wherein R$^5$ is

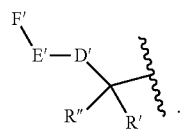

10. The compound of claim 9, wherein R' and R" together form a 3- to 6-membered cycloalkyl or heterocycle.
11. The compound of claim 9, wherein R' and R" are each H, or at least one of R' and R" is methyl and any remaining R' or R" is H.
12. The compound of claim 9, wherein at least one of R' and R" is an optionally substituted alkyl.
13. The compound of claim 9, wherein E' is a C$_1$-C$_6$ alkyl and F' is H.
14. The compound of claim 9, wherein F' is an optionally substituted cycloalkyl selected from the group consisting of cyclopropyl, cyclobutyl, cyclopentyl, and cyclohexyl.
15. The compound of claim 9, wherein F' is an optionally substituted heterocycle selected from the group consisting of morpholine, azetidine, alkyl-piperidine, alkyl-piperazine, alkyl-diazepane, thiomorpholine 1,1-dioxide, isoindoline-1,3-dione, tetrahydropyran, and pyrrolidone.
16. The compound of claim 9, wherein F' is an optionally substituted aryl selected from: phenyl, optionally substituted with one or more of: alkyl, —CF$_3$, —OR, —CN, —CO$_2$R, halogen, —SR, —SOR, —SO$_2$R, —SF$_5$ or —NR$_2$.
17. The compound of claim 9, wherein F' is an optionally substituted heteroaryl selected from the group consisting of alkyl-triazole, tetrazole, imidazole, and isoxazole.
18. The compound of claim 2, wherein R$^1$ is pyridine.
19. The compound of claim 2, wherein R$^2$ and R$^3$ together are a cyclopropyl, cyclopentyl or cyclohexene.
20. The compound of claim 2, wherein Y is an optionally substituted

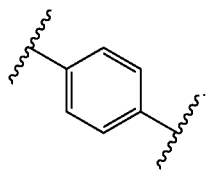

21. The compound of claim 2, selected from

| No | Compound |
|---|---|
| 1 | 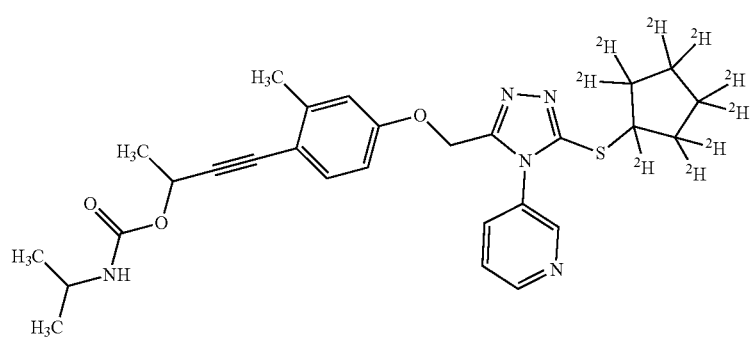 [SMILES: [2H]C1([2H])C([2H])([2H])C([2H])([2H])C([2H])(Sc2nnc(COc3ccc(C#CC(C)OC(=O)NC(C)C)c(C)c3)n2-c2cccnc2)C1([2H])[2H]] |
| 2 | 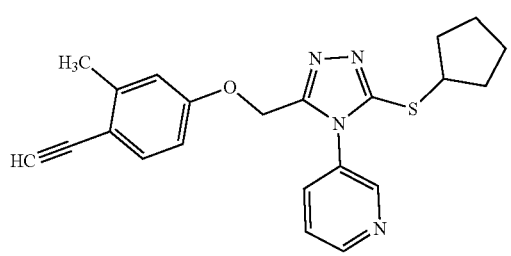 [SMILES: C#Cc1ccc(OCc2nnc(SC3CCCC3)n2-c2cccnc2)cc1C] |

-continued
| No | Compound |
|---|---|
| 3 |  |
| 4 | 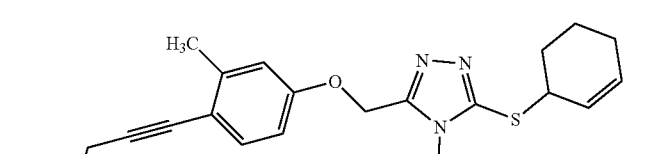 |
| 5 |  |
| 6 | 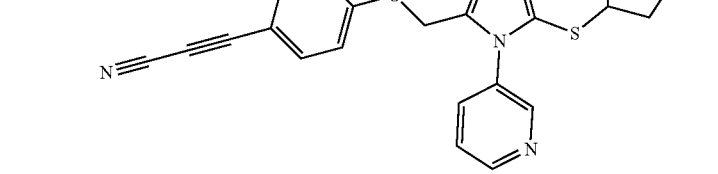 |
| 7 | 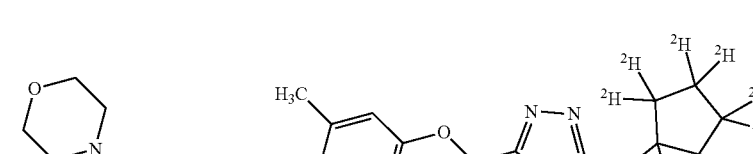 |
| 8 | 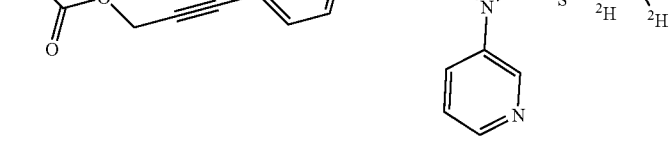 |

-continued
| No | Compound |
|---|---|
| 9 | 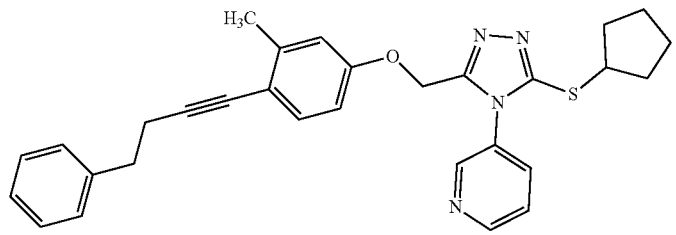 [SMILES: Cc1cc(OCc2nnc(SC3CCCC3)n2-c2cccnc2)ccc1C#CCCc1ccccc1] |
| 10 | 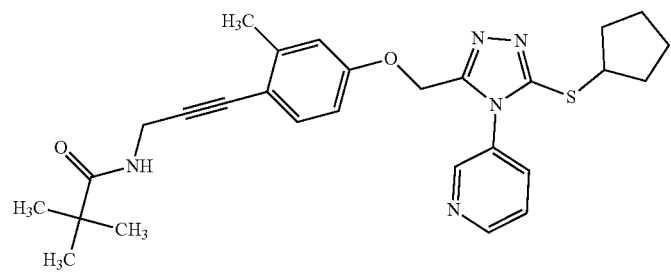 [SMILES: Cc1cc(OCc2nnc(SC3CCCC3)n2-c2cccnc2)ccc1C#CCNC(=O)C(C)(C)C] |
| 11 | 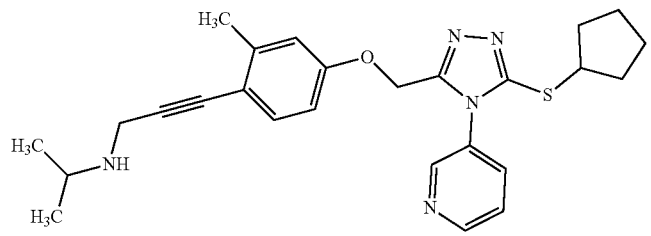 [SMILES: Cc1cc(OCc2nnc(SC3CCCC3)n2-c2cccnc2)ccc1C#CCNC(C)C] |
| 12 | 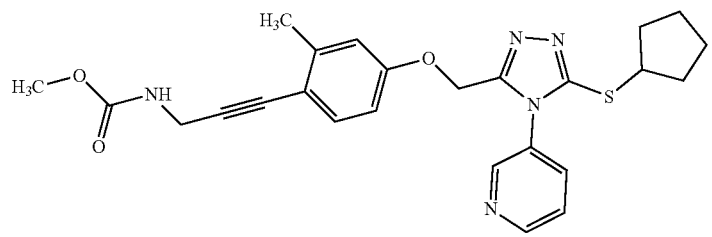 [SMILES: COC(=O)NCC#Cc1ccc(OCc2nnc(SC3CCCC3)n2-c2cccnc2)cc1C] |
| 13 | 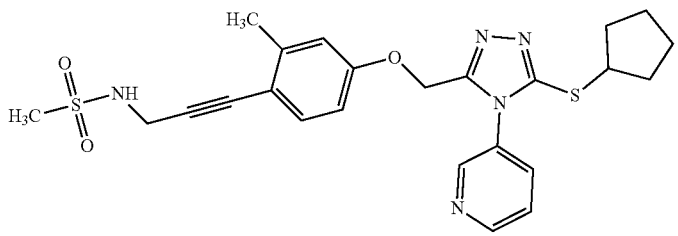 [SMILES: Cc1cc(OCc2nnc(SC3CCCC3)n2-c2cccnc2)ccc1C#CCNS(C)(=O)=O] |
| 14 | 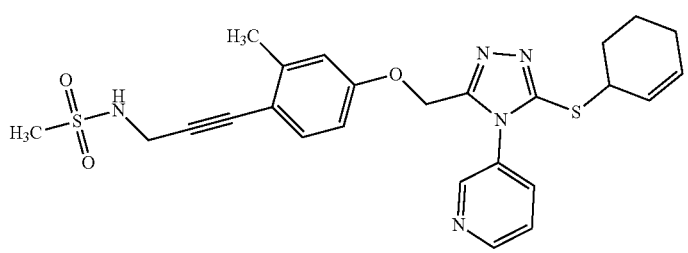 [SMILES: Cc1cc(OCc2nnc(SC3C=CCCC3)n2-c2cccnc2)ccc1C#CCNS(C)(=O)=O] |

-continued
| No | Compound |
|---|---|
| 15 | 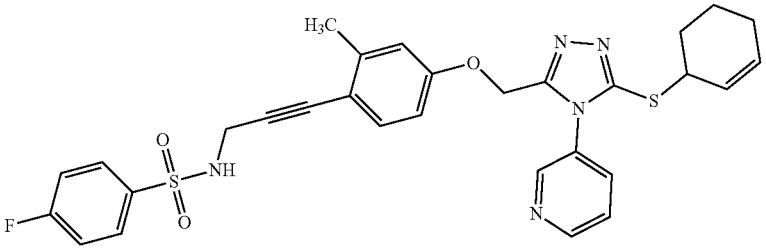 [SMILES: Cc1cc(OCc2nnc(SC3C=CCCC3)n2-c2cccnc2)ccc1C#CCNS(=O)(=O)c1ccc(F)cc1] |
| 16 | 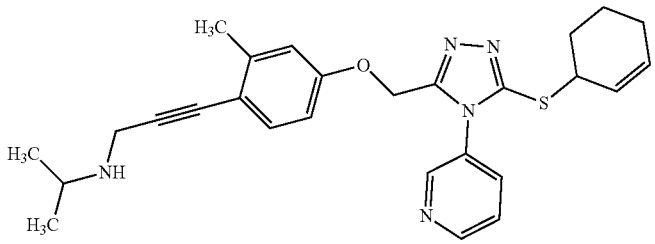 [SMILES: Cc1cc(OCc2nnc(SC3C=CCCC3)n2-c2cccnc2)ccc1C#CCNC(C)C] |
| 17 | 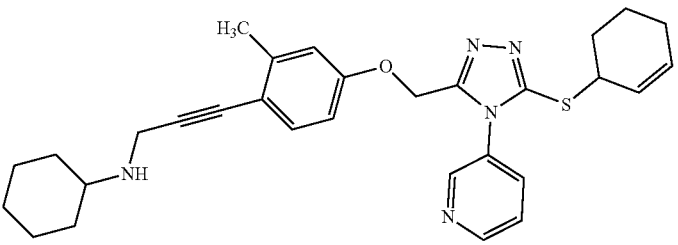 [SMILES: Cc1cc(OCc2nnc(SC3C=CCCC3)n2-c2cccnc2)ccc1C#CCNC1CCCCC1] |
| 18 | 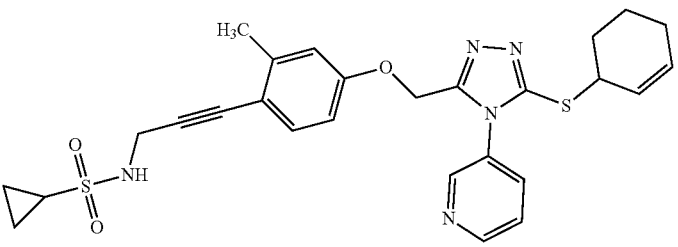 [SMILES: Cc1cc(OCc2nnc(SC3C=CCCC3)n2-c2cccnc2)ccc1C#CCNS(=O)(=O)C1CC1] |
| 19 | 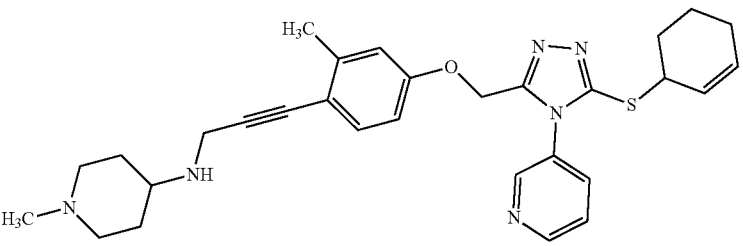 [SMILES: Cc1cc(OCc2nnc(SC3C=CCCC3)n2-c2cccnc2)ccc1C#CCNC1CCN(C)CC1] |

| No | Compound |
|---|---|
| 20 | 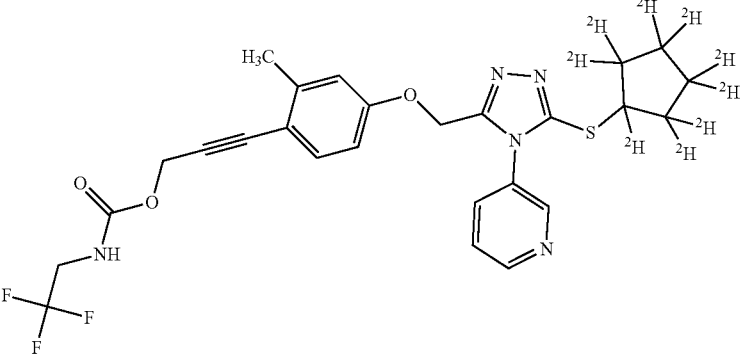 [SMILES: [2H]C1([2H])C([2H])([2H])C([2H])([2H])C([2H])(Sc2nnc(COc3ccc(C#CCOC(=O)NCC(F)(F)F)c(C)c3)n2-c2cccnc2)C1([2H])[2H]] |
| 21 | 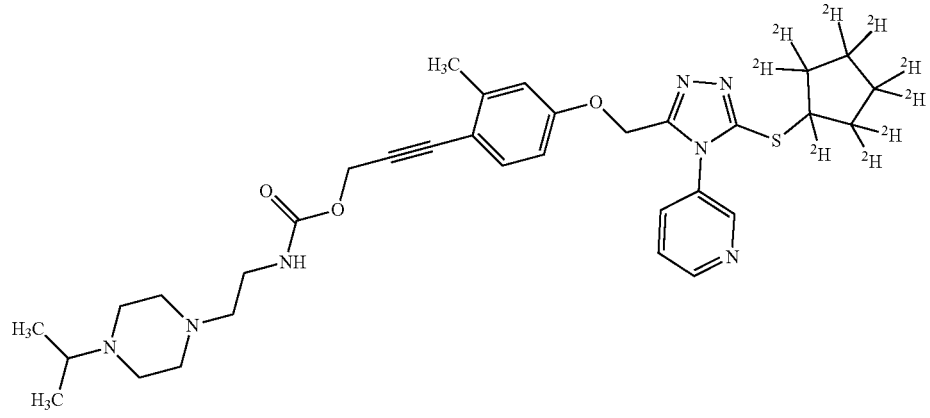 [SMILES: [2H]C1([2H])C([2H])([2H])C([2H])([2H])C([2H])(Sc2nnc(COc3ccc(C#CCOC(=O)NCCN4CCN(C(C)C)CC4)c(C)c3)n2-c2cccnc2)C1([2H])[2H]] |
| 22 | 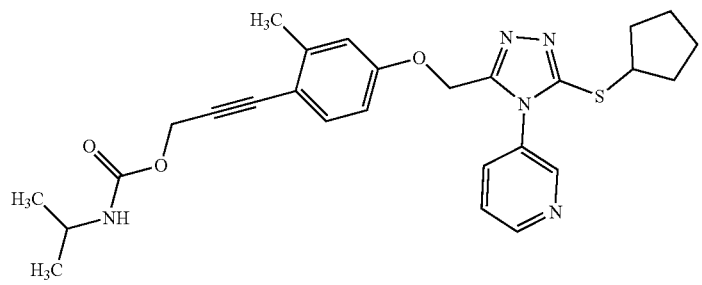 [SMILES: Cc1cc(OCc2nnc(SC3CCCC3)n2-c2cccnc2)ccc1C#CCOC(=O)NC(C)C] |
| 23 | 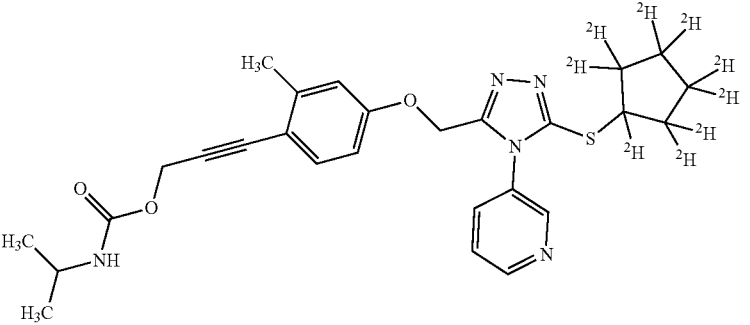 [SMILES: [2H]C1([2H])C([2H])([2H])C([2H])([2H])C([2H])(Sc2nnc(COc3ccc(C#CCOC(=O)NC(C)C)c(C)c3)n2-c2cccnc2)C1([2H])[2H]] |

-continued

| No | Compound |
|---|---|
| 24 | |
| 25 | |
| 26 | |
| 27 | |
| 28 | |

-continued

| No | Compound |
|---|---|
| 29 | |
| 30 | |
| 31 | |
| 32 | |
| 33 | |

| No | Compound |
|---|---|
| 34 | |
| 35 | |
| 36 | |
| 37 | |
| 38 | |

| No | Compound |
|---|---|
| 39 | (chemical structure) |
| 40 | (chemical structure) |
| 41 | (chemical structure) |
| 42 | (chemical structure) |
| 43 | (chemical structure) |

-continued

| No | Compound |
|---|---|
| 44 | |
| 45 | |
| 46 | |
| 47 | |
| 48 | |

-continued
| No | Compound |
|---|---|
| 49 | 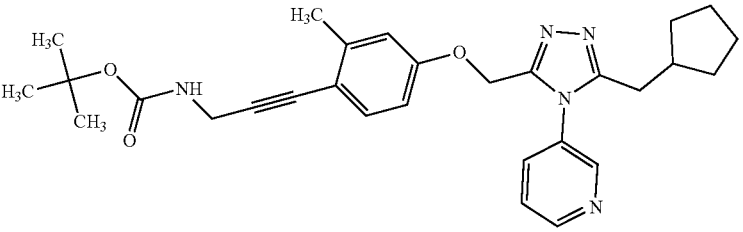 [SMILES: Cc1cc(OCc2nnc(CC3CCCC3)n2-c2cccnc2)ccc1C#CCNC(=O)OC(C)(C)C] |
| 50 | 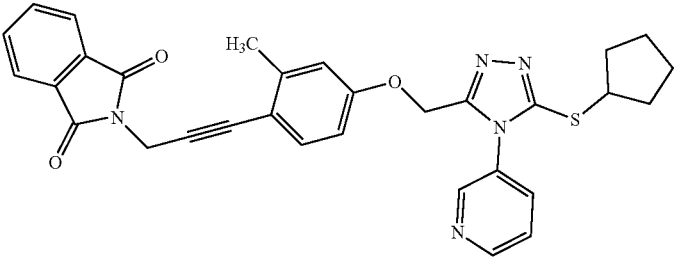 [SMILES: Cc1cc(OCc2nnc(SC3CCCC3)n2-c2cccnc2)ccc1C#CCN1C(=O)c2ccccc2C1=O] |
| 51 | 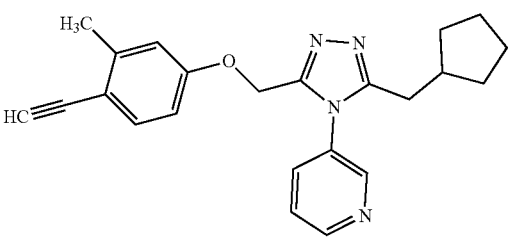 [SMILES: C#Cc1ccc(OCc2nnc(CC3CCCC3)n2-c2cccnc2)cc1C] |
| 52 | 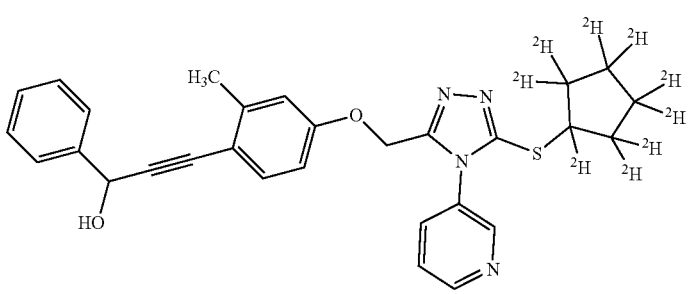 [SMILES: [2H]C1([2H])C([2H])([2H])C([2H])([2H])C([2H])(Sc2nnc(COc3ccc(C#CC(O)c4ccccc4)c(C)c3)n2-c2cccnc2)C1([2H])[2H]] |
| 53 | 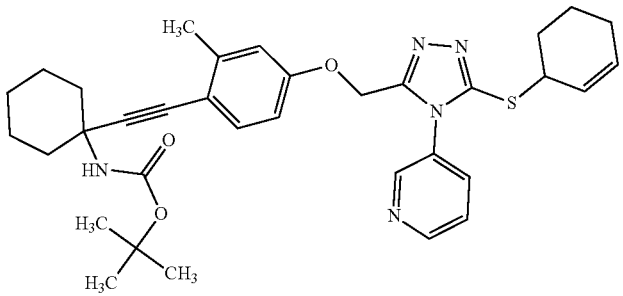 [SMILES: Cc1cc(OCc2nnc(SC3C=CCCC3)n2-c2cccnc2)ccc1C#CC1(NC(=O)OC(C)(C)C)CCCCC1] |
| 54 | 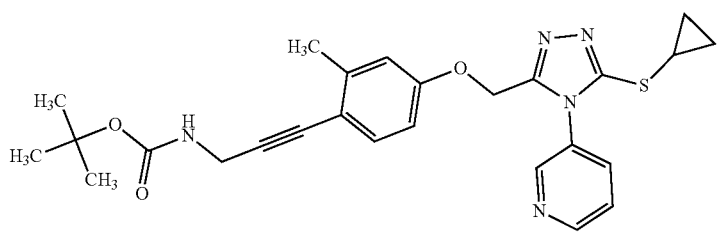 [SMILES: Cc1cc(OCc2nnc(SC3CC3)n2-c2cccnc2)ccc1C#CCNC(=O)OC(C)(C)C] |

-continued

| No | Compound |
|----|----------|
| 55 | |
| 56 | |
| 57 | |
| 58 | |
| 59 | |

| No | Compound |
|----|----------|
| 60 | |
| 61 | |
| 62 | |
| 63 | |
| 64 | |

| No | Compound |
|---|---|
| 65 | |
| 66 | |
| 67 | |
| 68 | |
| 69 | |

-continued

| No | Compound |
|---|---|
| 70 | |
| 71 | |
| 72 | |
| 73 | |

-continued

| No | Compound |
|----|----------|
| 74 | |
| 75 | |
| 76 | |
| 77 | |
| 78 | |

-continued
| No | Compound |
|---|---|
| 79 | 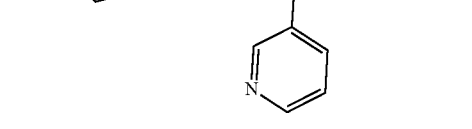 |
| 80 | 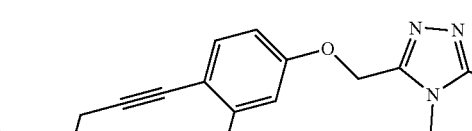 |
| 81 | 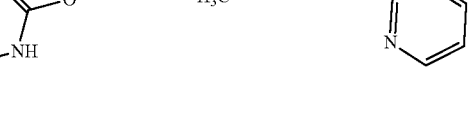 |
| 82 | 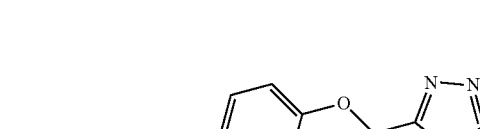 |
| 83 | 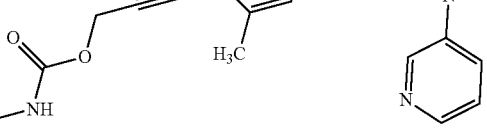 |

| No | Compound |
|---|---|
| 84 | 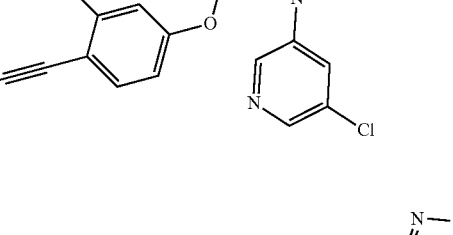 |
| 85 | 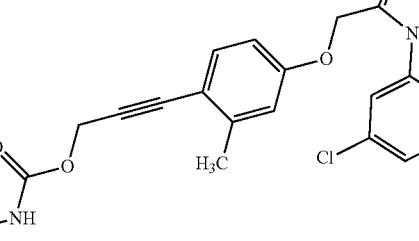 |
| 86 | 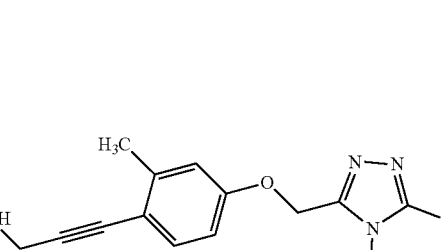 |
| 87 | 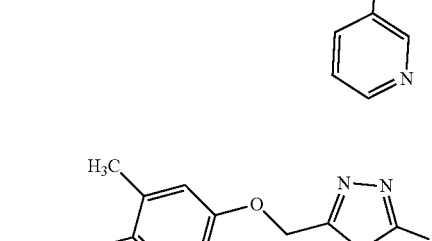 |
| 88 | 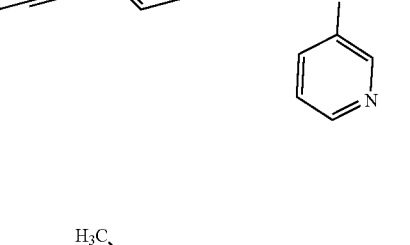 |

| No | Compound |
|---|---|
| 89 | (structure) |
| 90 | (structure) |
| 91 | (structure) |
| 92 | (structure) |

-continued

| No | Compound |
|---|---|
| 93 | |
| 94 | |
| 95 | |
| 96 | |
| 97 | |
| 98 | |

-continued

| No | Compound |
|---|---|
| 99 | |
| 100 | |
| 101 | |
| 102 | |

| No | Compound |
|---|---|
| 103 | |
| 104 | |
| 105 | |
| 106 | |
| 107 | |

-continued
| No | Compound |
|---|---|
| 108 | 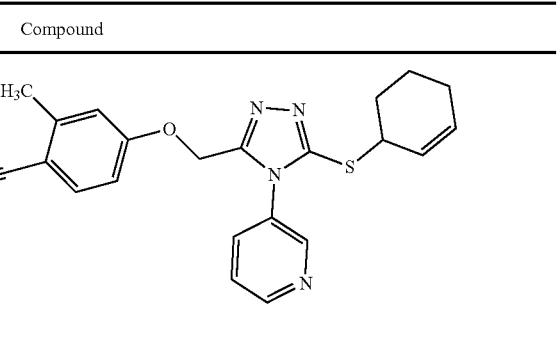 |
| 109 | 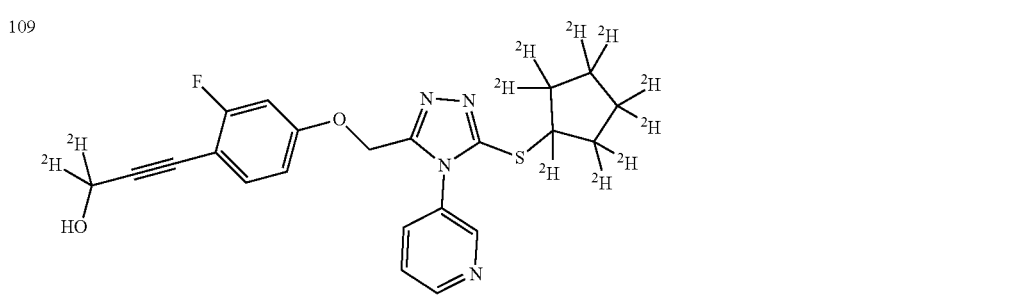 |
| 110 | 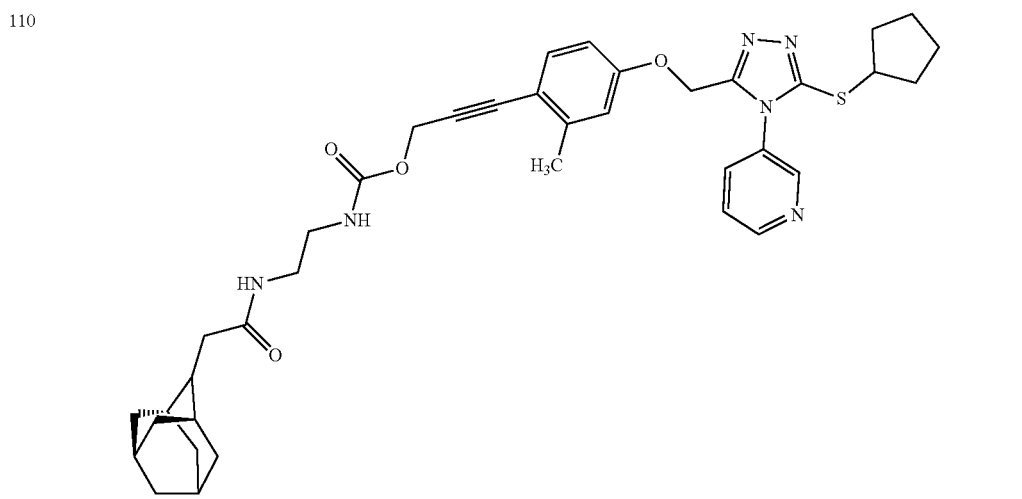 |
| 111 | 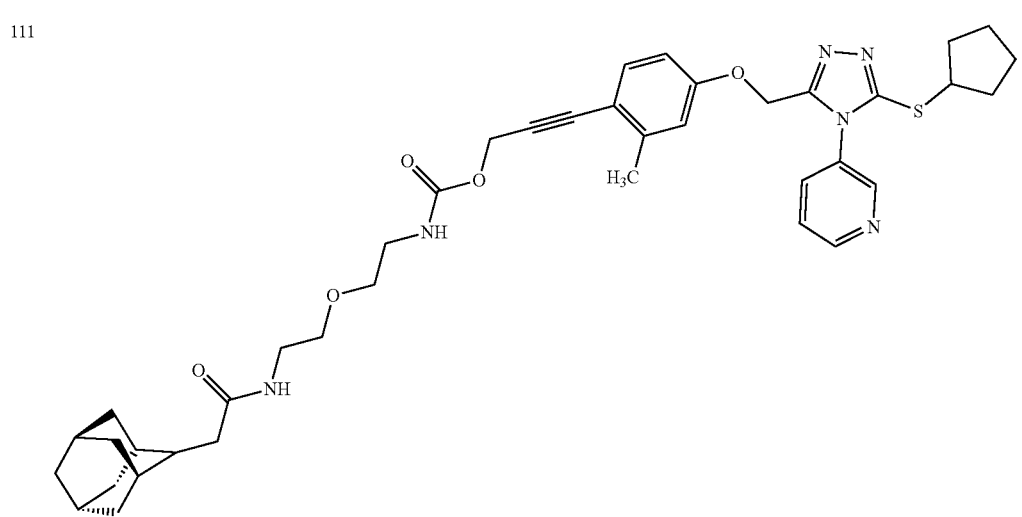 |

| No | Compound |
|---|---|
| 112 | 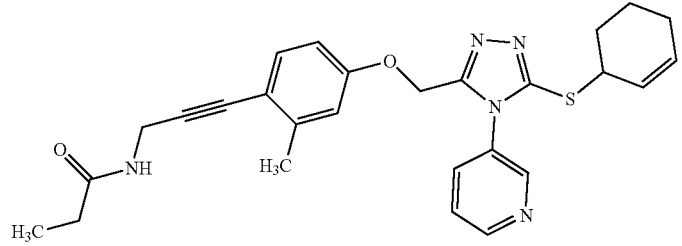 [SMILES: CCC(=O)NCC#Cc1ccc(OCc2nnc(SC3C=CCCC3)n2-c2cccnc2)cc1C] |
| 113 | 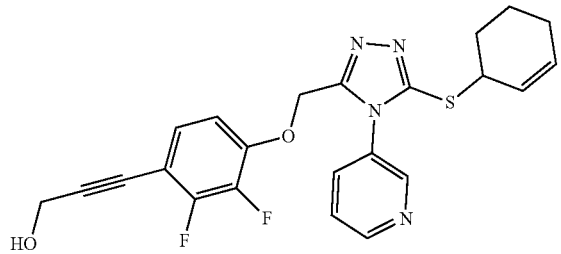 [SMILES: OCC#Cc1ccc(OCc2nnc(SC3C=CCCC3)n2-c2cccnc2)c(F)c1F] |
| 114 | 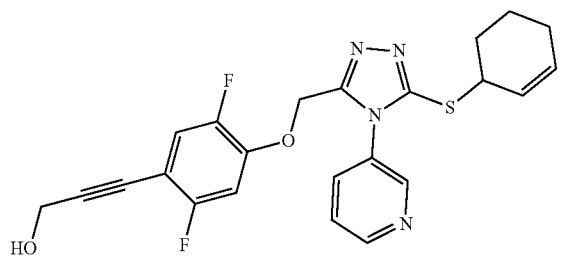 [SMILES: OCC#Cc1cc(F)c(OCc2nnc(SC3C=CCCC3)n2-c2cccnc2)cc1F] |
| 115 | 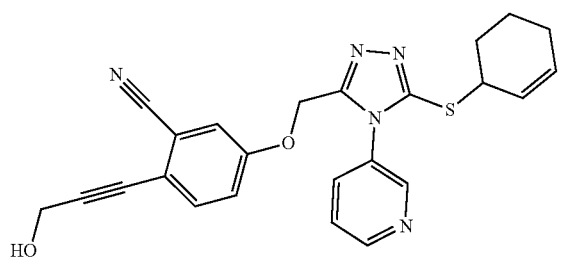 [SMILES: N#Cc1cc(OCc2nnc(SC3C=CCCC3)n2-c2cccnc2)ccc1C#CCO] |
| 116 | 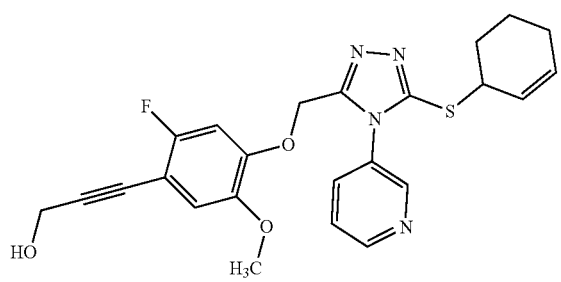 [SMILES: COc1cc(C#CCO)c(F)cc1OCc1nnc(SC2C=CCCC2)n1-c1cccnc1] |

| No | Compound |
|---|---|
| 117 | (structure: 3-(4-((4-(pyridin-3-yl)-5-((cyclopentyl-d9)thio)-4H-1,2,4-triazol-3-yl)methylamino)-2-methylphenyl)prop-2-yn-1-ol) |
| 118 | (structure: 1-methylpiperidin-4-yl carbamate of 3-(4-((5-(cyclohex-2-en-1-ylthio)-4-(pyridin-3-yl)-4H-1,2,4-triazol-3-yl)methoxy)-2,3-difluorophenyl)prop-2-yn-1-ol) |
| 119 | (structure: 1-methylpiperidin-4-yl carbamate of 3-(4-((5-(cyclohex-2-en-1-ylthio)-4-(pyridin-3-yl)-4H-1,2,4-triazol-3-yl)methoxy)-2,5-difluorophenyl)prop-2-yn-1-ol) |
| 120 | (structure: 1-methylpiperidin-4-yl carbamate of 3-(4-((5-(cyclohex-2-en-1-ylthio)-4-(pyridin-3-yl)-4H-1,2,4-triazol-3-yl)methoxy)-2,6-difluorophenyl)prop-2-yn-1-ol) |
| 121 | (structure: 1-methylpiperidin-4-yl carbamate of 3-(4-((5-(cyclohex-2-en-1-ylthio)-4-(pyridazin-3-yl)-4H-1,2,4-triazol-3-yl)methoxy)-2-cyanophenyl)prop-2-yn-1-ol) |

| No | Compound |
|---|---|
| 122 | |
| 123 | |
| 124 | |
| 125 | |
| 126 | |

| No | Compound |
|---|---|
| 127 | 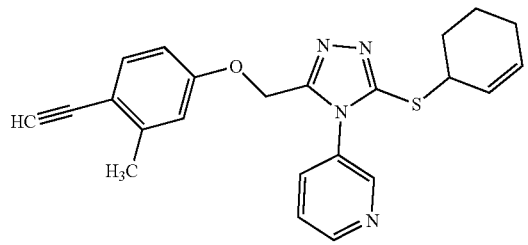 [SMILES: C#Cc1ccc(OCc2nnc(SC3C=CCCC3)n2-c2cccnc2)cc1C] |
| 128 | 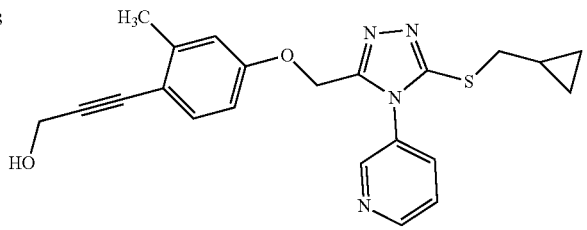 |
| 129 | 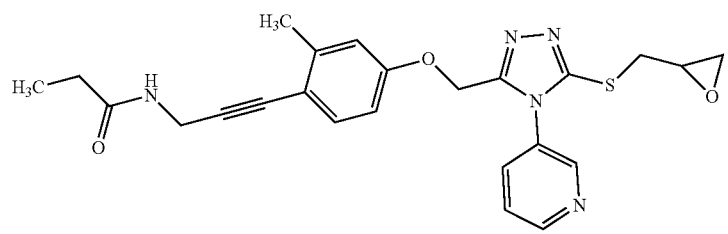 [SMILES: CCC(=O)NCC#Cc1ccc(OCc2nnc(SCC3CO3)n2-c2cccnc2)cc1C] |
| 130 | 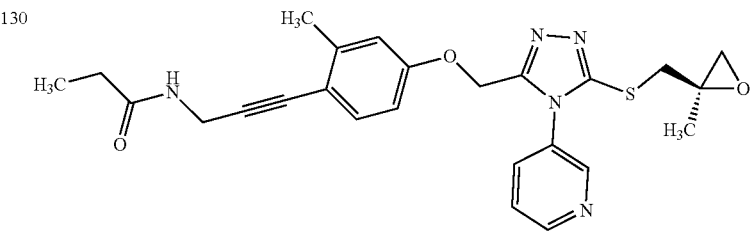 |
| 131 | 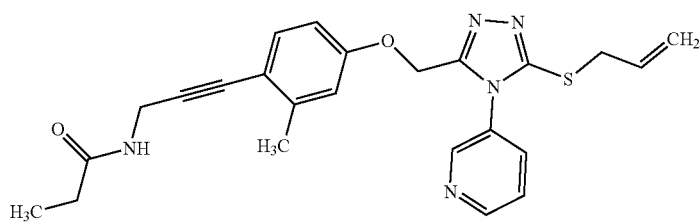 [SMILES: C=CCSc1nnc(COc2ccc(C#CCNC(=O)CC)c(C)c2)n1-c1cccnc1] |

-continued
| No | Compound |
|---|---|
| 132 | 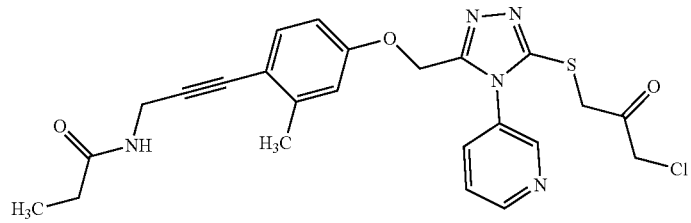 [SMILES: CCC(=O)NCC#Cc1ccc(OCc2nnc(SCC(=O)CCl)n2-c2cccnc2)cc1C] |
| 133 | 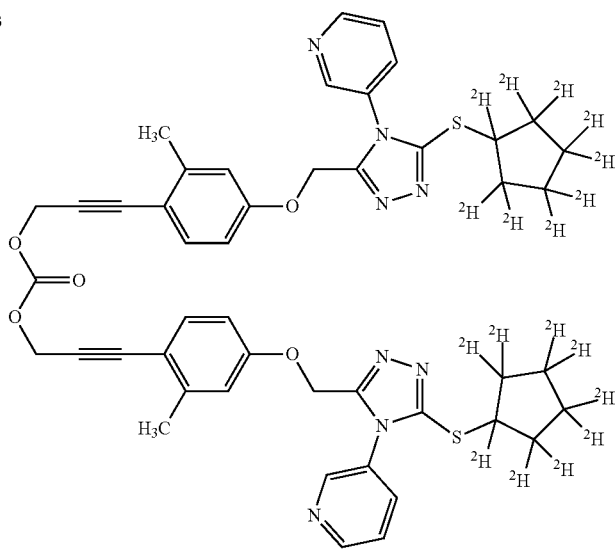 [SMILES: [2H]C1([2H])C([2H])([2H])C([2H])([2H])C([2H])(Sc2nnc(COc3ccc(C#CCOC(=O)OCC#Cc4ccc(OCc5nnc(SC6([2H])C([2H])([2H])C([2H])([2H])C([2H])([2H])C6([2H])[2H])n5-c5cccnc5)cc4C)c(C)c3)n2-c2cccnc2)C1([2H])[2H]] |
| 134 | 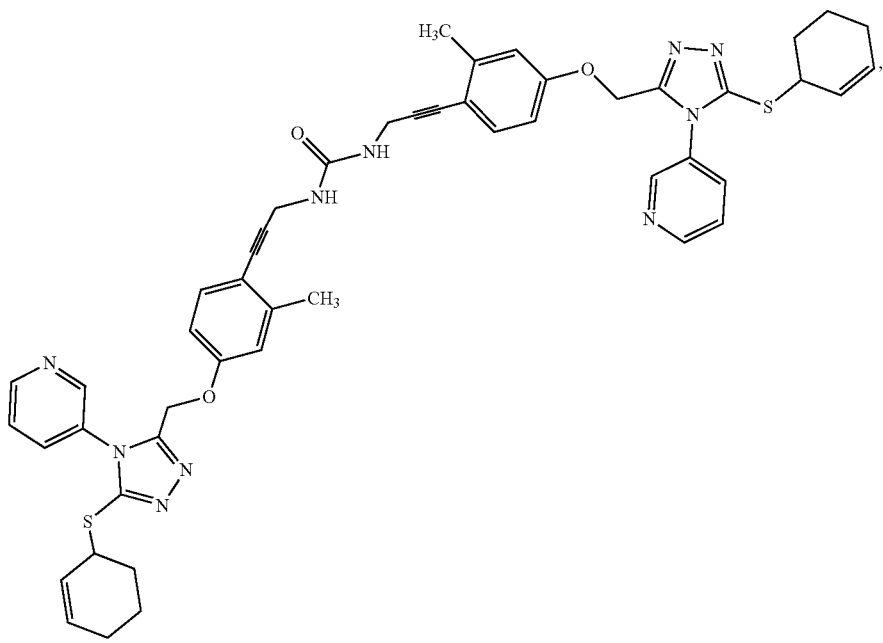 [SMILES: Cc1cc(OCc2nnc(SC3C=CCCC3)n2-c2cccnc2)ccc1C#CCNC(=O)NCC#Cc1ccc(OCc2nnc(SC3C=CCCC3)n2-c2cccnc2)cc1C] | or a pharmaceutically acceptable salt, solvate or prodrug thereof.

22. The compound of claim 21, selected from compound number 40, 106, 119, or 120, or a pharmaceutically acceptable salt, solvate or prodrug thereof.

23. The compound of claim 2, wherein X is O, Y is substituted phenylene, Y' is alkynyl, Z is S, and $R^2$ and $R^3$ together form an optionally substituted $C_{3-9}$ cyclic ring.

24. The compound of claim 23, wherein $R^1$ is pyridine.

25. The compound of claim 23, wherein $R^5$ is

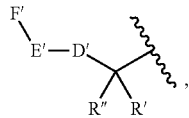

where

R' and R" are each independently selected from the group consisting of H, optionally substituted alkyl, —OR, halogen, —N(R)$_2$, optionally substituted cycloalkyl, and optionally substituted heterocycle;

or R' and R" may together form an optionally substituted 3- to 6-membered cycloalkyl or optionally substituted 3- to 6-membered heterocycle;

D' is selected from the group consisting of —O—, —NR—, —OCONR—, —OCO—, —NRSO$_2$—, —NRCO—, —NRSO$_2$NR—, —NRCOO—, —NRCONR—, and —NRC(NR)NR—;

E' is selected from the group consisting of a bond, an optionally substituted $C_1$-$C_6$ alkyl, optionally substituted $C_1$-$C_6$ alkenyl, and optionally substituted cycloalkyl; and F' is selected from the group consisting of H, an optionally substituted cycloalkyl, an optionally substituted non-aromatic heterocycle, an optionally substituted aryl, and an optionally substituted heteroaryl; and R is independently selected from the group consisting of H, optionally substituted alkyl, and optionally substituted cycloalkyl.

26. A pharmaceutical composition comprising a compound of claim 2 and at least one pharmaceutically acceptable excipient.

* * * * *